US006426074B1

(12) United States Patent
Michel et al.

(10) Patent No.: US 6,426,074 B1
(45) Date of Patent: Jul. 30, 2002

(54) GROUP B STREPTOCOCCUS VACCINE

(75) Inventors: James L. Michel, Chestnut Hill; Lawrence C. Madoff, Brookline; Dennis L. Kasper, Newton Centre, all of MA (US)

(73) Assignee: The Brigham and Women's Hospital Inc., Boston, MA (US)

( * ) Notice: Subject to any disclaimer, the term of this patent is extended or adjusted under 35 U.S.C. 154(b) by 0 days.

(21) Appl. No.: 09/040,181

(22) Filed: Mar. 18, 1998

Related U.S. Application Data
(60) Provisional application No. 60/039,353, filed on Mar. 19, 1997.

(51) Int. Cl.⁷ .............................................. A61K 39/09
(52) U.S. Cl. ................................ 424/244.1; 424/184.1; 424/193.1; 424/197.11; 424/203.1; 530/350; 536/123.1
(58) Field of Search ........................... 424/244.1, 184.1, 424/193.1, 197.11, 203.1; 530/350; 536/123.1

(56) References Cited

U.S. PATENT DOCUMENTS

| | | | | |
|---|---|---|---|---|
| 4,207,414 A | * | 6/1980 | Kasper ......................... 536/1 |
| 4,284,537 A | * | 8/1981 | Beachey ....................... 260/6 |
| 4,324,887 A | * | 4/1982 | Kasper ........................ 536/53 |
| 4,356,263 A | * | 10/1982 | Kasper ....................... 435/101 |
| 4,367,221 A | * | 1/1983 | Kasper |
| 4,367,222 A | * | 1/1983 | Kasper ........................ 424/87 |
| 4,367,223 A | * | 1/1983 | Kasper ........................ 424/92 |
| 4,413,057 A | * | 11/1983 | Carlo et al. ................. 435/101 |
| RE31,672 E | * | 9/1984 | Kasper ........................ 536/53 |
| 4,619,828 A | * | 10/1986 | Gordon et al. ................ 424/92 |
| 4,673,574 A | * | 6/1987 | Anderson .................... 424/92 |
| 4,761,283 A | | 8/1988 | Anderson .................... 424/92 |
| 4,789,735 A | | 12/1988 | Frank et al. ................. 530/395 |
| 5,192,540 A | | 3/1993 | Kuo et al. .................... 424/92 |
| 5,302,386 A | | 4/1994 | Kasper et al. ................ 424/92 |
| 5,370,872 A | | 12/1994 | Cryz et al. .................. 424/194.1 |
| 5,576,002 A | | 11/1996 | Jennings et al. ........... 424/197.11 |
| 5,604,108 A | | 2/1997 | Becker et al. .............. 435/7.32 |
| 5,648,241 A | | 7/1997 | Michel et al. .............. 435/69.3 |
| 5,820,860 A | | 10/1998 | Michel et al. .............. 424/165.1 |
| 5,843,444 A | | 12/1998 | Michel et al. .............. 424/165.1 |
| 5,847,081 A | | 12/1998 | Michel et al. .............. 530/350 |
| 5,858,362 A | | 1/1999 | Michel et al. .............. 424/165.1 |
| 5,968,521 A | * | 10/1999 | Michel et al. |

FOREIGN PATENT DOCUMENTS

| | | |
|---|---|---|
| EP | 0 038 265 A1 * | 10/1981 |
| EP | 0 071 515 A1 * | 2/1983 |
| EP | 0 206 852 A1 * | 12/1986 |
| EP | 0 245 045 A2 * | 11/1987 |
| WO | WO 94/10317 | 5/1994 |

OTHER PUBLICATIONS

Anderson, P., "Antibody Responses to *Haemophilus influenzae* Type b and Diphtheria Toxin Induced by Conjugates of Oligosaccharides of the Type b Capsule with the Nontoxic Protein $CRM_{197}$," *Infec. and Immun. 39*:233–238 (1983).*
Aruffo, A. and B. Seed, "Molecular cloning of a CD28 cDNA by a high–efficiency COS cell expression system," *Proc. Natl. Acad. Sci. USA 84*:8573–8577 (1987).*
Baker, C.J. and Kasper, D.L., "Group B Streptococcal Vaccines," *Rev. of Infec. Dis. 7*:458–467 (1985).*
Baker, C.J., "Group B Streptococcal Infection in Newborns: Prevention at Last?," *New Eng. J. Med. (Editorial) 314*:1702–1704 (1986).
Baker, C.J., et al., "Immunization of Pregnant Women with a Polysaccharide Vaccine of Group B Streptococcus," *New Eng. J. Med. 319*:1180–1185 (1988).
Baker, C.J. and M.S. Edwards, "Group B Streptococcal Infections," in: *Infectious Diseases of the Fetus and Newborn Infant*, Third Edition, Remington, J.S. and J.O Klien, eds., Philadelphia, W.B. Saunders Co., Philadelphia, pp. 742–811 (1990).
Baltimore, R.S., et al., "Antigenic Specificity of Opsonophagocytic Antibodies in Rabbit Anti–sera to Group B Streptococci," *J. Immunol. 118*:673–678 (1977).
Beachey, E.H., et al., "Human Immune Response to Immunization with a Structurally Defined Polypeptide Fragment of Streptococcal M Protein," *J. Exp. Med. 150*:862–877 (1979).
Beachey, E.H., et al., "Protective Immunogenicity and T Lymphocyte Specificity of a Trivalent Hybrid Peptide Containing $NH_2$–Terminal Sequences of Types 5,6, and 24 M Proteins Synthesized in Tandem," *J. Exp. Med. 166*:647–656 (1987).
Bessler, W.G., et al., "Specific Antibodies Elicited by Antigen Covalently Linked to a Synthetic Adjuvant," *Immunobiol. 170*:239–244 (1985).

(List continued on next page.)

Primary Examiner—Jennifer E. Graser
(74) Attorney, Agent, or Firm—Sterne, Kessler, Goldstein & Fox P.L.L.C.

(57) ABSTRACT

The invention concerns a vaccine capable of protecting a recipient from infection caused group B Streptococcus. The vaccine comprises polysaccharide-protein moieties or protein moieties without a polysaccharide. The vaccine can contain, inter alia, (a) a group B Streptoccus polysaccharide conjugated to (b) either the N-terminal region of the epsilon antigen, a fragment thereof or their functional derivatives such that the vaccine retains the ability to elicit protective antibodies against group B Streptoccus. The vaccine may contain only one type of such polysaccharide-protein unit or may contain a mixture of more than one type of unit. Alternatively, the vaccine may contain antigens from different species of Group B Streptococcus. Additionally, the invention concerns a passive vaccine obtained following immunization with either the capsular polysaccharide-protein conjugate or the non-conjugated protein.

9 Claims, 16 Drawing Sheets

OTHER PUBLICATIONS

Bevanger, L. and J.A. Mæland, "Complete and Incomplete Ibc Protein Fraction in Group B Streptococci," *Acta. Path. Microbiol. Scand. Sect. B 87*:51–54 (1979).

Bevanger, L. and O.–J. Iverson, "The Ibc Protein Fraction of Group B Streptococci: Characterization of Protein Antigens Extracted by HC1," *Acta. Path. Microbiol. Scand. Sect. B 89*:205–209 (1981).

Bevanger, L., "Ibc Proteins as Serotype Markers of Group B Streptococci," *Acta. Path. Microbiol. Immunol.Scand. Sect. B 91*:231–234 (1983).

Bevanger, L., "The Ibc Proteins of Group B Streptococci: Isolation of the α and β Antigens by Immunosorbent Chromatography and Test for Human Serum Antibodies Against the Two Antigens," *Acta. Path. Microbiol. Immunol. Scand. Sect. B 93*:113–119 (1985).

Bevanger, L. and A.I. Næss, "Mouse–Protective Antibodies Against the Ibc Proteins of Group B Streptococci," *Acta. Path. Microbiol. Immunol. Scand. Sect. B 93*:121–124 (1985).

Bollon, A.P. and M. Stauver, "DNA Transformation Efficiency of Various Bacterial and Yeast Host–Vector Systems," *J. Clin. Hematl. Oncol. 10*:39–48 (1980).

Botstein, D., et al., "Making Mutations in vitro and Putting Them Back into Yeast," *Miami Winter Symp. 19*:265–274 (1982).

Bremm, K.–D., et al., "Release of Lipidmediators (Leukotrienes, PAF) by Bacterial Toxins from Human Polymorphonuclear Granulocytes," in *Bacterial Protein Toxins*, Fehrenbach, F.J., et al., eds., Gustav Fischer Inc., New York, pp. 103–104 (1988).

Broach, J.R., "The Yeast Plasmid 2μ Circle," in *The Molecular Biology of the Yeast Saccharomyces: Life Cycle and Inheritance*, Strathern, J.N., et al., eds., Cold Spring Harbor Laboratory Press, Cold Spring Harbor, New York, pp. 445–470 (1981).

Broach, J.R., "The Yeast Plasmid 2μ Circle," *Cell 28*:203–204 (1982).

Chu, C., et al., "Further Studies on the Immunogenicity of *Haemophilus influenzae* Tybe b and Pneumococcal Type 6A Polysaccharide–Protein Conjugates," *Infect.and Immun. 40*:245–256 (1983).

Cleat, P.H. and K.N. Timmis, "Cloning and Expression in *Escherichia coli* of the Ibc Protein Genes of Group B Streptococci: Binding of Human Immunoglobulin A to the Beta Antigen," *Infec. and Immun. 55*:1151–1155 (1987).

Dale, J. B. and E.H. Beachey, "Unique and Common Protective Epitopes Among Different Serotypes of Group A Streptococcal M Proteins Defined with Hybridoma Antibodies," *Infec. and Immun. 46*:267–269 (1984).

Dunn, B. et al., "Quantitation of Proteins," in: *Current Protocols in Molecular Biology*, vol. 2, Ausubel, F.M., et al., eds., John Wiley & Sons, Inc., New York, p. 10.1.1–10.1.13 (1994).

Eggleston, I.M. and M. Mutter, "Protein De Novo Design: Macromolecules with Tailormade properties," *Macromolecular Symposia 101*:397–404 (Jan. 1996).

Farley, M.M., et al., "A Population–Based Assessment of Invasive Disease Due to Group B Streptococcus in Nonpregnant Adults," *N. England J. Med. 328*:1807–1811 (1993).

Fehrenbach, F.J., et al., "Role of CAMP–Factor (Protein B) for Virulence," in *Bacterial Protein Toxins*, Fehrenbach, F.J., et al., eds., Gustav Fischer Inc., New York, pp. 351–357 (1988).

Ferrieri, P. et al., "Biochemical and Immunological Characterization of the Extracellular Nucleases of Group B Streptococci," *J. Exp. Med. 151*:56–68 (1980).

Ferrieri, P., et al., "Production of Bacteremia and Meningitis in Infant Rats with Group B Streptococcal Serotypes," *Infec.and Immun. 27*:1023–1032 (1980).

Ferrieri, P., "Surface–Localized Protein Antigens of Group B Streptococci," *Rev. Infec. Diseases 10*:S363–S366 (1988).

Fischetti, V.A., et al., "Streptococcal M Protein Extracted by Nonionic Detergent," *J. Exp. Med. 144*:32–53 (1976).

Fischetti, V.A., "Streptococcal M Protein Extracted by Nonionic Detergent II. Analysis of the Antibody Response to the Multiple Antigenic Determinants of the M–Protein Molecule," *J. Exp. Med. 146*:1108–1123 (1977).

Fischetti, V.A., et al., "Conservation of a hexapeptide sequence in the anchor region of surface proteins from Gram–positive cocci," *Mol. Microbiol. 4*:1603–1605 (1990).

Gallagher, S.A. et al., "Electrophoretic Separation of Proteins," in: *Current Protocols in Molecular Biology*, vol. 2, F.M., Ausubel, et al., eds., John Wiley & Sons Inc., New York, pp. 10.2.1–10.2.35 (1994).

Gallagher, S.A. et al., "Detection of Proteins," in: *Current Protocols in Molecular Biology*, vol. 2, Ausubel, F.M., et al., eds., John Wiley & Sons Inc., New York, pp. 10.6.1–10.6.8 (1994).

Ghose, A.C. and F. Karush, "Induction of Polyclonal and Monoclonal Antibody Responses to Cholera Toxin by the Synthetic Peptide Approach," *Molec. Immunol. 25*:223–230 (1988).

Gravekamp, C., et al., "Variation in Repeat Number within the Alpha C Protein of Group B Streptococci Alters Antigenicity and Protective Epitopes," *Infect.and Immun. 64*:3576–3583 (Sep. 1996).

Grodberg, J. and J.J. Dunn, "ompT Encodes the *Escherichia coli* Outer Membrane Protease That Cleaves T7 RNA Polymerases during Purification," *J. Bacteriol. 170*:1245–1253 (1988).

Hedén, L.–O., et al. "Molecular characterization of an IgA receptor from group B streptococci: sequence of the gene, identification of a proline–rich region with unique structure and isolation of N–terminal fragments with IgA–binding capacity," *Eur. J. Immunol. 21*:1481–1490 (1991).

Hervás, J.A., et al., "Neonatal Group B Streptococcal Infection in Mallorca, Spain," *Clin. Infect. Dis. 16*:714–718 (1993).

Hill, H.R., "Group B streptococcal infections," in *Sexually Transmitted Diseases*, McGraw–Hill Inc., New York, pp. 397–407 (1984).

Hojo, H. and S. Aimoto, "Protein Synthesis Using S–Alkyl Thioester of Partially Protected Peptide Segments. Synthesis of DNA–Binding Protein of *Bacillus staerothermophilus*," *Bull. Chem. Soc. Jpn. 65*:3055–3063 (1992).

Hollingshead, S.K., et al., "Complete Nucleotide Sequence of Type 6 M Protein of the Group A Streptococcus," *J. Biol. Chem., 261*:1677–1686 (1986).

Hollingshead, S.K., et al., "Size variation of group A streptococcal M protein is generated by homologous recombination between intragenic repeats," *Mol. Gen. Genet. 207*:196–203 (1987).

Hull, R.A., et al., "Construction and Expression of Recombinant Plasmids Encoding Type 1 or D–Mannose–Resistant Pili from a Urinary Tract Infection *Escherichia coli* Isolate," *Infect. and Immun.* 33:933–938 (1981).

Huynh, T.V., et al., "Constructing and Screening cDNA Libraries in λgt10 and λgt11," in: *DNA Cloning, A Practical Approach,* vol. 1, Glover, D.M., ed., IRL Press, Oxford, England, pp. 49–78 (1985).

Insel, R.A., "Maternal Immunization to Prevent Neonatal Infections," *New Eng. J. Med. (Editorial)* 319:1219–1220 (1988).

Jacob, C.O., et al., "Priming immune response to cholera toxin induced by synthetic peptides," *Eur. J. Immun.* 16:1057–1062 (1986).

Jennings, H.J., et al., "Structure of Native Polysaccharide Antigens of Type Ia and Type Ib Group B Streptococcus," *Biochem.* 22:1258–1264 (1983).

Jerlström, P.G., et al., "The IgA–binding β antigen of the c protein complex of Group B streptococci: sequence determination of its gene and detection of two binding regions," *Mol. Microbiol.* 5:843–849 (1991).

Johnson, D.R., et al., "Group B Streptococcal Ibc Protein Antigen: Distribution of Two Determinants in Wild–Type Strains of Common Serotypes," *J. Clin. Microbiol.* 19:506–510 (1984).

Kasper, D.L., et al., "Immunochemical Analysis and Immunogenicity of the Type II Group B Streptococcal Capsular Polysaccharide," *J. Clin. Invest.* 72:260–269 (1983).

Kasper, D.L., et al., "Cell Structure and Antigenic Composition of GBS," *Antibiot. Chemother.* 35:90–100 (1985).

Kasper, D.L., "Bacterial Capsule–Old Dogmas and New Tricks," *J. Infect. Dis.* 153:407–415 (1986).

Kasper, D.L., et al., "Glycoconjugate Vaccines for the Prevention of Group–B Streptococcal Infections," in *Vaccines 94,* Norrby, E., (ed.), Cold Spring Harbor Laboratory Press, Cold Spring Harbor, New York, pp. 113–117 (1994).

Kasper, D.L., "Immune Response to Type III Group B Streptococcal Polysaccharide–Tetanus Toxoid Conjugate Vaccine," *J. Clin. Invest.* 98:2308–2314 (Nov. 1996).

Kehoe, M.A., "Group A streptococcal antigens and vaccine potential," *Vaccine* 9:797–806 (1991).

Kikuni, Takaisi and F.G. Fehrenbach, "Production and Cellular Compartmentation of Protein B (CAMP–Factor) from Group B Streptococci," in *Bacterial Protein Toxins,* Fehrenbach, F.J., et al., eds., Gustav Fischer Inc., New York, pp. 165–166 (1988).

Kling, D.E., et al., "Characterization of Two Distinct Opsonic and Protective Epitopes within the Alpha C Protein of the Group B Streptococcus," *Infect.and Immun.* 65:1462–1467 (Apr. 1997).

Klipstein, F.A., et al., "Development of a Vaccine of Cross–Linked Heat–Stable and Heat–Labile Enterotoxins That Protects Against *Escherichia coli* Producing Either Enterotoxin," *Infect. and Immun.* 37:550–557 (1982).

Lachenauer, C.S. and L.C. Madoff, "A Protective Surface Protein from Type V Group B Streptococci Shares N–Terminal Sequence Homology with the Alpha C Protein," *Infect.and Immun.* 64:4255–4260 (Oct. 1996).

Lancefield, R.C., et al., "Multiple Mouse–Protective Antibodies Directed Against Group B Streptococci," *J. Exp. Med.* 142:165–179 (1975).

Larsson, C., et al., "Experimental Vaccination against Group B Streptococcus, an Encapsulated Bacterium, with Highly Purified Preparations of Cell Surface Proteins Rib and α," *Infect.and Immun.* 64:3518–3523 (Sep. 1996).

Lepow, M., "Clinical trials of the *Haemophilus influenzae* type b capsular polysaccharide–diphtheria toxoid conjugate vaccine," *Pediat. Infect. Dis. J.* 6:804–807 (1987).

Levy, N.J., et al., "Potentiation of Virulence by Group B Streptococcal Polysaccharides," *J. Infec. Dis.* 149:851–860 (1984).

Macrina, F.L., "Molecular Cloning of Bacterial Antigens and Virulence Determinants," *Ann. Rev. Microbiol.* 38:193–219 (1984).

Madoff, L.C., et al., "Phenotypic Diversity in the Alpha C Protein of Group B Streptococci," *Infect.and Immun.* 59:2638–2644 (1991).

Madoff, L.C., et al., "A Monoclonal Antibody Identifies a Protective C–Protein Alpha–Antigen Epitope in Group B Streptococci," *Infect.and Immun.* 59:204–210 (1991).

Madoff, L.C., et al., "Protection of Neonatal Mice from Group B Streptococcal Infection by Maternal Immunization with Beta C Protein," *Infect. and Immun.* 60:4989–4994 (1992).

Madoff, L.C., et al., "Maternal Immunization of Mice with Group B Streptococcal Type III Polysaccharide–Beta C Protein Conjugate Elicits Protective Antibody to Multiple Serotypes," *J. Clin. Invest.* 94:286–292 (1994).

Madoff, L.C., et al. "Group B streptococci escape host immunity by deletion of tandem repeat elements of the alpha c protein," *Proc. Natl. Acad. Sci. USA.* 93:4131–4136 (Apr. 1996).

Maniatis, T., "Recombinant DNA Procedures in the Study of Eukaryotic Genes," in: *Cell Biology: A Comprehesive Treatise,* vol. 3, *Gene Expression: The Production of RNA's,* Academic Press, New York., pp. 563–608 (1980).

Messing, J. and J. Vieira, "A new pair of M13 vectors for selecting either DNA strand of double–digest restriction fragments," *Gene* 19:269–276 (1982).

Michel, J.L., "Group B Streptococcal infections: an update," *Inf. Dis. Practice* 13:1–12 (1990).

Michel, J.L., et al. "C Proteins of Group B Streptococci," in: *Genetics and Molecular Biology of Streptococci, Lactococci, and Enterococci,* Dunny, G.M., et al., eds., American Society for Microbiology, Washington, D.C., pp. 214–218 (1991).

Michel, J.L., et al., "Cloned Alpha and Beta C–Protein Antigens of Group B Streptococci Elicit Protective Immunity," *Infect.and Immun.* 59:2023–2028 (1991).

Michel, J.L., et al., "Large, identical, tandem repeating units in the C protein alpha antigen gene, bca, of group B streptococci," *Proc. Natl. Acad. Sci. USA* 89:10060–10064 (1992).

Muir, T.W., and S.B.H. Kent, "The chemical synthesis of proteins," *Curr. Opin. Biotech.* 4:420–427 (1993).

Navarre, W.W., and Schneewind, O., "Proteolytic cleavage and cell wall anchoring at the LPXTG motif of surface proteins in Gram–positive bacteria," *Mol. Microbiol.* 14:115–121 (1994).

Norrander, J., et al., "Construction of improved M13 vectors using oligodeoxynucleotide–directed mutagenesis," *Gene* 26:101–106 (1983).

Paoletti, L.C., et al., "Group B Streptococcus Type III Glycoconjugate Vaccines," *Trends in Glycosci. Glytechnol.* 4:269–278 (1992).

Paoletti, L.C., et al., "Neonatal Mouse Protection against Infection with Multiple Group B Streptococcal (GBS) Serotypes by Maternal Immunization with a Tetravalent GBS Polysaccharide–Tetanus Toxoid Conjugate Vaccine," *Infect. and Immun. 62:*3236–3243 (1994).

Paoletti, et al., "Immunogenicity of Group B Streptococcus Type III Polysaccharide–Tetanus Toxoid Vaccine in Baboons," *Infect. and Immun. 64:*677–679 (Feb. 1996).

Parker, J.M.R., et al., "A General Method to Prepare Synthetic Peptide Conjugates," in: *Modern Approaches to Vaccines,* Chanock, R.M. and R.A. Lerner, eds., Cold Spring Harbor Laboratory, Cold Spring Harbor, New York, pp. 133–138 (1984).

Payne, N.R. and P. Ferrieri, "The Relation of the Ibc Protein Antigen to the Opsonization Differences Between Strains of Type II Group B Streptococci," *J. Infect. Dis. 151:*672–681 (1985).

Payne, N.R., et al. , "Effect of Differences in Antibody and Complement Requirements on Phagocytic Uptake and Intracellular Killing of "c" Protein–Positive and –Negative Strains of Type II Group B Streptococci," *Infect. and Immun. 55:*1243–1251 (1987).

Posnett, D.N., et al., "A Novel Method for Producing Anti–peptide Antibodies," *J. Biol. Chem. 263:*1719–1725 (1988).

Pritchard, D.G., et al., "Immunochemical Characterization of the Polysaccharide Antigens of Group B Streptococci," *Rev. Infec. Dis. 10:*S367–S371 (1988).

Rodewald, A.K., et al., "Neonatal Mouse Model of Group B Streptococcal Infection," *J. Infect. Dis. 166:*635–639 (1992).

Rubens, C.E., et al., "Transposon mutagenesis of type III group B Streptococcus: Correlation of capsule expression with virulence," *Proc. Natl. Acad. Sci. USA. 84:*7208–7212 (1987).

Rühlmann, J., et al., "Separation of Large Hydrophobic Fragments of Protein B (CAMP–Factor)," in *Bacterial Protein Toxins,* Fehrenbach, F.J., et al., eds., Gustav Fischer Inc., New York, pp. 63–64 (1988).

Russell–Jones, G.J., et al., "A Surface Receptor Specific for Human IgA on Group B Streptococci Possessing the Ibc Protein Antigen," *J. Exp. Med. 160:*1467–1475 (1984).

Russell–Jones, G.J. and E.C. Gotschlich, "Identification of Protein Antigens of Group B Streptococci, with Special Reference to the Ibc Antigens," *J. Exp. Med. 160:*1476–1484 (1984).

Schneewind, O., et al., "Cloning and Expression of the CAMP Factor of Group B Streptococci in *Escherichia coli,*" *Infec. and Immun.* 56:2174–2179 (1988).

Schneewind, O. et al., "Cell wall sorting signals in surface proteins of Gram–positive bacteria," *EMBO J. 12:*4803–4811 (1993).

Schnölzer, M. and S.B.H. Kent, "Constructing Proteins by Dovetailing Unprotected Synthetic Peptides: Backbone–Engineered HIV Protease," *Science 256:*221–225 (1992).

Scott, J.R., et al., "Relationship of M protein genes in Group A streptococci," *Proc. Natl. Acad. Sci. USA 82:*1822–1826 (1985).

Scott, J.R., et al., "Homologous Regions within M Protein Genes in Group A Streptococci of Different Serotypes," *Infec. and Immun. 52:*609–612 (1986).

Stålhammar–Carlemalm, M., et al., "Protein Rib: A Novel Group B Streptococcal Cell Surface Protein that Confers Protective Immunity and Is Expressed by Most Strains Causing Invasive Infections," *J. Exp. Med. 177:*1593–1603 (1993).

Tabor, S., "DNA Ligases," in: *Current Protocols in Molecular Biology,* vol. 1, Ausubel, F.M., et al., eds., John Wiley & Sons Inc., New York, p. 3.14.1–3.14.4 (1994).

Valtonen, M.V., et al. "Isolation of a C (Ibc) protein from group B Streptococcus which elicits mouse protective antibody," *Microb. Path. 1:*191–204 (1986).

Vieira, J. and J. Messing, "The pUC plasmids, an M13mp7–derived system for insertion mutagenesis and sequencing with synthetic universal primers," *Gene 19:*259–268 (1982).

Wagner, B., et al., "Immunoelectron Microscopic Study of the Location of Group–Specific and Protein Type–Specific Antigens of Group B Streptococci," *J. Gen. Microbiol. 118:*95–105 (1980).

Wanger, A.R. and G.M Dunny, "Development of a system for genetic and molecular analysis of *Streptococcus agalactiae,*" *Res. Vet. Sci. 38:*202–208 (1985).

Wanger, A.R. and G.M Dunny, "Identification of a *Streptococcus agalactiae* Protein Antigen Associated with Bovine Mastitis Isolates," *Infec and Immun. 55:*1170–1175 (1987).

Ward, J. and S. Cochi, "*Haemophilus influenzae* Vaccines," in: *Vaccines,* Plotkin, S.A. and E.A. Mortimer, Jr., eds., W.B. Saunders, Philadelphia, pp. 300–332 (1988).

Wästfelt, M., et al., "Identification of a Family of Streptococcal Surface Proteins with Extremely Repetitive Structure," *J. Biol. Chem. 271:*18892–18897 (Aug. 1996).

Weis, J.H., "Plating and Transferring Cosmid and Plasmid Libraries," in: *Current Protocols in Molecular Biology,* vol. 1, Ausubel, F.M., et al., eds., John Wiley & Sons, Inc., New York, pp. 6.2.1–6.2.3 (1994).

Weiser, J.N., and Rubens, C.E., "Transposon Mutagenesis of Group B Streptococcus Beta–Hemolysin Biosynthesis," *Infec. and Immun. 55:*2314–2316 (1987).

Wessels, M.R. and D.L Kasper, "Molecular Size Affects Antigenicity of Type III, Group B Streptococcus Capsular Polysaccharide," *Trans. Assoc. Amer. Phys. 98:*384–391 (1985).

Wessels, M.R., et al., "Stimulation of Protective Antibodies against Type Ia and Ib Group B Streptococci by a Type Ia Polysaccharide–Tetanus Toxoid Conjugate Vaccine," *Infect. and Immun. 61:*4760–4766 (1993).

Wilkinson, H.W. and M.D. Moody, "Serological Relationships of Type I Antigens of Group B Streptococci," *J. Bacteriol. 97:*629–634 (1969).

Wilkinson, H.W. and R.G. Eagon, "Type–Specific Antigens of Group B Type Ic Streptococci," *Infec. and Immun. 4:*596–604 (1971).

Wong, W.W., et al., "Rapid Purification of the Human C3b/C4b Receptor (CR1) by Monoclonal Antibody Affinity Chromatography," *J. Immunol. Methods 82:*303–313 (1985).

Wren, B.W., "A family of clostridial and streptococcal ligand–binding proteins with conserved C–terminal repeat sequences," *Mol. Microbiol. 5:*797–803 (1991).

Zink, G.L., "Immunizing Agents and Diagnostic Antigens," in *Pharmaceutical Sciences*, Mack Publishing Company, Easton, Pennsylvania, pp. 1324–1340 (1980).

Zurawski, V.R., et al., "Antibodies of Restricted Heterogeneity Directed Against the Cardiac Glycoside Digoxin," *J. Immunol. 121:*122–129 (1978).

English language abstract of EP 0 071 515 A1, Derwent World Patents Index (Dialog File 351), WPI Accession No. 83–15419K.

English language abstract of EP 0 206 852 A1, Derwent World Patents Index (Dialog File 351), WPI Accession No. 86–341137.

GENBANK Accession No. U33554 downloaded on Feb. 12, 1997 (originally submitted on Aug. 10, 1995 and updated on Feb. 11, 1996) having sequence of the terminal portion of the epsilon antigen.

* cited by examiner

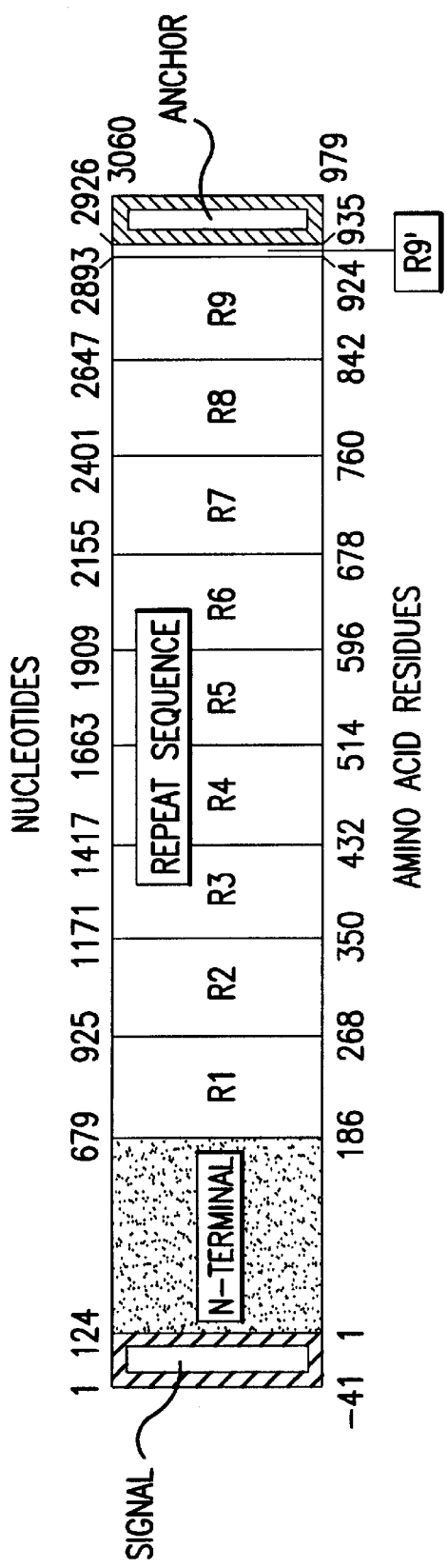
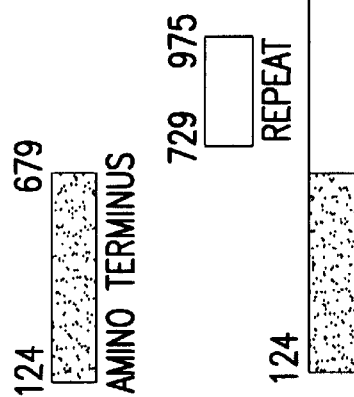
FIG.1A
FIG.1B

```
  1  CCAAATATGA TTCAAAAAAT CGAAAAAGTC AAATTATATA TATAAAAAAA

51  AGCAGATTAG ATTAGATAAA AAAGTATAGA TATTCTAATA TTGTTGTTTA
           -10                                RBS      Signal Seq.
101  AGCCTATAAT TTACTCTGTA TAGAGTTATA CAGAGTAAAG GAGAATATTA

151  TGTTTAGAAG GTCTAAAAAT AACAGTTATG ATACTTCACA GACGAAACAA

201  CGGTTTTCAA TTAAGAAGTT CAAGTTTGGT GCAGCTTCTG TACTAATTGG

251  TATTAGTTTT TTAGGAGGTT TTACTCAAGG GCAATTTAAT ATTTCTACAG
                                    Mature Protein
301  ATACTGTGTT TGCAGCTGAG GTGATTTCAG GAAGTGCTGC TGCTACATTA 351  AATTCCGCTT TAGTAAAAAA TGTATCTGGT GGAAAAGCGT ATATAGAtAT 401  ATATGATGTT AAAAATGGaA AAATAGATCC TTTAAACTTA ATTGTTTTAC 451  CCCCTTCTAA TTATTCAGCA AACTATTATA TAAAaCAAGG TGGAAGGATT

501  TTCACGAGTG TTAATCAACT TCAAACACCA GGTACAGCTA CTATTACGTA

551  CAACATCCTT GATGAAAATG GAAATCCTTA TACTAAAAGT GATGGTCAAA

601  TAGATATTGT AAGTCTTGTA ACAACAGATA TGATACTACA GAATAAGGAT

651  AATATCAACA AAGTAATTGA AAATGCAAAT GATCCTAAAT GGAGCGATGA

701  TAGTCGAAAA GATGTACTGA GCAAGATAGA AGTTATAAAA AATGATATT
```

FIG.6A

```
     Signal Peptide
  1  MFRRSKNNSY DTSQTKQRFS IKKFKFGAAS VLIGISFLGG FTQGQFNIST
           Mature Peptide
 51  DTVFAAEVIS GSAAATLNSA LVKNVSGGKA YIDIYDVKNG KIDPLNLIVL

101  PPSNYSANYY IKQGGRIFTS VNQLQTPGTA TITYNILDEN GNPYTKSDGQ

151  IDIVSLVTTD MILQNKDNIN KVIENANDPK WSDDSRKDVL SKIEVIKNDI
```

FIG.6B

```
100  AAGCCTATAATTTACTCTGTATAGAGTTATACAGAGTAAAGGAGAATATT         149 Epsilon
     ||||||||||||||||||||||||||||||||||||||||||||||||||
427  AAGCCTATAATTTACTCTGTATAGAGTTATACAGAGTAAAGGAGAATATT         476 Alpha
     Signal Sequence
150  ATGTTTAGAAGGTCTAAAAATAACAGTTATGATACTTCACAGACGAAACA         199 Epsilon
     ||||||||||||||||||||||||||||||||||||||||||||||||||
477  ATGTTTAGAAGGTCTAAAAATAACAGTTATGATACTTCACAGACGAAACA         526 Alpha 200  ACGGTTTTCAATTAAGAAGTTCAAGTTTGGTGCAGCTTCTGTACTAATTG         249 Epsilon
     ||||||||||||||||||||||||||||||||||||||||||||||||||
527  ACGGTTTTCAATTAAGAAGTTCAAGTTTGGTGCAGCTTCTGTACTAATTG         576 Alpha 250  GTATTAGTTTTTTAGGAGGTTTTACTCAAGGGCAATTTAATATTTCTACA         299 Epsilon
     ||| ||||||||| || || |||| |||||| | ||||||||||   |  |
577  GTCTTAGTTTTTTGGGTGGGGTTACACAAGGTAATCTTAATATTTTTGAA         626 Alpha
                          . Amino Terminus
300  GATACTGTGTTTGCAGCTGAGGTGATTTCAGGAAGtgcTGCTGCTACATT         349 Epsilon
     ||  |  |  ||||| ||   |||  ||||  |    |||  |  |  ||
627  GAGTCAATAGTTGCTGCATCTACAATTCCAGGGAG...TGCAGCGACCTT         673 Alpha 350  AAATTCCGCTTTAGTAAAAAATGTATCTGGTGGAAAAGCGTATATAGAtA         399 Epsilon
     ||||  |   |  |||||| ||  |||||| || || ||||| ||||||
674  AAATACAAGCATCACTAAAAATATACAAAACGGAAATGCTTACATAGATT         723 Alpha 400  TATATgATGTTAAAAATGGaAAAATAGATCCTTTAAACTTAATTGTTTTA         449 Epsilon
     ||||||||||  |||  ||  ||||||||||| |||| ||||||||||||
724  TATATGATGTAAAATTAGGTAAAATAGATCCATTACAATTAATTGTTTTA         773 Alpha 450  CCCCCTTCTAATTATTCAGCAAaCTATTATATAAAaCAAGGTGGAAGGAT         499 Epsilon
       |   |||  ||||||| ||| |  |  |  ||||||| |
774  GAAC...AAGGTTTTACAGCAAAGTATGTTTTTAGACAAGGTACTAAATA         820 Alpha 500  TTTCACGAGTGTTAATCAACTTCAAACACCAGGTACAGCTACTATTACGT         549 Epsilon
      |  |  ||||  |||  |||  |  |  ||||  |  ||||  |||| |
821  CTATGGGGATGTTTCTCAGTTGCAGAGTACAGGAAGGGCTAGTCTTACCT         870 Alpha 550  ACAACATCCTTgATGAAAATGGAAATCCTTATACTAAAAGTGATGGTCAA         599 Epsilon
     ||||  |    |||  ||||| ||   ||  || |  ||||| ||| |||
871  ATAATATATTTGGTGAAGATGGACTACCACATGTAAAGACTGATGGACAA         920 Alpha 600  ATAGATATTGTAAGTCTTGTAACAAC.AGATATGATACTACAGAAT...AA         646 Epsilon
     || |||||  || || ||| | |||| ||| ||||   |   ||    |
921  ATTGATATAGTTAGTGTTGCTTTAACTATTTATGATTCAACAACCTTGAG         970 Alpha 647  GGATAATATCAACAAAGTAATTGAAAATGCAAATGATCCTAAATGGAGCG         696 Epsilon
     ||||| || |  | ||||   ||||| ||||| |||||| ||| ||| ||
971  GGATAAGATTGAAGAAGTTAGAACGAATGCAAACGATCCTAAGTGGACGG         1020 Alpha
```

FIG.7

```
                        SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
           (A) LENGTH: 30 base pairs
           (B) TYPE: nucleic acid
           (C) STRANDEDNESS: both
           (D) TOPOLOGY: linear (ii) MOLECULE TYPE: cDNA (xi) SEQUENCE DESCRIPTION: SEQ ID NO:1:

CAGAATTCAA TCAATCATAT GAGTTACCAC                                         30

(2) INFORMATION FOR SEQ ID NO:2:

(i) SEQUENCE CHARACTERISTICS:
           (A) LENGTH: 30 base pairs
           (B) TYPE: nucleic acid
           (C) STRANDEDNESS: both
           (D) TOPOLOGY: linear (ii) MOLECULE TYPE: cDNA (xi) SEQUENCE DESCRIPTION: SEQ ID NO:2:

TGTTGGATCC TATTTATCTT TATCCGGTAC                                         30

(2) INFORMATION FOR SEQ ID NO:3:

(i) SEQUENCE CHARACTERISTICS:
           (A) LENGTH: 749 base pairs
           (B) TYPE: nucleic acid
           (C) STRANDEDNESS: both
           (D) TOPOLOGY: both (ii) MOLECULE TYPE: cDNA (ix) FEATURE:
           (A) NAME/KEY: CDS
           (B) LOCATION: 150..749

(ix) FEATURE:
           (A) NAME/KEY: sig_peptide
           (B) LOCATION: 150..320

(ix) FEATURE:
```

(A) NAME/KEY: mat_peptide
        (B) LOCATION: 321..749

(xi) SEQUENCE DESCRIPTION: SEQ ID NO:3:

CCAAATATGA TTCAAAAAAT CGAAAAAGTC AAATTATATA TATAAAAAAA AGCAGATTAG          60

ATTAGATAAA AAAGTATAGA TATTCTAATA TTGTTGTTTA AGCCTATAAT TTACTCTGTA         120

TAGAGTTATA CAGAGTAAAG GAGAATATT ATG TTT AGA AGG TCT AAA AAT AAC          173
                                 Met Phe Arg Arg Ser Lys Asn Asn
                                 -57     -55             Lys Asn
                                                                 -50

AGT TAT GAT ACT TCA CAG ACG AAA CAA CGG TTT TCA ATT AAG AAG TTC          221
Ser Tyr Asp Thr Ser Gln Thr Lys Gln Arg Phe Ser Ile Lys Lys Phe
            -45                 -40                     -35

AAG TTT GGT GCA GCT TCT GTA CTA ATT GGT ATT AGT TTT TTA GGA GGT          269
Lys Phe Gly Ala Ala Ser Val Leu Ile Gly Ile Ser Phe Leu Gly Gly
        -30                 -25                 -20

TTT ACT CAA GGG CAA TTT AAT ATT TCT ACA GAT ACT GTG TTT GCA GCT          317
Phe Thr Gln Gly Gln Phe Asn Ile Ser Thr Asp Thr Val Phe Ala Ala
        -15                 -10                 -5

GAG GTG ATT TCA GGA AGT GCT GCT GCT ACA TTA AAT TCC GCT TTA GTA          365
Glu Val Ile Ser Gly Ser Ala Ala Ala Thr Leu Asn Ser Ala Leu Val
 1                   5                  10                  15

AAA AAT GTA TCT GGT GGA AAA GCG TAT ATA GAT ATA TAT GAT GTT AAA          413
Lys Asn Val Ser Gly Gly Lys Ala Tyr Ile Asp Ile Tyr Asp Val Lys
                20                  25                  30

AAT GGA AAA ATA GAT CCT TTA AAC TTA ATT GTT TTA CCC CCT TCT AAT          461
Asn Gly Lys Ile Asp Pro Leu Asn Leu Ile Val Leu Pro Pro Ser Asn
            35                  40                  45

TAT TCA GCA AAC TAT TAT ATA AAA CAA GGT GGA AGG ATT TTC ACG AGT          509
Tyr Ser Ala Asn Tyr Tyr Ile Lys Gln Gly Gly Arg Ile Phe Thr Ser
        50                  55                  60

GTT AAT CAA CTT CAA ACA CCA GGT ACA GCT ACT ATT ACG TAC AAC ATC          557
Val Asn Gln Leu Gln Thr Pro Gly Thr Ala Thr Ile Thr Tyr Asn Ile
    65                  70                  75

CTT GAT GAA AAT GGA AAT CCT TAT ACT AAA AGT GAT GGT CAA ATA GAT          605
Leu Asp Glu Asn Gly Asn Pro Tyr Thr Lys Ser Asp Gly Gln Ile Asp
 80                  85                  90                  95

ATT GTA AGT CTT GTA ACA ACA GAT ATG ATA CTA CAG AAT AAG GAT AAT          653
Ile Val Ser Leu Val Thr Thr Asp Met Ile Leu Gln Asn Lys Asp Asn
                100                 105                 110

ATC AAC AAA GTA ATT GAA AAT GCA AAT GAT CCT AAA TGG AGC GAT GAT          701
Ile Asn Lys Val Ile Glu Asn Ala Asn Asp Pro Lys Trp Ser Asp Asp
            115                 120                 125

AGT CGA AAA GAT GTA CTG AGC AAG ATA GAA GTT ATA AAA AAT GAT ATT          749
Ser Arg Lys Asp Val Leu Ser Lys Ile Glu Val Ile Lys Asn Asp Ile
        130                 135                 140

(2) INFORMATION FOR SEQ ID NO:4:

(i) SEQUENCE CHARACTERISTICS:
        (A) LENGTH: 200 amino acids
        (B) TYPE: amino acid
        (D) TOPOLOGY: linear (ii) MOLECULE TYPE: protein (xi) SEQUENCE DESCRIPTION: SEQ ID NO:4:

Met Phe Arg Arg Ser Lys Asn Asn Ser Tyr Asp Thr Ser Gln Thr Lys
-57     -55             -50                 -45

Gln Arg Phe Ser Ile Lys Lys Phe Lys Phe Gly Ala Ala Ser Val Leu
    -40                 -35             -30

```
Ile Gly Ile Ser Phe Leu Gly Gly Phe Thr Gln Gly Gln Phe Asn Ile
-25                 -20                 -15                 -10

Ser Thr Asp Thr Val Phe Ala Ala Glu Val Ile Ser Gly Ser Ala Ala
                 -5                   1                   5

Ala Thr Leu Asn Ser Ala Leu Val Lys Asn Val Ser Gly Gly Lys Ala
             10                  15                  20

Tyr Ile Asp Ile Tyr Asp Val Lys Asn Gly Lys Ile Asp Pro Leu Asn
         25                  30                  35

Leu Ile Val Leu Pro Pro Ser Asn Tyr Ser Ala Asn Tyr Tyr Ile Lys
 40                  45                  50                  55

Gln Gly Gly Arg Ile Phe Thr Ser Val Asn Gln Leu Gln Thr Pro Gly
                 60                  65                  70

Thr Ala Thr Ile Thr Tyr Asn Ile Leu Asp Glu Asn Gly Asn Pro Tyr
             75                  80                  85

Thr Lys Ser Asp Gly Gln Ile Asp Ile Val Ser Leu Val Thr Thr Asp
         90                  95                 100

Met Ile Leu Gln Asn Lys Asp Asn Ile Asn Lys Val Ile Glu Asn Ala
    105                 110                 115

Asn Asp Pro Lys Trp Ser Asp Ser Arg Lys Asp Val Leu Ser Lys
120                 125                 130                 135

Ile Glu Val Ile Lys Asn Asp Ile
                140
```

(2) INFORMATION FOR SEQ ID NO:5:

(i) SEQUENCE CHARACTERISTICS:
        (A) LENGTH: 597 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:5:

```
AAGCCTATAA TTTACTCTGT ATAGAGTTAT ACAGAGTAAA GGAGAATATT ATGTTTAGAA    60

GGTCTAAAAA TAACAGTTAT GATACTTCAC AGACGAAACA ACGGTTTTCA ATTAAGAAGT   120

TCAAGTTTGG TGCAGCTTCT GTACTAATTG GTATTAGTTT TTTAGGAGGT TTTACTCAAG   180

GGCAATTTAA TATTTCTACA GATACTGTGT TTGCAGCTGA GGTGATTTCA GGAAGTGCTG   240

CTGCTACATT AAATTCCGCT TTAGTAAAAA ATGTATCTGG TGGAAAAGCG TATATAGATA   300

TATATGATGT TAAAAATGGA AAAATAGATC CTTTAAACTT AATTGTTTTA CCCCCTTCTA   360

ATTATTCAGC AAACTATTAT ATAAAACAAG GTGGAAGGAT TTTCACGAGT GTTAATCAAC   420

TTCAAACACC AGGTACAGCT ACTATTACGT ACAACATCCT TGATGAAAAT GGAAATCCTT   480

ATACTAAAAG TGATGGTCAA ATAGATATTG TAAGTCTTGT AACAACAGAT ATGATACTAC   540

AGAATAAGGA TAATATCAAC AAAGTAATTG AAAATGCAAA TGATCCTAAA TGGAGCG      597
```

(2) INFORMATION FOR SEQ ID NO:6:

(i) SEQUENCE CHARACTERISTICS:
        (A) LENGTH: 594 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:6:

| | | |
|---|---|---|
| AAGCCTATAA TTTACTCTGT ATAGAGTTAT ACAGAGTAAA GGAGAATATT ATGTTTAGAA | 60 | |
| GGTCTAAAAA TAACAGTTAT GATACTTCAC AGACGAAACA ACGGTTTTCA ATTAAGAAGT | 120 | |
| TCAAGTTTGG TGCAGCTTCT GTACTAATTG GTCTTAGTTT TTTGGGTGGG GTTACACAAG | 180 | |
| GTAATCTTAA TATTTTTGAA GAGTCAATAG TTGCTGCATC TACAATTCCA GGGAGTGCAG | 240 | |
| CGACCTTAAA TACAAGCATC ACTAAAAATA TACAAAACGG AAATGCTTAC ATAGATTTAT | 300 | |
| ATGATGTAAA ATTAGGTAAA ATAGATCCAT TACAATTAAT TGTTTTAGAA CAAGGTTTTA | 360 | |
| CAGCAAAGTA TGTTTTTAGA CAAGGTACTA AATACTATGG GGATGTTTCT CAGTTGCAGA | 420 | |
| GTACAGGAAG GGCTAGTCTT ACCTATAATA TATTTGGTGA AGATGGACTA CCACATGTAA | 480 | |
| AGACTGATGG ACAAATTGAT ATAGTTAGTG TTGCTTTAAC TATTTATGAT TCAACAACCT | 540 | |
| TGAGGGATAA GATTGAAGAA GTTAGAACGA ATGCAAACGA TCCTAAGTGG ACGG | 594 | |

(2) INFORMATION FOR SEQ ID NO:7:

(i) SEQUENCE CHARACTERISTICS:
        (A) LENGTH: 15 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:7:

| | |
|---|---|
| GATCCATTGT GCTGG | 15 |

(2) INFORMATION FOR SEQ ID NO:8:

(i) SEQUENCE CHARACTERISTICS:
        (A) LENGTH: 11 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:8:

| | |
|---|---|
| GTAACACGAC C | 11 |

(2) INFORMATION FOR SEQ ID NO:9:

(i) SEQUENCE CHARACTERISTICS:
        (A) LENGTH: 12 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:9:

| | |
|---|---|
| ACACGAGATT TC | 12 |

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:10:

| | |
|---|---|
| GTATATGGAT CCATAGTTGC TGCATCTACA | 30 |

```
(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:11:

GGGCTGAAGC TTCAATACTA ACAATTTCTC                                    30

(2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:12:

GTATATGGAT CCAAAGCTCA GCAAGTCAAC                                    30

(2) INFORMATION FOR SEQ ID NO:13:

(i) SEQUENCE CHARACTERISTICS:
        (A) LENGTH: 33 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:13:

GGGCTGAAGC TTATCCTCTT TTTTCTTAGA AAC                                33
```

GROUP B STREPTOCOCCUS VACCINE

This application claims the benefit of the filing date of U.S. Provisional Application No. 60/039,353, filed Mar. 19, 1997 and incorporates said application herein by reference.

GOVERNMENT SUPPORT

Part of the work performed during development of the invention utilized U.S. Government funds. Therefore, the U.S. Government may have certain rights in this invention.

FIELD OF THE INVENTION

The invention relates to the fields of microbiology and vaccine technology, and concerns the development of vaccines capable of conferring immunity to infection by group B Streptococcus.

BACKGROUND OF THE INVENTION

*Streptococcus agalactiae* (GBS) is the leading cause of neonatal sepsis and early onset meningitis in infants in the United States, causing over 2,000 deaths each year. Thus GBS is an important disease pathogen. GBS is also responsible for more than 50,000 cases of maternal postpartum endometritis (Baker, C., In: *Infectious Diseases of the Fetus and Newborn Infant*. Remington J., et al. eds. Philadelphia: W. B. Saunders, (1990), pp. 742–811). Recently, GBS has increasingly been seen to cause serious infections in non-pregnant adults, primarily among the inmmunocompromised, elderly individuals and diabetics. Invasive infection has been diagnosed in 4.4 per 100,000 nonpregnant adults, with a mortality rate of 21% (Farley; M. M., et al., *N. Engl. J Med* 328(25):1807–1811 (1993)). This prospective surveillance study documented an annual incidence of invasive GBS disease to be 9.2 cases per 100,000 population. The incidence of invasive GBS infections in adults is higher than the incidence of infections caused by many other important pathogens, including the meningococci. Although GBS is sensitive to antibiotics, the rapid onset of the disease in neonates and infants also leads to high morbidity (50%) and mortality (20%) (Baker, C., In: *Infectious Diseases of the Fetus and Newborn Infant*. Remington J., et al. eds. Philadelphia: W. B. Saunders, (1990), pp. 742–811; Michel, J. L., *Infectious Disease Practice* 13:1–12 (1990)). Therefore, there is a need to develop vaccines capable of conferring immunity to infection by GBS.

The pathogenic streptococci express a number of surface-associated, opsonic, and protective polysaccharides and protein antigens (Kehoe, M. A., *Vaccine* 9:797–806 (1991); Lachenauer, C. S. & L. C. Madoff, *Infect. Immun.* 64:4255–4260 (1996)). The type-specific capsular polysaccharide by itself is not very immunogenic; however, antibodies to conjugates of the capsular polysaccharides and protein antigens elicit protection in animal models of GBS infections (Kasper, D., et al., in *Vaccines* 94, E. Norrby (ed.), Cold Spring Harbor Laboratory Press, Cold Spring Harbor, N.Y., (1994), pp. 113–117; Weis, J. H. in *Current Protocols in Molecular Biology*, Vol. 1, F. M., Ausubel, et al., (eds.), John Wiley & Sons, Inc., New York, (1994), pp. 6.2.1–6.2.3.; Paoletti, L. C., et al., *Infect. Immun.* 62:3236–3243 (1994); Wessels, M. R., et al., *Infect. Immun.* 61:4760–4766 (1993)).

GBS also expresses a family of protective and well-characterized protein antigens called C proteins (alpha and beta) and R protein (Rib), also known as R4 (Heden, L. et al., *Eur. J. Immunol.* 21:1481–1490 (1991); Jerlstrom, P. G., et al., *Mol. Microbiol.* 5:843–849 (1991); Larsson, C., et al., *Infect. Immun.* 64:3518–3523 (1996); Michel, J. L., et al., in *Genetics and Molecular Biology of Streptococci, Lactococci, and Enterococci*, G. M. Dunny, et al., (eds.), American Society for Microbiology, Washington, D.C., (1991), pp. 214–218; Michel, J. L., et al., *Infect. Immun.* 59:2023–2028 (1991); Michel, J. L., et al., *Proc. Natl. Acad. Sci. USA.* 89:10060–10064 (1992); Stålhammar-Carlemalm, M., et al., *J. Exp. Med.* 177:1593–1603 (1993); Wästfelt, M., et al., *J. Biol. Chem.* 271:18892–18897 (1996)). Recently an additional C-protein, the epsilon antigen was discovered (DuBois, N. B. Genetic and phenotypic properties of the surface proteins of group B Streptococcus and the identification of a new protein, Bachelor of Arts thesis in Biology, Harvard College, (1995)

The C proteins (alpha and beta, and epsilon) are surface-associated proteins on GBS carrying immunogenic epitopes that elicit protective antibodies. Antibodies raised against partially purified C proteins in rabbits were originally shown by Lancefield et al. to provide passive protection in mice against challenge with C protein-positive strains; C protein antibodies did not protect against C protein-negative strains (Lancefield, R. C., et al., *J. Exp. Med.* 142(1):165–179 (1975)). Strains bearing C proteins resist phagocytosis and inhibit intracellular killing (Payne, N. R, et al., *J. Infec. Dis.* 151:672–681 (1985)).

The C proteins have been divided into two species (Russel-Jones et al., *J. Exp. Med.* 160:1476–1484, 1984) that are independently expressed and antigenically distinct, and have been defined biochemically and immunologically. The alpha antigen is trypsin-resistant and has been shown to increase resistance to opsonophagocytic killing (Madoff et al., *Infect. Immun.* 59:2638–2644, 1991)), whereas the beta antigen is trypsin-sensitive, and binds preferentially to human serum IgA (Russel-Jones, G. J., *J. Exp. Med.* 160:1467–1475 (1984)) by a non-immune mechanism. Additionally, there is the epsilon antigen which is believed to be a member of the alpha antigen family. The specific biological roles of these proteins in virulence are not known.

The sequence of the alpha C-protein gene (bca) of GBS reveals four distinct domains: a signal sequence, an N-terminal region, a tandem repeat region, and a C-terminal anchor region (Michel, J. L., et al., *Proc. Natl. Acad. Sci. USA.* 89:10060–10064 (1992)). Presumably, the epsilon antigen gene (bce) has similar, though not necessarily identical domains. Identification and characterization of protective epitopes within the domains of the alpha, beta and epsilon C proteins will help determine the: immunological properties of these regions. These protective epitopes could be used to develop a C-protein-capsular polysaccharide conjugate vaccines to protect against a broad range of GBS strains.

The alpha antigen gene, bca, was previously cloned from the prototype Ia/C(α/β) strain A909. The antibodies raised to the cloned gene product were protective in an animal model (Michel, J. L. et al., *Inf. Immun.* 59:2023–2028 (1991)). In addition, the nucleotide sequence was determined and the derived animo acid sequence analyzed (Michel, J. L., et al., *Proc. Natl. Acad. Sci. USA.* 89:10060–10064 (1992)). The nucleotide sequence of alpha antigen revealed an open reading frame of 3,060 nucleotides encoding a precursor protein of 108.7 kilodaltons (kDa). The gene is composed of four distinct regions. Cleavage of a putative signal sequence of 56 amino acid yields a mature protein of 104.1 kDa. The 20.4 kDa N-terminal region shows no homology to previously described protein sequences and is followed by a series of nine tandem repeating units that make up 74% of the mature protein. The repeating units are identical, and each consists of 82 amino acids with a molecular mass of 8.7 kDa, which is encoded by 246 nucleotides. The C-terminal region of the alpha antigen contains a membrane anchor domain motif that is shared by a number of gram-positive surface-associated proteins (Michel, J. L., et al., *Proc. Natl. Acad. Sci. USA* 89(21):10060–10065 (1992)) including the group A streptococcal M proteins and the IgG-binding proteins of Staphylococcus (Fischetti, V., et al., *Mol. Microbiol.* 4:1603–1605, (1990); Wren, B. W., Mol Microbiol 5(4):797–803 (1991)). Immunoblot analysis of the native alpha antigen probed with either antisera to the cloned alpha antigen or an alpha antigen specific monoclonal antibody, 4G8, which binds to the repeat region, yields a regularly spaced ladder pattern of heterogeneous peptides. The bands are spaced at 8-kDa intervals, corresponding to the coding region defined by a single repeating subunit in the gene (Michel, J. L., et al., *Proc. Natl. Acad. Sci. USA* 89(21):10060–10065 (1992)). This correlation suggests that the repeat region is responsible for the laddered peptide heterogeneity of the alpha antigen.

It was reported that the size of the largest alpha antigen expressed by a given strain varies widely, from 54 to >200 kDa Opsonophagocytic killing in the presence of 4G8 antibodies correlated directly with increasing molecular mass of the alpha antigen and with the quantity of the alpha antigen expressed on the surface of GBS. GBS strains bearing the alpha antigen are resistant to killing by polymorphonuclear leukocytes in the absence of alpha antigen specific antibody. However, this resistance is not dependent on the overall size of the antigen expressed by a given strain. While a given strain produces an alpha antigen with a consistent size distribution, occasional colonies are isolated expressing smaller protein sizes; this phenomenon has also been observed in strain pairs from mothers and infants (Hervas, J. A. et al., *Clin. Infect. Dis.* 16:714–718 (1993)) In recent work, it was found that immune mice infected with GBS bearing the alpha antigen yielded strains with either smaller or absent alpha antigen expression (Beseth, B. D., A genetic analysis of phenotypic diversity of the C protein alpha antigen of group B Streptococcus, Bachelor of Arts thesis in Biology, Harvard College, (1992); Madoff, L. C., et al., *Proc. Natl. Acad. Sci. USA*. 93:4131–4136 (1996)).

To explore the molecular basis for the smaller size of alpha antigen seen in different strains of GBS, a panel of GBS isolates was examined and the size of the alpha antigen was compared with the size and composition of the alpha antigen gene. In doing so, it was discovered that the alpha antigen gene family was, in fact, composed of at least two different but related proteins. The new class of proteins has been named epsilon. The N-terminal region of the epsilon gene (bce), has been cloned and the nucleotide sequence analyzed. The molecular basis for size variation among alpha and epsilon bearing strains of GBS, and their potential for multiple intramolecular regions of antigenic variability, is potentially important both in understanding mechanisms of pathogenesis of GBS and in the development of a conjugate vaccine against GBS.

Development of an effective C-protein-based conjugate vaccine is assisted by a better understanding of the immunogenic and protection inducing effect of the alpha and epsilon antigens, particularly since the alpha antigen appears to undergo antigenic variation in isolates from neonates and their mothers (Hervas, J. A., et al., *Clin. Infect. Dis.* 16:714–718 (1993); Madoff, L. C., et al., *Proc. Natl. Acad. Sci. USA*. 93:4131–4136 (1996)). Deletions in the number of tandem repeats within the bca (Gravekamp, C., et al., *Infect. Immun.* 64:3576–3583 (1996) and the bce gene may give rise to antigenically variable polypeptides due to conformational epitopes that vary as a function of the number of repeats of the bce gene.

If an effective conjugate GBS vaccine is to be developed, protective epitopes that are conserved in the parental strains and their deletion mutants need to be identified. It has been observed that the bca gene was deleted in the neonatal isolates in the tandem repeat region but not in the N- and C-termini of the bca gene (Beseth, B. D., A genetic analysis of phenotypic diversity of the C protein alpha antigen of group B Streptococcus, Bachelor of Arts thesis in Biology, Harvard College, (1992); Madoff, L. C., et al., *Proc. Natl. Acad. Sci. USA*. 93:4131–4136 (1996)). Therefore, conserved epitopes are likely to be localized to the N- and C-terminal regions. The N-terminus of the alpha and epsilon C protein is a likely location for protective epitopes of these C-proteins that are conserved in spontaneous deletions and wild-type strains. However, the C-terminus of the alpha C protein may not contain protective epitopes, since it is thought to be involved in the antigen's attachment to the cell-wall peptidoglycan (Michel, J. L., et al., *Proc. Natl. Acad. Sci. USA*. 89:10060–10064 (1992); Navarre, W. W. & Schneewind, O., *Mol. Microbiol.* 14:115–121 (1 994); Schneewind, O., et al., *EMBO J.* 12:4803–4811 (1993)).

SUMMARY OF THE INVENTION

The present invention concerns the development of a conjugate vaccine to group B Streptococcus (i.e. Streptococcus agalactiae) that utilizes the N-terminal region of the epsilon antigen or fragments thereof.

This novel conjugate vaccine should have the advantages both of eliciting T-cell dependent protection via the adjuvant action of the carrier protein and also providing additional protective epitopes that are present on the group B streptococcal protein (Insel, R. A, et al., *New Eng. J. Med.* (Editorial) 319(18):1219–1220 (1988); Baker, C. J, et al., *Rev. of Infec. Dis.* 7:458467 (1985)).

The advantage to use of the N-terminal region of the epsilon antigen in the vaccine is that the N-terminal is a likely location for protective epitopes of the epsilon antigen that are conserved in spontaneous deletions and wild-type strains. Further, the N-terminal region of the C-proteins may be more genetically stable than other regions of the molecule. The repeat regions of other C-proteins are known to contain antigenic epitotpes but also exhibit antigenic variability. (Klinge, et al., *Infect. Immun.* (April 1997, In press)).

In detail, the invention provides a conjugate vaccine capable of conferring host immunity to an infection by group B Streptococcus, the vaccine comprising (a) a polysaccharide conjugated to (b) a protein; wherein both the polysaccharide and the protein are characteristic molecules of the group B Streptococcus, and wherein the protein is a derivative of the C protein epsilon antigen N-terminal region that retains the ability to elicit protective antibodies against the group B Streptococcus.

The conjugate vaccine of the invention, can include the N-terminal region of the epsilon antigen or fragment thereof as the antigen in the vaccine plus the alpha and/or beta antigen or fragments thereof in combination with the epsilon antigen. These conjugate vaccines may also be used to obtain the passive vaccines of the invention.

The vaccine of the invention may also comprise the N-terminal region of the epsilon antigen or fragments thereof as the antigen in the vaccine either by itself or with the alpha and/or beta antigen or fragments thereof in combination with the epsilon antigen. Such fragments or combinations of fragments may be used in the vaccine of the invention in a non-conjugated form, i.e. not conjugated to a polysaccharide. These vaccines may also be used to obtain the passive vaccines of the invention.

The invention also concerns a method for preventing or attenuating an infection caused by a group B Streptococcus which comprises administering to an individual, suspected of being at risk for such an infection, an effective amount of the conjugate vaccine of the invention, such that it provides host immunity against the infection.

The invention further concerns a method for preventing or attenuating infection caused by a group B Streptococcus which comprises administering to a pregnant female an effective amount of a conjugate vaccine of the invention, such that it provides immunity to the infection to an unborn offspring of the female.

The invention also provides a method for preventing or attenuating an infection caused by a group B Streptococcus which comprises administering to an individual suspected of being at risk for such an infection an effective amount of an antisera elicited from the exposure of a second individual to a conjugate vaccine of the invention, such that it provides host immunity to the infection.

The invention also provides for the use of the N-terminal region of the epsilon antigen as an immunogenic composition and for use of such a composition in diagnostic procedures.

The invention also provides for a plasmid (ATCC Accession No. 98365, deposited Mar. 18, 1997 at The American, Type Culture Collection, Rockville, Md.) containing the N-terminal region of the epsilon antigen. The plasmid is referred to as pJMS36.

BRIEF DESCRIPTION OF THE FIGURES

FIGS. 1A–1C. Map of the C protein alpha antigen structural gene and nucleotide probes. The map of the alpha C-protein (FIG. 1A) indicates the signal sequence, the amino terminus, the nine repeating subunits, and the carboxyl terminal anchor region. The nucleotide residues are indicated above the map and the amino acid residues of the mature protein below. Restriction sites (FIG. 1B) within the gene and the flanking regions are indicated. The nucleotide probes (FIG. 1C) used for genetic analysis are shown below the map. The amino terminus probe is a PCR product, the repeat probe is digested with StyI, and the whole gene probe is digested with HindIII. The composite gene at the top of FIG. 1C depicts the signal sequence, N-terminal, repeat region and C-terminal of gene bca as well as flanking sequence; abbreviations for restriction endonucleases A, AseI; B, BsaBI; D DraI; H, HincII; I, NsiI; M, MspI; N, NdeI; S, StyI.

(FIG. 2A) Correlation of the molecular mass of expressed alpha antigen with the size of its structural gene. The maximal sizes of the alpha antigen from 18 strains of GBS were determined by western blot and compared with the sizes of the structural gene defined by DraI and detected on genomic Southern blots. The correlation coefficient for this relationship is 0.91. (FIG. 2B) Correlation of alpha antigen gene size with repeat region size. The size of the structural gene (DraI) on Southern blots was compared with the size of the repeat region defined by BsaBI genomic Southern blots. The correlation coefficient for this relationship is 0.96. (FIG. 2C) Divergence of two populations of GBS alpha antigens. Southern blot mapping of the structural gene, bca, in 18 clinical isolates revealed two populations of alpha antigen-positive strains. The open boxes are alpha and the closed boxes are epsilon. The correlation coefficients for both alpha and epsilon are 0.99, and by multiple regression modeling, the difference in slope and intercept between these data sets is significant (p<0.001).

FIGS. 6A–6B. Nucleotide and amino acid sequences of the epsilon antigen. The nucleotide sequence (FIG. 6A) (SEQ. ID. NO. 3) of the cloned amino terminus of epsilon was determined and translated to give the amino acid sequence (FIG. 6B) (SEQ. ID. NO. 4). Structural features of the gene are indicated, as well as the −10 promoter consensus sequence and the ribosomal binding site (RBS).

FIG. 7. Divergence of the alpha and epsilon antigen amino termini. The nucleotide sequence of epsilon (SEQ. ID. NO. 5) is compared to alpha (SEQ. ID. NO. 6), showing homology the upstream flanking DNA and the signal sequence. The amino termini, however, are distinct. Similar results are seen when the amino acid sequences are compared.

FIG. 9. Restriction maps of bca gene subclones, defining the location of monoclonal antibody 4G8 binding within the alpha C-protein. pJMS23-1 is the bca gene clone. pJMS23-9 was used to develop nested deletions of the bca gene (Michel, J. L., et al., *Proc. Natl. Acad. Sci.* 89:10060–10064 (1992)). pSKOF1-13 was derived from pJMS23-9 and contains part of the repeat region. pDEK14 encodes the alpha C-protein N-terminus and pDEK15 encodes the alpha C-protein C-terminus. The restriction endonuclease sites are A, AluI; N, NsiI; H, HindIII; and E, EcoRI. Promoters include Sp6 and T7, and His represents a six-residue histidine tag of vector pET24a.

FIG. 13A. Induction of expression and purification of the alpha C-protein N-terminal peptide. Lanes 1 and 2 show Coomassie-stained gels of extracts of E. coli containing pDEK14 before and after induction with IPTG, respectively. Lane 3 shows a 10-μg sample of the eluate from a lysate of E. coli containing pDEK14 after $Ni^{2+}$ affinity column chromatography. FIG. 13B. Detection of native alpha C-protein by antibodies to the gene product of pDEK14. Western blots are shown of extracts of GBS strains 090 (negative control, lane 1) and A909 (lane 2) probed with antibodies raised to the alpha C-protein N-terminus.

DETAILED DESCRIPTION OF THE PREFERRED EMBODIMENTS

Significance and Clinical Perspective

Figure 1C:
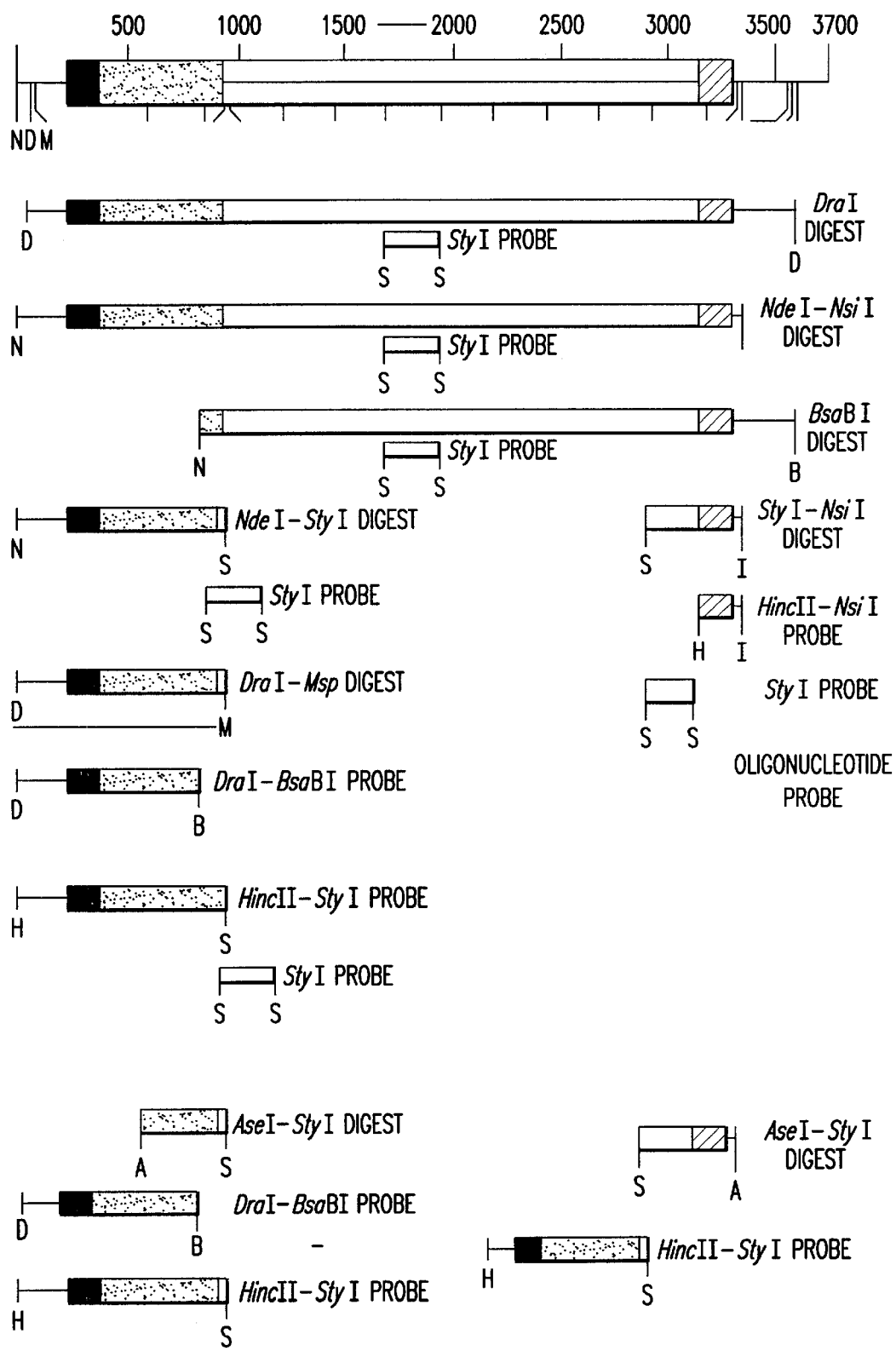

Maternal immunoprophylaxis with a vaccine to group B Streptococcus has been proposed as a potential route for protecting against infection both in the mother and in the young infant through the peripartum transfer of antibodies Baker, C. J. et al., New Eng. J. Med. (Editorial) 314(26):1702–1704 (1986); Baker, C. J. et al., New Eng. J. Med. 319:1180 (1988); Baker, C. J. et al., J. Infect. Dis. 7:458 (1985)). As is the case with other encapsulated bacteria, susceptibility to infection correlates with the absence of type-specific antibody (Kasper, D. L., et al., J. Clin. Invest. 72:260–269 (1983), Kasper, D. L., et al., Antibiot. Chemother. 35:90–100 (1985)). The lack of opsonically active type-specific anti-capsular antibodies to group B Streptococcus is a risk factor for the development of disease following colonization with group B Streptococcus (Kasper, D. L. et al., J. Infec. Dis. 153:407415 (1986)).

One approach has been to vaccinate with purified type-specific capsular polysaccharides. Methods of producing such vaccines, and the use of such vaccines to immunize against group B Streptococcus are disclosed by Kasper, D. L. (U.S. Pat. No. 4,207,414 and U.S. Reissue Patent RE31672, and U.S. Pat. Nos. 4,324,887, 4,356,263, 4,367,221, 4,367,222, and 4,367,223), by Carlo, D. J. (U.S. Pat. No. 4,413,057, European Patent Publication 38,265), and by Yavordios, D. et al. (European Patent Publication 71,515), all of which references are incorporated herein by reference.

Although the polysaccharide capsule of group B Streptococcus is well characterized and has been shown to play a role in both virulence and immunity (Kasper, D. L. J. Infect. Dis. 153:407 (1986)), these capsular components have been found to vary in their immunogenicity depending both on the specific capsular type and on factors in the host's immune system (Baker, C. J, et al., Rev. of Infec. Dis. 7:458–467 (1985)). A clinical trial evaluating a capsular polysaccharide vaccine of group B Streptococcus showed an overall response rate of 63 % and indicated that such a vaccine was not optimally immunogenic (Baker C. J, et al., New Eng. J. Med. 319(18):118–1185 (1988)).

Differences in immunogenicity have also been observed with the capsular polysaccharides of other bacteria. For example, the vaccine against the type C meningococcal capsule is highly active while the group B meningococcal polysaccharide vaccine is not immunogenic (Kasper, D. L. et al., J. Infec. Dis. 153:407415 (1986)). T-cell independent functions of the host's immune system are often required for mounting an antibody response to polysaccharide antigens. The lack of a T-cell independent response to polysaccharide antigens may be responsible for the low levels of antibody against group B Streptococcus present in mothers whose children subsequently develop an infection with group B Streptococcus. In addition, children prior to 18 or 24 months of age have a poorly developed immune response to T-cell independent antigens.

Determinants of Virulence and Immunity in group B Streptococcus

There are at least nine serotypes of group B Streptococcus that share a common group specific polysaccharide antigen. However, antibody of the group antigen is not protective in animal models. Lancefield originally classified group B Streptococcus into four serotypes (Ia, Ib, II and III) using precipitin techniques. The composition and structure of the unique type-specific capsular polysaccharides for each of the serotypes was subsequently determined (Jennings, H. J, et al., Biochem. 22:1258–1264 (1983), Kasper, D. L. et al., J. Infec. Dis. 153:407–415 (1986), Wessels, M. R, et al., Trans. Assoc. Amer. Phys. 98:384–391 (1985)). Wilkinson defined a fifth serotype, Ic, by the identification of a protein antigen (originally called the Ibc protein) present on all strains of serotype Ib and some strains with the type Ia capsule (Wilkinson, H. W, et al., J. Bacteriol. 97:629–634 (1969), Wilkinson, H. W, et al., Infec. and Immun. 4:596–604 (1971)). This protein was later found to vary in prevalence between the different serotypes of group B Streptococcus but was absent in serotype Ia (Johnson, D. R, et al., J. Clin. Microbiol. 19:506–510 (1984)).

The nomenclature, however, has been changed to classify the serotypes of group B Streptococcus solely by the capsular type-specific polysaccharides, with a fifth capsular type having been described (type IV) (Pritchard, D. G, et al., Rev. Infec. Dis. 10(8):5367–5371 (1988)) as well as a type V and VII (Lachaenauer et al., Inf. Immun. 64:42554260, (1996)). Therefore, the typing of group B Streptococcus strains is no longer based on the antigenic Ibc protein, which is now called the C protein. The type Ic strain is reclassified as serotype Ia on the basis of its capsular polysaccharide composition, with the additional information that it also carries the C protein.

Immunological, epidemiological and genetic data suggest that the type-specific capsule plays an important role in immunity to group B Streptococcus infections. The composition and structure of the type-specific capsular polysaccharides and their role in virulence and immunity have been the subjects of intensive investigation (Ferrieri, P. et al., *Infec. Immun.* 27:1023–1032 (1980), Krause, R. M, et al., *J. Exp. Med.* 142:165–179 (1975), Levy, N. J, et al., *J. Infec. Dis.* 149:851–860 (1984), Wagner, B, et al., *J. Gen. Microbiol.* 118:95–105 (1980), Wessels, M. R, et al., *Trans. Assoc. Amer. Phys.* 98:384–391 (1985)).

Controversy has existed regarding the structural arrangement of the type-specific and group B streptococcal polysaccharides on the cell surface, on the immunologically important determinants with in the type-specific polysaccharide, and on the mechanisms of capsule determined virulence of group B Streptococcus (Kasper, D. L. et al., *J. Infec. Dis.* 153:407–415 (1986)). To study the role of the capsule in virulence, Rubens et al. used transposon mutagenesis to create an isogeneic strain of type III group B Streptococcus that is unencapsulated (Rubens, C. E, et al., *Proc. Natl. Acad. Sci. USA* 84:7208–7212 (1987)). They demonstrated that the loss of capsule expression results in significant loss of virulence in a neonatal rat model. However, the virulence of clinical isolates with similar capsular composition varies widely. This suggests that other bacterial virulence factors, in addition to capsule, play a role in the pathogenesis of group B Streptococcus.

A number of proteins and other bacterial products have been described in group B Streptococcus whose roles in virulence and immunity have not been established, CAMP (Christine Atkins-Much Peterson) factor, pigment (probably carotenoid), R antigen, X antigen, anti-phagocytic factors and poorly defined "pulmonary toxins" (Ferrieri, P, et al., *J. Exp. Med.* 151:56–68 (1980); Ferrieri, P. et al., *Rev. Inf. Dis.* 10(2):1004–1071 (1988); Hill, H. R. et al., Sexually Transmitted Diseases, McGraw-Hill, pp. 397–407). The C proteins are discussed below.

Isogeneic strains of group B Streptococcus lacking hemolysin show no decrease in virulence in the neonatal rat model (Weiser, J. N, et al., *Infec. and Immun.* 55:2314–2316 (1987)). Both hemolysin and neuraminidase are not always present in clinical isolates associated with infection. The CAMP factor is an extracellular protein of group B Streptococcus with a molecule weight of 23,500 daltons that in the presence of staphylococcal beta-toxin (a sphingomyelinase) leads to the lysis of erythrocyte membranes. The gene for the CAMP factor in group B Streptococcus was recently cloned and expressed in *E. coli* (Schneewind, O, et al., *Infec. and Immun.* 56:2174–2179 (1988)). The role, if any, of the CAMP factor, X and R antigens, and other factors listed above in the pathogenesis of group B Streptococcus is not disclosed in the prior art (Fehrenbach, F. J, et al., In: *Bacterial Protein Toxins*, Gustav Fischer Verlag, Stuttgart (1988); Hill, H. R. et al., *Sexually Transmitted Diseases*, McGraw-Hill, N.Y., pp. 397407 (1984)).

The C protein(s) are a group of a cell surface associated protein antigens of group B Streptococcus that were originally extracted from group B Streptococcus by Wilkinson et al. (Wilkinson, H. W, et al., *J. Bacteriol.* 97:629–634 (1969), Wilkinson, H. W, et al., *Infec. and Immun.* 4:596–604 (1971)). They used hot hydrochloric acid (HCl) to extract the cell wall and trichloroacetic acid (TCA) to precipitate protein antigens. Two antigenically distinct populations of C proteins have been described: (1) A group of proteins that are sensitive to degradation by pepsin but not by trypsin, and called either TR (trypsin resistant) or alpha ($\alpha$). (2) Another group of group B Streptococcus proteins that are sensitive to degradation by both pepsin and trypsin, and called TS (trypsin sensitive) or beta ($\beta$) (Bevanger, L, et al., *Acta Path. Microbiol. Scand Sect. B*. 87:51–54 (1979), Bevanger, L, et al., *Acta Path. Microbiol. Scand. Sect. B*. 89:205–209 (1981), Bevanger, L. et al., *Acta Path. Microbiol. Scand. Sect. B*. 91:231–234 (1983), Bevanger, L. et al., *Acta Path. Microbiol. Scand. Sect. B*. 93:113–319 (1985), Bevanger, L, et al., *Acta Path. Microbiol. Immunol. Scand. Sect. B*. 93:121–124 (1985), Johnson, D. R, et al., *J. Clin. Microbiol.* 19:506–510 (1984), Russell-Jones, G. J, et al., *J. Exp. Med.* 160:1476–1484 (1984)).

In 1975, Lancefield et al. used mouse protection studies with antisera raised in rabbits to define the C proteins functionally for their ability to confer protective immunity against group B Streptococcus strains carrying similar protein antigens (Lancefield, R. C, et al., *J. Exp. Med.* 142:165–179 (1975)). Numerous investigators have obtained crude preparations of antigenic proteins from group B Streptococcus, that have been called C proteins, by chemical extraction from the cell wall using either HCl or detergents (Bevanger, L, et al., *Acta Path. Microbiol. Scand. Sect. B*. 89:205–209 (1981), Bevanger, L. et al., *Acta Path. Microbiol. Scand. Sect. B*. 93:113–119 (1985), Russell-Jones, G .J, et al., *J. Exp. Med.* 160:1476–1484 (1984), Valtonen, M. V, et al., *Microb. Path.* 1:191–204 (1986), Wilkinson, H. W, et al., *Infec. and Immun.* 4:596–604 (1971)). The reported sizes for these antigens have varied between 10 and 190 kilodaltons, and a single protein species has not been isolated or characterized (Ferrieri, P. et al., *Rev. Inf. Dis.* 10(2): 1004–1071 (1988)).

By screening with protective antisera, C proteins can be detected in about 60% of clinical isolates of group B Streptococcus, and are found in all serotypes but with differing frequencies (Johnson, D. R, et al., *J. Clin. Microbiol.* 19:506–510 (1984)). Individual group B Streptococcus isolates may have both the TR and TS antigens, or only one, or neither of these antigens. Except for the ability of the partially purified antigens to elicit protective immunity, the role of these antigens in pathogenesis has not been studied in vitro. In vivo studies with group B Streptococcus strains that carry C proteins provides some evidence that the C proteins may be responsible for resistance to opsonization (Payne, N. R, et al., *J. Infec. Dis.* 151:672–681 (1985)), and the C proteins may inhibit the intracellular killing of group B Streptococcus following phagocytosis (Payne, N. R, et al., *Infect. and Immun.* 55:1243–1251 (1987)). It has been shown that type II strains of group B Streptococcus carrying the C proteins are more virulent in the neonatal rat sepsis model (Ferrieri, P, et al., *Infect. Immun.* 27:1023–1032 (1980), Ferrieri, P. et al., *Rev. Inf. Dis.* 10(2): 1004–1071 (1988)). Since there is no genetic data on the C proteins, isogeneic strains lacking the C proteins have not previously been studied. There is evidence that one of the TS, or $\beta$, C proteins binds to IgA (Russell-Jones, G. J, et al., *J. Exp. Med.* 160: 1476–1484 (1984)). The role, if any, that the binding of IgA by the C proteins has on virulence is, however, not disclosed.

In 1986, Valtonen et al. isolated group B Streptococcus proteins from culture supernatants that elicit protection in the mouse model (Valtonen, M. V, et al., *Microb. Path.* 1:191–204 (1986)). They identified, and partially purified, a trypsin resistant group B Streptococcus protein with a molecular weight of 14,000 daltons. Antisera raised to this protein in rabbits protected mice against subsequent challenge with type Ib group B Streptococcus (89% protection). This protein is, by Lancefield's definition, a C protein. However, when antisera raised against this protein were used to immunoprecipitate extracts of group B Streptococcus antigens, a number of higher molecular weight proteins were found to be reactive. This suggested that the 14,000 m.w. protein may represent a common epitope of several group B Streptococcus proteins, or that it is a degradation product found in the supernatants of group B Streptococcus cultures. The diversity in the sizes in C proteins isolated from both the bacterial cells and supernatants suggests that the C proteins may represent a gene family, and maintain antigenic diversity as a mechanism for protection against the immune system.

The range of reported molecular weights and difficulties encountered in purifying individual C proteins are similar to the problems that many investigators have faced in isolating the M protein of group A Streptococcus (Dale, J. B, et al., *Infec. and Immun.* 46(1):267–269 (1984), Fischetti, V. A, et al., *J. Exp. Med.* 144:32–53 (1976), Fischetti, V. A, et al., *J. Exp. Med* 146:1108–1123 (1977)). The gene for the M protein has now been cloned and sequenced, and found to contain a number of repeated DNA sequences (Hollingshead, S. K, et al., *J. Biol. Chem.* 261: 1677–1686 (1986), Scott, J. R, et al., *Proc. Natl. Acad. Sci USA* 82:1822–1826 (1986), Scott, J. R, et al., *Infec. and Immun.* 52:609–612 (1986)). These repeated sequences may be responsible for post-transcriptional processing that results in a diversity in the size of M proteins that are produced. The mechanism by which this occurs is not understood. The range of molecular weights described for the C proteins of group B Streptococcus might result from a similar process.

Cleat et al. attempted to clone the C proteins by using two preparations of antisera to group B Streptococcus obtained from Bevanger (α and β) to screen a library of group B Streptococcus DNA in *E. coli* (Bevanger, L. et al., *Acta Path. Microbiol. Immunol. Scand. Sect. B.* 93:113–119 (1985), Cleat, P. H, et al., *Infec. and Immun.* 55(5): 1151–1155 (1987), which references are incorporated herein by reference). These investigators described two clones that produce proteins that bind to antistreptococcal antibodies. However, they failed to determine whether either of the cloned proteins had the ability to elicit protective antibody, or whether the prevalence of these genes correlated the with group B Streptococcus strains known to carry the C proteins. The role of the cloned gene sequences in the virulence of group B Streptococcus was not investigated. Since the C proteins are defined by their ability to elicit protective antibodies, this work failed to provide evidence that either of the clones encodes a C protein.

The Conjugated Vaccine of the Present Invention

Embodiments of the present invention surmount the above-discussed deficiencies of prior vaccines to group B Streptococcus through the development of a conjugate vaccine in which the capsular polysaccharides are covalently linked to a protein backbone. This approach supports the development of a T-cell dependent antibody response to the capsular polysaccharide antigens and circumvents the T-cell independent requirements for antibody production (Baker, C. J, et al., *Rev. of Infec. Dis.* 7:458–467 (1985), Kasper, D. L. et al., *J. Infec. Dis.* 153:407415 (1986), Kasper, D., et al., *Vaccines* 94, pgs. 113–117, Cold Spring Harbor Laboratory Press (1994))which references are incorporated herein by reference).

In a conjugate vaccine, an antigenic molecule, such as the capsular polysaccharides of group B Streptococcus (discussed above), is covalently linked to a "carrier" protein or polypeptide. The linkage serves to increase the antigenicity of the conjugated molecule. Methods for forming conjugate vaccines from an antigenic molecule and a "carrier" protein or polypeptide are known in the art (Jacob, C. O, et al., *Eur. J. Immunol.* 16:1057–1062 (1986); Parker, J. M. R. et al., In: *Modern Approaches to Vaccines*, Chanock, R. M. et al., eds, pp. 133–138, Cold Spring Harbor Laboratory, Cold Spring Harbor, N.Y. (1983); Zurawski, V. R, et al., *J. Immunol.* 121:122–129 (1978); Klipstein, F. A, et al., *Infect. Immun.* 37:550–557 (1982); Bessler, W. G, *Immunobiol.* 170:239–244 (1985); Posnett, D. N, et al., *J. Biol. Chem.* 263:1719–1725 (1988); Ghose, A. C, et al., *Molec. Immunol.* 25:223–230 (1988); all of which references are incorporated herein by reference).

A prototype model for conjugate vaccines was developed against Hemophilus influenzae (Anderson, P, *Infec. and Immun.* 39:223–238 (1983); Chu, C, et al., *Infect. Immun.* 40:245–256 (1983); Lepow, M, *Pediat. Infect. Dis. J.* 6:804–807 (1987), which references are incorporated herein by reference), and this model may be employed in constructing the novel vaccines of the present invention. Additional methods for producing such a conjugate vaccine are disclosed by Anderson, P. W, et al., European Patent Publication 245,045; Anderson, P. W, et al., U.S. Pat. Nos. 4,673, 574 and 4,761,283; Frank, R. et al., U.S. Pat. No. 4,789,735; European Patent Publication No. 206,852; Gordon, L. K, U.S. Pat. No. 4,619,828; Beachey, E. H, U.S. Pat. No. 4,284,537; Kuo et al., U.S. Pat. No. 5,192,540; Cryz et al., U.S. Pat. No. 5,370,872; Kasper et. al., U.S. Pat. No. 5,302,386 and Jennings et al., U.S. Pat. No. 5,576,002 all of which references are incorporated herein by reference.

The protein backbones for conjugate vaccines such as the Hemophilus influenzae vaccine have utilized proteins that do not share antigenic properties with the target organism from which the bacterial capsular polysaccharides were obtained (Ward, J. et al., In: *Vaccines*, Plotkin, S. A, et al., eds, Saunders, Philadelphia, page 300 (1988). A conjugate vaccine of Group B Streptococcus type III polysaccharride and tetanus toxoid used in baboons has been shown to induce type III-specific immunoglobulin G with opsonic activity. (Paoletti et al., *Inf. Immun.* 64:677–679 (1996)). Recently a conjugate vaccine has also been used in human trials (Kasper D., et al., 98:2308–2314, (1996)).

In contrast, the conjugate vaccine of the present invention employs immunogenic proteins, e.g. the amino terminal region of the epsilon antigen, of group B Streptococcus as the backbone for a conjugate vaccine. Alternatively the conjugate vaccine may employ the N-terminal region of the epsilon antigen or fragments thereof and in addition, other C-proteins such as the alpha and/or beta antigen. Such an approach is believed to lead to more effective vaccines (Insel, R. A, et al., *New Eng. J. Med.* (Editorial) 319(18) :1219–1220 (1988)).

The isolation and characterization of the N-terminal region of the epsilon antigen may allow optimization of both the adjuvant and antigenic properties of the polypeptide backbone/carrier of the conjugate vaccine.

Genetic Studies of the C Proteins

The present invention thus concerns the cloning of N-terminal region of the epsilon C protein of group B Streptococcus, its role in virulence and immunity, and its ability to serve as an immunogen for a conjugate vaccine against group B Streptococcus. Discussion of the N-terminal region of the epsilon antigen refers to the DNA and amino acid sequence of FIGS. 6A–6B and fragments thereof.

Despite the extensive literature available on cloning in many groups of streptococci, only limited genetic manipulations have been accomplished in group B Streptococcus (Macrina, F. L, *Ann. Rev. Microbiol.* 38:193–219 (1984), Wanger, A. R, et al., *Infec. and Immun.* 55:1170–1175 (1987)). The most widely used technique in group B Streptococcus has been the development of Tn916 and its use in transposon mutagenesis (Rubens, C. E, et al., *Proc. Natl. Acad. Sci. USA* 84:7208–7212 (1987), Wanger, A. R, et al., *Res. Vet. Sci.* 38:202–208 (1985)). However, since it would appear that there is more than one gene for the C proteins and the protective antisera bind to several proteins, screening for the C protein genes by transposon mutagenesis is impractical.

The present invention accomplishes the cloning of the N-terminal region of the epsilon antigen. A specific protocol for cloning the epsilon amino terminal region is provided in Example 7. Additionally, the protocol used to obtain expression of the N-terminal region of the alpha antigen (as described in Example 8) should be equally applicable for expressing the epsilon antigen N-terminal region. Of course, other methods known to those of skill in the art of cloning and expressing recombinant DNA may also be considered.

For example, as in PCT Application WO94/10317 it may be desirable to employ a cloning vector that could be rapidly screened for expression of proteins which bind to naturally elicited antibodies to group B Streptococcus. Since such antibodies are heterologous polyclonal antibodies and not monoclon- al antibodies, it is necessary that a vector be employed which could be easily screened through many positive clones to identify genes of interest.

A number of techniques are available for screening clones for the expression of antigens that bind to a specific antisera (Aruffo, A, et al., *Proc. Natl. Acad. Sci. USA* 84:8573–8577 (1987)). The most widely used system, λgt11, was developed by Young and Davis (Huynh, T. V. et al., In: *DNA Cloning, A Practical Approach*, Vol. 1 (Glover, D. M, Ed.) IRL Press, Washington pp. 49–78 (1985); Wong, W. W, et al., *J. Immunol. Methods*. 82:303–313 (1985), which references are incorporated herein by reference). This technique allows for the rapid screening of clones expressed in the lysogenic phage whose products are released by phage lysis. Commonly faced problems with this system include the requirement for subcloning DNA fragments into plasmid vectors for detailed endonuclease restriction mapping, preparing probes and DNA sequencing. In addition, the preparation of DNA from phage stocks is cumbersome and limits the number of potentially positive clones that can be studied efficiently. Finally, the preparation of crude protein extracts from cloned genes is problematic in: phage vector hosts.

To circumvent these problems, a plasmid vector was developed for screening cloned bacterial chromosomal DNA for the expression of proteins involved in virulence and/or immunity. The vector is prepared by modifying the commonly used plasmid cloning vector, pUC12 (Messing, J, et al., *Gene* 19:269–276 (1982); Norrander, J, et al., *Gene* 26:101–106 (1983); Vieira, J, et al., *Gene* 19:259–268 (1982); which references are incorporated herein by reference).

Using this system, plasmid clones can be easily manipulated, mapped with restriction endonucleases and their DNA inserts sequences, probes prepared and gene products studied without the necessity for subcloning. pUC12 is a 2.73 kilobase (kb) high copy number plasmid that carries a ColE1 origin of replication, ampicillin resistance and a polylinker in the lacZ gene (Ausubel, F. M, et al., *Current Topics in Molecular Biology*; Greene Publ. Assn./ Wiley Interscience, N.Y. (1987) which reference is incorporated herein by reference).

Several modifications are made in the polylinker of pUC12 (Aruffo, A, et al., *Proc. Natl. Acad. Sci. USA* 84:8573–8577 (1987) which reference is incorporated herein by reference). The overall plan in altering pUC12 is to modify the polylinker to present identical but non-cohesive BstXI sites for cloning, to add a "stuffer" fragment to allow for easy separation of the linear host plasmid, and to provide for expression from the lac promoter in all three translational reading frames.

In order to provide a site for the insertion of foreign DNA with a high efficiency and to minimize the possibility for self-ligation of the plasmid, inverted, non-cohesive BstXI ends are added to the polylinker. pUC12 is first cut with BamHI (Step 1) and the plasmid is mixed with two synthetic oligonucleotide adaptors that are partially complementary: a 15-mer (GATCCATTGTGCTGG) and an 11-mer (GTAACACGACC) (Step 2) (SEQ. ID. NOS. 7 and 8). When the adaptors are ligated into pUC12, two new BstI sites are created but the original BamHI sites are also restored (Step 3). The plasmid is then treated with polynucleotide kinase and ligated to form a closed circular plasmid (Step 4). When this plasmid is treated with BstXI, the resulting ends are identical and not cohesive (both have GTGT overhangs) (Step 5).

A second modification in the polylinker is done to allow for the purification of the linear plasmid for cloning without contamination from partially cut plasmid that can self-ligate. A blunt end, 365 base pair (bp), FnuD2 fragment is obtained from the plasmid pCDM. This cassette or "stuffer" fragment, which does not contain a BstXI site, is blunt end ligated to two synthetic oligonucleotides that are partially complementary: a 12-mer (ACACGAGATTTC) (SEQ. ID. NO. 9) and an 8-mer (CTCTAAAG) (Step 6). The resulting fragment with adaptors has 4 bp overhangs (ACAC) that are complementary to the ends of the modified pUC12 plasmid shown in Step 5. The modified pUC12 plasmid is ligated to the pCDM insert with adaptors; the resulting construct is pUX12.inverted, non-cohesive BstXI ends is added to. the polylinker. As shown in FIG. 1, pUC12 was first cut with BamHI (Step 1) and the plasmid was mixed with two synthetic oligonucleotide adaptors that are partially complementary: a 15-mer (GATCCATTGTGCTGG) (SEQ. ID. NO. 7) and an 1 1-mer (GTAACACGACC) (Step 2) (SEQ. ID. NO. 8). When the adaptors are ligated into pUC12, two new BstI sites are created but the original BamHI sites are also restored (Step 3). The plasmid was then treated with polynucleotide kinase and ligated to form a closed circular plasmid (Step 4). When this plasmid is treated with BstXI, the resulting ends are identical and not cohesive (both have GTGT overhangs) (Step 5).

Figure 2A:
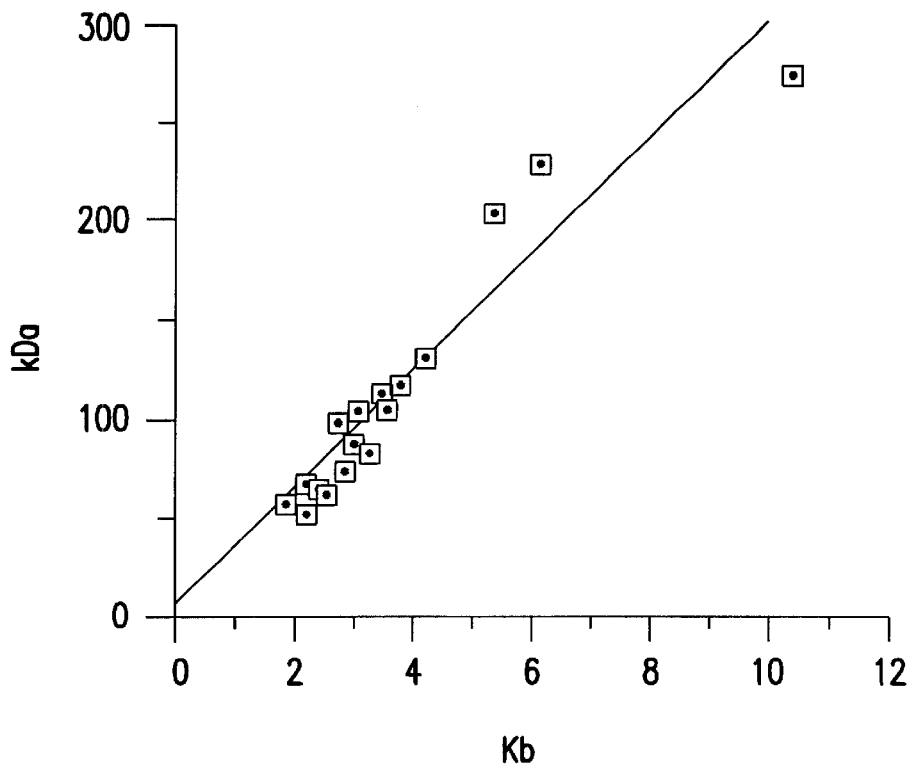
FIG. 2A–2C.
Figure 2B:
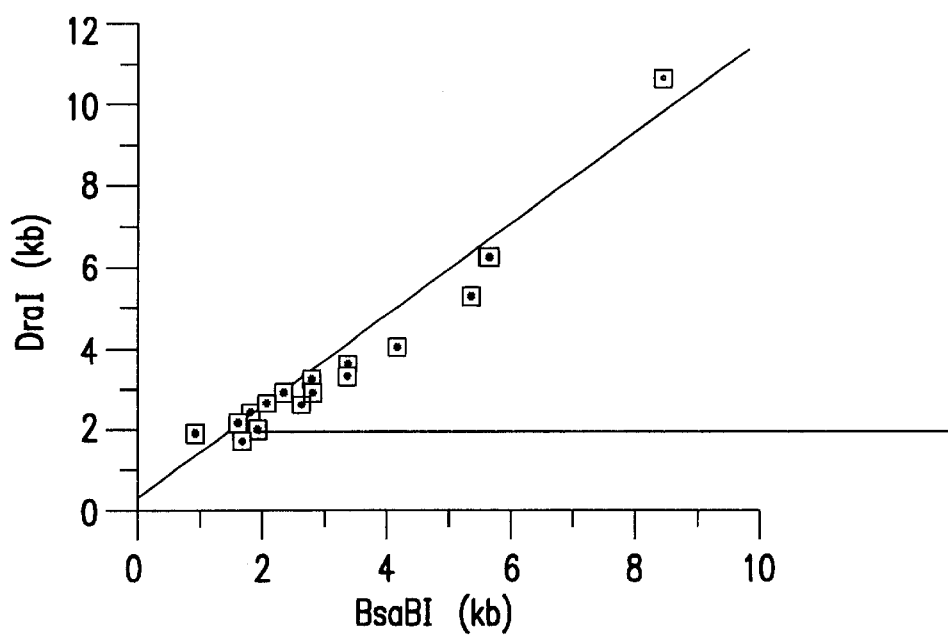
Figure 2C:
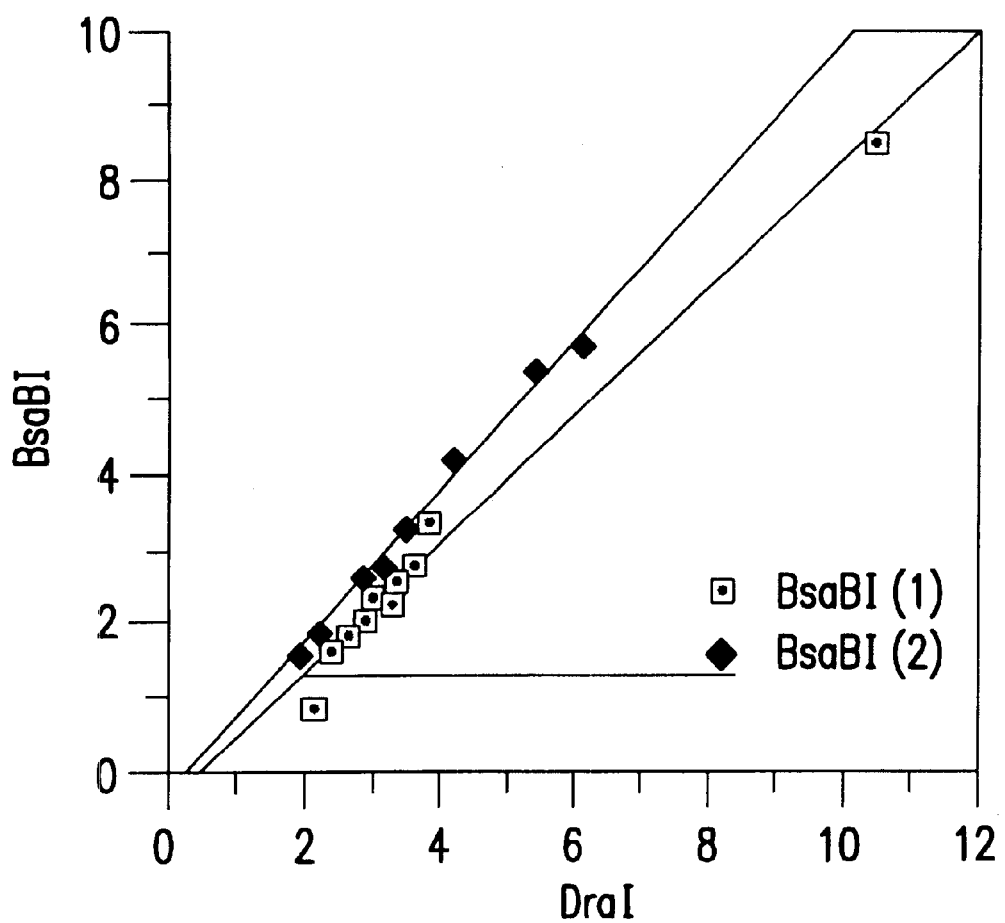

Another modification in the polylinker can be done to allow for the purification of the linear plasmid for cloning without contamination from partially cut plasmid that can self-ligate. Again, a blunt end, 365 base pair (bp), FnuD2 fragment is obtained from the plasmid pCDM. This cassette or "stuffer" fragment, which also does not contain a BstXI site, is blunt end ligated to two synthetic des that are partially complementary: a 12-mer (ACACGAGATTTC) (SEQ. ID. NO. 9) and an 8-mer (CTCTAAAG) (Step 6). The resulting fragment with adaptors has 4 bp overhangs (ACAC) that are complementary to the ends of the modified pUC12 plasmid shown in Step 5. The modified pUC12 plasmid was ligated to the pCDM insert with adaptors; the resulting construct, named pUX12, is shown in FIG. 2. The pUX12 plasmid can also be formed by recombinant methods (or by homologous recombination), using plasmid pUC12.

Since pUX12 is to be used as an expression vector, it is preferable to further modify the polylinker such that it will contain all three potential reading frames for the Lac promoter. These changes allow for the correct translational reading frame for cloned gene fragments with a frequency of one in six. For example, a cloned fragment can insert in the vector in one of two orientations and one of three reading frames. To construct a +1 reading frame, the pUX12 plasmid is cut with the restriction enzyme EcoRI which cleaves at a unique site in the polylinker. The single stranded 5' sticky ends are filled in using the 5'–3' polymerase activity of T4 DNA polymerase, and the two blunt ends ligated. This results in the loss of the EcoRI site, and the creation of a new XmnI site The above construction can be confirmed by demonstrating the loss of the EcoRI site and confirming the presence of a new XmnI site in the polylinker. In addition, double stranded DNA sequencing on the +1 modified pUX12 plasmid is performed using standard sequencing primers (Ausubel, F. M, et al., *Current Topics in Molecular Biology*; Greene Publ. Assn./ Wiley Interscience, N.Y. (1987)). The DNA sequence should show the addition of 4 base pairs to the polylinker and confirmed the modification of pUX12 to a +1 reading frame. This plasmid is called pUX12+1.

In order to construct a −1 reading frame, the pUX12 vector is cut with the restriction enzyme SacI which cuts at a unique site in the polylinker of pUX12. The single stranded 3' sticky ends are cut back to blunt ends using the 3'–5' exonuclease activity of T4 polymerase, and the resulting blunt ends ligated.

The resulting sequence should eliminate the SacI site while resulting in a new FnuD2 site. However, restriction mapping of the pUX12-1 plasmids has shown that while the SacI site is absent, there is no FnuD2 site present. In addition, the SmaI/XmaI sites on the polylinker were no longer present. Several potential pUX12-1 constructs were sequenced from mini-prep, double-stranded DNA. Of the six modified plasmids sequenced, one was found with ten nucleotides absent, thereby creating a −1 reading frame. This suggests that the T4 DNA polymerase has additional exonuclease activity and cuts back additional double stranded portions of the polylinker. Nevertheless, the resulting plasmid had a −1 reading frame. The plasmid was named pUX12-1.

The use of the pUX12 vectors in the cloning of antigenic proteins of group B Streptococcus has been discussed in detail in PCT Application WO 94/10317. In brief, DNA derived from group B Streptococcus, or complementary to such DNA is introduced into the pUX12, pUX12+1 or pUX12-1 vectors and transformed into *Escherichia coli*. The cloned DNA is expressed in *E. coli* and the cellular lysate is tested to determine whether it contains any protein capable of binding to antisera to group B Streptococcus.

There are a number of potentially interesting modifications of pUX12 that could increase its utility. For example, the lac promoter could be replaced by another promoter, the origin of replication could be modified to produce a lower copy number vector and the drug resistance marker could be changed.

Any vector capable of providing the desired genetic information to the desired host cell may be used to provide genetic sequences encoding the epsilon antigen derivatives of the invention to a host cell. For example, in addition to plasmids, such vectors include linear DNA, cosmids, transposons, and phage. A potential problem with cloning streptococcal proteins is exemplified by cloning of the repeat region of the alpha C-protein which has been found to be unstable in some instances. Secondly, problems have also been encountered in expressing certain streptococcal proteins.

The host cell is not limited to *E. coli*. Any bacterial or yeast (such as *S. cerevisiae*) host that is capable of expressing the derivatives of the invention may be used as an appropriate host. For example, *B. subtilis* and the group B Streptococcus may be used as hosts. Methods for cloning into such hosts are known. For example, for Gram-positive hosts, see Harwood, C. R., et al., eds., "*Molecular Biological Methods for Bacillus*," Wiley-Interscience, N.Y., 1991) for a description of culture methods, genetic analysis plasmids, gene cloning techniques, the use of transposons, phage, and integrational vectors for mutagenesis and the construction of gene fusions, and methods of measuring gene expression. Appropriate hosts are available from stock centers such as the American Type Culture Collection (Rockville, Md., USA) and the Bacillus Genetic Stock Center (Ohio State Univ., Columbus, Ohio, USA).

Alternatively, the N-terminal region of the epsilon antigen may be expressed or clones using a yeast host or shuttle vector, e.g. *S. cerevisiae* yeast plasmids including those containing the 2-micron circle or their derivatives. Such plasmids are well known in the art (Botstein, D. et al., *Miami Wntr. Symp.* 19:265–274 (1982); Broach J. R. in:*Molecular Biology of the Yeast Saccharomyces: Life Cycle and Inheritance*, Cold Spring Harbor Laboratory, Cold Spring Harbor, N.Y. pp.445470 (1981); Broach J. R., *Cell* 28:203–204 (1982); Bollon D. P. et al., *J. Clin. Hematl. Oncol.* 10:39–48 (1980); Maniatis, T. In:*Cell Biology: A Comprehensive Treatise*, Vol. 3, Gene Expression, Academic Press, N.Y., pp 563–608 (1980); Heslot et al eds., *Molecular Biology and Genetic Engineering of Yeasts*, CRC Press, Boca Raton, (1991)) and are commercially available.

One of skill in the art may also obtain the N-terminal region of the epsilon antigen or fragments thereof, by chemical synthesis of the amino acid sequence or a fragment of the sequence in FIG. 6B. An N-terminal region fragment can include inter alia, the sequence of FIG. 6B without. the signal peptide, as well as those fragments that would be thought to be antigenic by those of skill in the art.

Recently, workers in the area of chemical synthesis have indicated that it should be possible to routinely construct large synthetic. proteins (>200 amino acids in length). (Muir et al., *Curr. Opin. Biotech.* 4:420–427, 1993). Several reports of synthesis of proteins of at least 90–99 amino acids have also appeared. (Schnolzer et al., *Science* 256:221–225, 1992; Hojo et al, *Bull. Chem. Soc. Jpn.* 65:3055–3063, 1992). Thus, chemical synthesis techniques should be a viable option for preparing the N-terminal region of the epsilon antigen or fragments thereof. In fact a 90 amino acid protein from *Bacillus stearothermophilus* has already been synthesized using protected peptide fragments (Hojo et al., 65:3055–3063, 1992). Further, the use of TASP (template assembled synthetic proteins) should be helpful in this regard. (Eggleston et al., *Macromolecular Symposia* 101:397404 (1996)).

The present invention concerns a vaccine comprising a polysaccharide (such as the capsular polysaccharide) which is characteristic of the group B Streptococcus conjugated to a protein which is also characteristic of the group B Streptococcus. The "polysaccharide" and "protein" of such a conjugated vaccine may be identical to a molecule which is characteristic of the group B Streptococcus, or they may be functional derivatives of such molecules.

For the purposes of the present invention, a group B Streptococcus polysaccharide is any group B-specific or type-specific polysaccharide. Preferably, such polysaccharide is one which, when introduced into a mammal (either animal or human) elicits antibodies which are capable of reacting with group B Streptococcus may be employed. Examples of the preferred polysaccharides of the present invention include the capsular polysaccharide of the group B Streptococcus, or their equivalents. For the purposes of the present invention, any protein which when introduced into a mammal (either animal or human) either elicits antibodies which are capable of reacting a protein expressed by group B Streptococcus, or which increases the immunogenicity of a polysaccharide to elicit antibodies to a polysaccharide of the group B Streptococcus may be employed. Examples of the preferred proteins of the present invention include the C proteins of the group B Streptococcus, or their equivalents.

Examples of functional derivatives or equivalents of the peptide antigens include fragments of a natural protein, such as N-terminal fragment, C-terminal fragment or internal sequence fragments of the group B Streptococcus C protein epsilon antigen that retain their ability to elicit protective antibodies against the group B Streptococcus. The term functional derivatives is also intended to include variants of a natural protein (such as proteins having changes in amino acid sequence but that retain the ability to elicit an immunogenic, virulence or antigenic property as exhibited by the natural molecule), for example, the variants of the epsilon antigen with an altered flanking sequence.

By functional equivalent or derivative is further meant an amino acid sequence that is not identical to the specific ammo acid sequence, but rather contains at least some amino acid changes (deletion, substitutions, inversion, insertions, etc.) that do not essentially affect the immunogenicity or protective antibody producing production of the protein as compared to a similar activity of the specific amino acid sequence, when used for the desired purpose. Preferably, an "equivalent" or functionally derivative amino acid sequence contains at least 85–99% homology at the amino acid level to the specific amino acid sequence, most preferably 90% and in an especially highly preferable embodiment, at least 95 % homology at the amino acid level.

The peptide antigen that is conjugated to the polysaccharide in the vaccine of the invention may be a peptide encoding the native amino acid sequence of the N-terminal region of the epsilon antigen of FIG. 6B or it may be a functional derivative or equivalent of the native amino acid sequence.

Epsilon antigens from other strains of the group B Streptococcus may also be prepared and used in a similar manner as a slight variability in the sequence of the protein, would not alter the biological properties and their functional ability to elicit protective antibodies. For example, a group B Streptococcus epsilon antigen isolated from a different strain of the group B Streptococcus is intended to be within the scope of the invention.

The peptides used in the invention, whether encoding a native protein or a functional derivative thereof, are conjugated to a group B Streptococcus carbohydrate moiety by any means that retains the ability of these proteins to induce protective antibodies against the group B Streptococcus.

Heterogeneity in the vaccine may be provided by mixing specific conjugated species. For example, the vaccine preparation may contain one or more copies of one of the peptide forms conjugated to the carbohydrate, or the vaccine preparation may be prepared to contain more than one form of the above functional derivatives and/or the native sequence, each conjugated to a polysaccharide used therein.

A multivalent vaccine may also be prepared by mixing the group B-specific conjugates as prepared above with other proteins, such as diphtheria toxin or tetanus toxin, and/or other polysaccharides, using techniques known in the art.

Heterogeneity in the vaccine may also be provided by utilizing group B Streptococcal preparations from group B Streptococcal hosts (especially into Streptococcus agalactiae), that have been transformed with the recombinant constructs such that the streptococcal host expresses the N-terminal region of the epsilon antigen protein or a functional derivative thereof. In such cases, homologous recombination between the genetic sequences encoding the epsilon antigen will result in spontaneous mutation of the host, such that a population of hosts is easily generated and such hosts express a wide range of antigenic epsilon antigen functional derivatives useful in the vaccines of the invention.

As used herein, a polysaccharide or protein is "characteristic" of a bacteria if it is substantially similar in structure or sequence to a molecule naturally associated with the bacteria. The term is intended to include both molecules which are specific to the organism, as well as molecules which, though present on other organisms, are involved in the virulence or antigenicity of the bacteria in a human or animal host.

The vaccine of the present invention may confer resistance to group B Streptococcus by either passive immunization or active immunization. In one embodiment of passive immunization, the vaccine is provided to a host (i.e. a human or mammal) volunteer, and the elicited antisera is recovered and directly provided to a recipient suspected of having an infection caused by a group B Streptococcus.

The ability to label antibodies, or fragments of antibodies, with toxin labels provides an additional method for treating group B Streptococcus infections when this type of passive immunization is conducted. In this embodiment, antibodies, or fragments of antibodies which are capable of recognizing the group B Streptococcus antigens are labeled with toxin molecules prior to their administration to the patient. When such a toxin derivatized molecule binds to a group B Streptococcus cell, the toxin moiety will cause the death of the cell.

In a second embodiment, the vaccine is provided to a female (at or prior to pregnancy or parturition), under conditions of time and amount sufficient to cause the production of antisera which serve to protect both the female and the fetus or newborn (via passive incorporation of the antibodies across the placenta). Passive protection has been shown to result from immunization with either the alpha or beta C-protein (Michel et al., 59:2023–2028 (1991)). Furthermore, transferance of the protective effect between mother and unborn offspring has already been show to be successful following maternal immunization with the beta C-protein or a polysaccharide-beta antigen conjugate. (Madoff et al. Inf. Immun. 60: 4989–4994, 1992, Madoff et al., *J. Clin. Invest.* 94:286–292 (1994)).

The present invention thus concerns and provides a means for preventing or attenuating infection by group B Streptococcus, or by organisms which have antigens that can be recognized and bound by antisera to the polysaccharide and/or protein of the conjugated vaccine. As used herein, a vaccine is said to prevent or attenuate a disease if its administration to an individual results either in the total or partial attenuation (i.e. suppression) of a symptom or condition of the disease, or in the total or partial immunity of the individual to the disease.

The administration of the vaccine (or the antisera which it elicits) may be for either a "prophylactic" or "therapeutic" purpose. When provided prophylactically, the compound(s) are provided in advance of any symptom of group B Streptococcus infection. The prophylactic administration of the compound(s) serves to prevent or attenuate any subsequent infection. When provided therapeutically, the compound(s) is provided upon the detection of a symptom of actual infection. The therapeutic administration of the compound(s) serves to attenuate any actual infection.

The vaccines of the present invention may, thus, be provided either prior to the onset of infection (so as to prevent or attenuate an anticipated infection) or after the initiation of an actual infection.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

As would be understood by one of ordinary skill in the art, when the vaccine of the present invention is provided to an individual, it may be in a composition which may contain salts, buffers, adjuvants, or other substances which are desirable for improving the efficacy of the composition. Adjuvants are substances that can be used to specifically augment a specific immune response. Normally, the adjuvant and the composition are mixed prior to presentation to the immune system, or presented separately, but into the same site of the animal being immunized. Adjuvants can be loosely divided into several groups based upon their composition. These groups include oil adjuvants (for example, Freund's complete and incomplete), mineral salts (for example, $AlK(SO_4)_2$, $AlNa(SO_4)_2$, $AlNH_4(SO_4)$, silica, kaolin, and carbon), polynucleotides (for example, poly IC and poly AU acids), and certain natural substances (for example, wax D from *Mycobacterium tuberculosis*, as well as substances found in *Corynebacterium parvum*, or *Bordetella pertussis*, and members of the genus Brucella. Among those substances particularly useful as adjuvants are the saponins such as, for example, Quil A. (Superfos A/S, Denmark). Examples of materials suitable for use in vaccine compositions are provided in Remington's Pharmaceutical Sciences (Osol, A, Ed, Mack Publishing Co, Easton, Pa., pp. 1324–1341 (1980), which reference is incorporated herein by reference).

The therapeutic compositions of the present invention can be administered parenterally by injection, rapid infusion, nasopharyngeal absorption (intranasopharangeally), dermoabsorption, or orally. The compositions may alternatively be administered intramuscularly, or intravenously. Compositions for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

Many different techniques exist for the timing of the immunizations when a multiple administration regimen is utilized. It is possible to use the compositions of the invention more than once to increase the levels and diversities of expression of the immunoglobulin repertoire expressed by the immunized animal. Typically, if multiple immunizations are given, they will be given one to two months apart.

According to the present invention, an "effective amount" of a therapeutic composition is one which is sufficient to achieve a desired biological effect. Generally, the dosage needed to provide an effective amount of the composition will vary depending upon such factors as the animal's or human's age, condition, sex, and extent of disease, if any, and other variables which can be adjusted by one of ordinary skill in the art.

The antigenic preparations of the invention can be administered by either single or multiple dosages of an effective. amount. Effective amounts of the compositions of the invention can vary from 0.01–1,000 µg/ml per dose, more preferably 0.1–500 µg/ml per dose, and most preferably 10–300 µg/ml per dose.

Having now generally described the invention, the same will be more readily understood through reference to the following examples which are provided by way of illustration, and are not intended to be limiting of the present invention, unless specified.

Bacterial strains, plasmids, transposons and media.

60 clinical isolates and classical lab strains of GBS were studied, 26 of them from the Channing Laboratory panel of clinical isolates collected by Dr. Dennis Kasper and his colleagues. Others were kindly provided by Drs. Carol Baker (Baylor College of Medicine), Lars Bevanger (Trottenheim, Norway), Henry Blumberg (CDC, Emory University), Patricia Ferrieri (University of Minnesota), Emil Gotschlich (from the collection of Rebecca Lancefield at the Rockefeller University), Gunnar Lindahl (University of Lund, Sweden), and Graziella Orifici (Instituto Sanitario, IRIS, Rome Italy). GBS strains were grown on blood-agar plates supplied by Becton Dickinson or in liquid Todd-Hewitt broth (THB) medium.

Three strains of *E. coli* were used to make competent cells for cloning experiments. Strains DH5-α (Rec A-) and MC1061 (Rec A+) express a high copy number and strain pCNB expresses the col E1 replicon as a low copy number plasmid. *E. coli* were grown on Lennox L Broth-agar (LB) plates and in liquid LB medium. Antibiotic selection was achieved with ampicillin to a final concentration of 100 µg/ml.

EXAMPLE 1

Immunoblotting of GBS Extracts with 4G8 Alpha-specific Monoclonal Antibody

It has been shown previously that different strains of GBS express different sizes of alpha antigen (Madoff, L. C., et al., *Infect Immun* 59(1):204–210 (1991)). These studies were done using western immunoblots probing with the a monoclonal antibody, 4G8, that is known to bind within the repeat region. Strains, like the prototype Ia/C(β) strain 515, were typed as alpha antigen negative by classical techniques using polyclonal typing antisera raised to partially purified C proteins. To characterize this diversity of size of the alpha antigen on the phenotypic level, 20 different isolates of GBS previously characterized (Madoff, L. C., et al., *Infect Immun* 59(1):204–210 (1991)) and expressing a wide range of alpha antigen sizes, and four strains of GBS negative for alpha antigen expression, were chosen from the collection of the Channing Laboratory and immunoblotted.

Methods

Sodium dodecyl sulfate-polyacrylamide gel electrophoresis (SDS-PAGE) and Western immunoblots were performed by standard techniques with a Mighty Small electrophoresis apparatus and a Transphor electroblotter (Hoefer, San Francisco) (Madoff, L. C., et al., *Infect Immun* 59(1):204–210 (1991)).

Two types of primary antibodies were used for immunoblots (see Table 1). The first group of antibodies were raised against individual surface proteins from GBS. Specifically, polyclonal antibody was raised against the alpha antigen clone pJMS23 (anti-alpha) and the monoclonal antibody 4G8 raised to GBS strain A909 (Madoff, L. C., et al., *Infect Immun* 59(1):204–210 (1991)) recognized the C protein alpha antigen. 4G8 is specific to an epitope in the repetitive region of alpha. Antiserum to the subclone expressing only the alpha antigen amino terminus was also used. All antibodies were used at 1:1,000 dilution in PBS/T.

TABLE 1

Antisera. A table of all antisera used.

| Antibody | Type | Animal | Antigen | Comments | Source |
|---|---|---|---|---|---|
| alpha | polyclonal | rabbit | clone | anti-whole alpha | Madoff |
| N-term. | polyclonal | rabbit | clone | anti-alpha N-term | Michel |
| 4G8 | monoclonal | mouse | A909 | anti-alpha repeats | Madoff |
| Beta | polyclonal | rabbit | clone | anti-whole beta | Madoff |
| Rib | polyclonal | rabbit | purified | anti-whole Rib | Lindahl |
| R1 | polyclonal | rabbit | purified | anti-R1 | Ferrieri |
| R4 | polyclonal | rabbit | purified | anti-R4 | Ferrieri |
| 1a | polyclonal | rabbit | O90 | anti-type 1a | Kasper |
| 1b | polyclonal | rabbit | R36B | anti-type 1b | Kasper |
| II | polyclonal | rabbit | 18RS21 | anti-type II | Kasper |
| III | polyclonal | rabbit | M781 | anti-type III | Kasper |
| IV | polyclonal | rabbit | 3139 | anti-type IV | Kasper |
| V | polyclonal | rabbit | 1169 | anti-type V | Kasper |
| VI | polyclonal | rabbit | NT6 | anti-type VI | Kasper |
| VII | polyclonal | rabbit | 7271 | anti-type VII | Kasper |
| VII | polyclonal | rabbit | JM913 | anti-type VIII | Kasper |

After being electroblotted onto nitrocellulose sheets, samples were probed with the 4G8 monoclonal antibody (Madoff, L. C., et al., *Infect Immun* 59(1):204–210 (1991)) As expected, 20 of the isolates were positive for alpha antigen expression. Among these isolates, the maximum molecular mass of the alpha antigen varied from 61,000 to 270,000 Da.

Results

Protein extracts from these strains displayed the heterogenous peptide ladder associated with protein alpha (Madoff, L. C., et al., *Infect Immun* 59(1):204–210 (1991)). However, two different phenotypic laddering patterns were observed in this panel of strains. In 12 of the strains, the peptide ladder fragments were exactly in line with those of the prototypical alpha antigen bearing strain A909; this strain was used to clone bca. These strains were classified as exhibiting the "classic" alpha laddering pattern. The ladder fragments from strains DK8, DA, 515, DK 4-1, DK3, RO, and strain isolates GH2A and GH7 were slightly out of frame with those exhibiting this pattern and were said to exhibit the epsilon laddering pattern. Although the distance between bands was the same in both groups, the ladder fragments for epsilon strains were slightly below those of alpha strains.

Figure 3A:
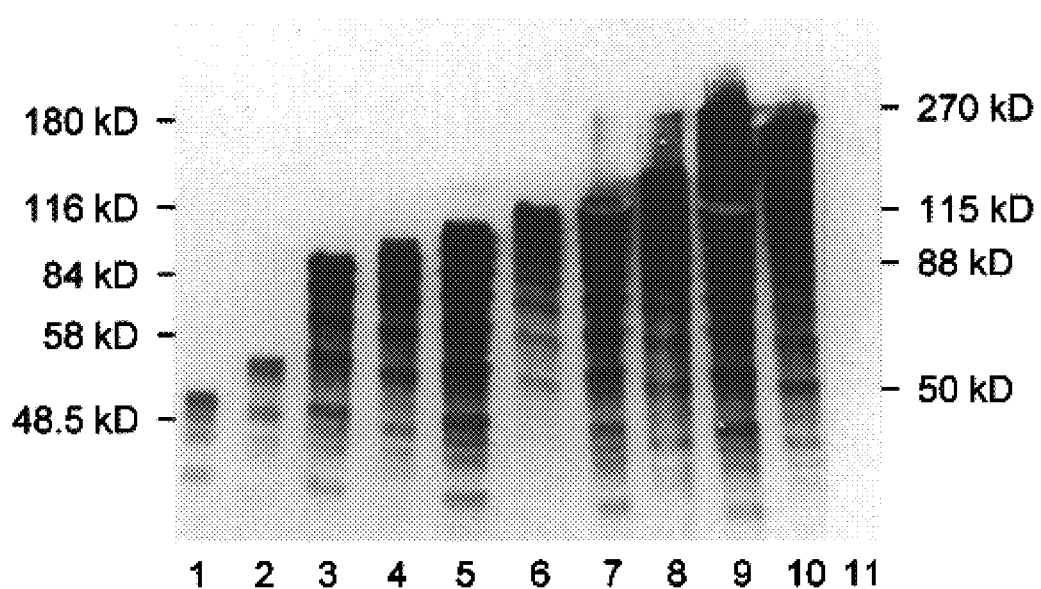
FIGS. 3A–3B. Immunological analysis of the C protein alpha and epsilon antigens. 4G8 (anti-repeat) antiserum binds to both alpha and epsilon (FIG. 3A). Epsilon, however, displays a ladder-pattern that is out of phase with respect to alpha. The antiserum to the amino terminus of alpha fails to bind epsilon on immunoblot (FIG. 3B), indicating the region of difference between the two antigens. Lanes 1, 3, 5, 7, and 9 (72, 144, A909, Carson, and DK 13) are alpha-positive and lanes 2, 4, 6, 8, and 10 (GH7, DK8, 515, DK 4-1, and Robinson) are epsilon-positive (78-008). Lane 11 is C protein-negative. Molecular weight markers are to the left and calculated molecular weights to the right of samples.

FIG. 3A is a sample immunoblot of 10 of the alpha and epsilon-positive strains that shows the relative sizes and the laddering patterns of the alpha and epsilon antigen.

EXAMPLE 2

Determination of Alpha Gene Size with Southern Blotting

Once the extent of phenotypic diversity of the alpha and epsilon antigens had been identified in the panel of strains, DNA blotting was used to characterize gene number and size among strains. First, it was necessary to determine whether the ladder of peptide fragments corresponding to the alpha or epsilon antigen were the product of only one gene. In the M protein of group A Streptococcus, for example, phenotypic diversity is generated not only by rearrangement of repeating regions within its gene, but also by duplications of the M-protein gene itself (Hollinghead et al, *Mol. Gen. Genet.* 207:196–203, (1987)).

Methods

To investigate whether the alpha and epsilon C-protein genes were present in a single copy within the different strains, genomic DNA was digested with DraI that cuts outside of the open reading frame of the alpha antigen gene (see FIG. 2, electrophoresed, and Southern blotted. The blots were then probed with a 32P-labeled StyI repeat fragment specific to the repeat pattern of bca.

Standard procedures were followed from Ausubel et al. for the preparation of plasmid DNA from *E. coli*, restriction enzyme digestion, agarose gel electrophoresis, and Southern blot hybridization (Ausubel, F. M., et al., Current Protocols in Molecular Biology, New York: John Wiley & Sons, 1993). Genomic DNA was isolated by the method of Hull et al. (*Infect. Immun.* 33:933–938 (1981)). as modified by Rubens et al. (Rubens, C. E., et al., *Proc. Natl. Acad. Sci USA* 84(20):7208–7212 (1987)).

Four nucleotide probes were used for Southern blots. A probe specific for the entire 3,060-bp gene of the alpha antigen was derived from a subclone of the alpha gene (pJMS23-1) digested with HindIII. A 246-bp probe specific for the repeats of alpha was also derived from pJMS23-1 by digestion with StyI and purified from an agarose gel with the GeneClean kit (Bio101, La Jolla, Calif.). A probe internal to the amino terminus of the alpha gene (without the signal sequence), was prepared by a polymerase chain reaction (PCR) with primers designed from the published alpha gene sequence (Michel, J. L., et al., *Proc. Natl. Acad Sci USA* 89(21):10060–10065 (1992) #2492) (FIG. 1). A probe for the beta antigen gene was derived from the beta clone pJMS1 by digestion with BamHI, agarose gel separation of a 3,100 bp fragment, and purification by Gene Clean (Bio 101).

Results

For all 24 strains, only one fragment homologous to the StyI probe was found. Fragment size differed between strains and was found to be larger in strains that had larger alpha or epsilon C-proteins, indicating that changes in the size of the expressed antigens may be due to differences in the size of the structural gene. The finding of a single gene copy per strain was confirmed by Southern blots following digestion with multiple restriction enzymes and using pulsed field gel electrophoresis (data not shown).

Once it had been determined that the alpha antigen gene was present in a single copy within the strains, the size of the alpha C-protein gene in each of the strains was compared with the apparent molecular mass of the alpha antigen observed on immunoblots. The size of the alpha antigen gene on Southern blot was found to range from 1.85 to 10.25 kb and was directly correlated with the size of expressed alpha or epsilon antigens (FIG. 2). Therefore, the variability among strains in the maximal size of these antigens is directly related to the size of their structural genes.

EXAMPLE 3

Localization of Alpha Gene Size Determinants

To determine how the composition of the alpha antigen gene was altered as its size changed, Southern blots were made from BsaBI digests. BsaBI cuts just outside either end of the repeat region, within the N-terminal and C-terminal of the gene. As seen in FIG. 2B shows, there is approximately a one to one relationship between the increasing size of the repeat region and the size of the alpha antigen gene. Therefore, differences in the size of the expressed alpha antigen are largely a function of the number of repeats contained within the alpha gene.

EXAMPLE 4

Possible Variability in the C-terminal of the Gene

After it had been shown that the size of the gene could be predicted based upon the number of repeats that it contained, new DNA blots were made to more closely investigate the size of the amino and carboxy ends of the repeat region of the gene among different strains. Southern blots made from a StyI-NsiI double digest were used to examine the C-terminal for any variation between strains. As seen in FIG. 2, the StyI-NsiI double digestion cut out a 435 base pair fragment of the C-terminal anchor and repeat region. When the blots were probed with the HincII-NsiI DNA fragment, only the 435 bp fragment was seen. On the basis of this data (not shown), the size of the C-terminal appears to be conserved between strains.

EXAMPLE 5

Immunologic Analysis of the Epsilon Antigen

Laddering proteins are of interest because of the antigenic variability they introduce. Such variability may have a role in changing the virulence properties and immune targets of the organism. The relationship between alpha and the cross-reactive antigen, epsilon was investigated. 4G8 monoclonal antiserum against the repeating subunits of alpha and a new alpha amino terminus-specific antiserum permitted analysis of the different segments of the gene individually.

Figure 3B:
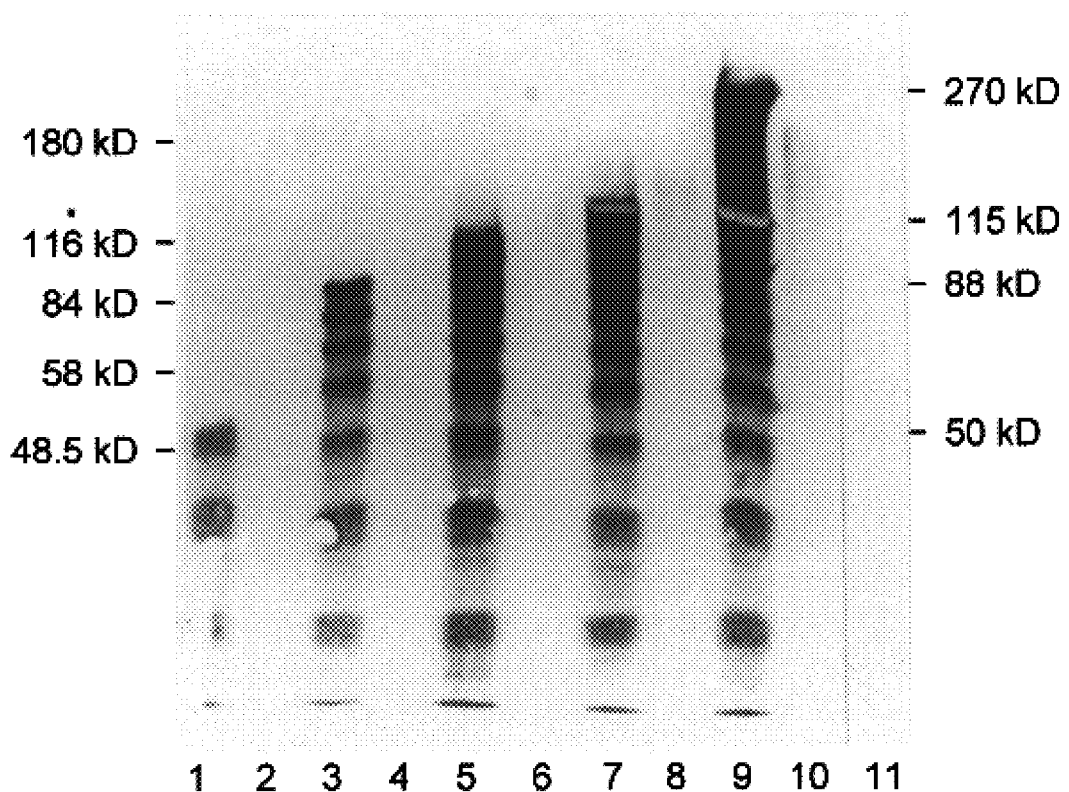

FIG. 3 shows the results of immunoblot of GBS strains expressing either the alpha or epsilon antigen probed with 4G8 antibody and with alpha amino terminus antiserum. Immunoblot probed with 4G8 antibody showed the cross-reactivity of alpha and epsilon. This is strong evidence that the two proteins share significant homology and, in particular, that the repeat regions share epitopes. However, antiserum raised against the subcloned amino terminus of alpha failed to bind the epsilon-positive 515 on an immunoblot and was highly specific for alpha strains including A909. C protein-negative control strains failed to bind anti-alpha, 4G8, or anti-alpha amino terminus sera. The immunologic data supports idea that alpha and epsilon share significant homology within the repeat region, but that the amino termini are distinct.

EXAMPLE 6

Southern Blot Analysis of the Epsilon Antigen

Figure 4A:
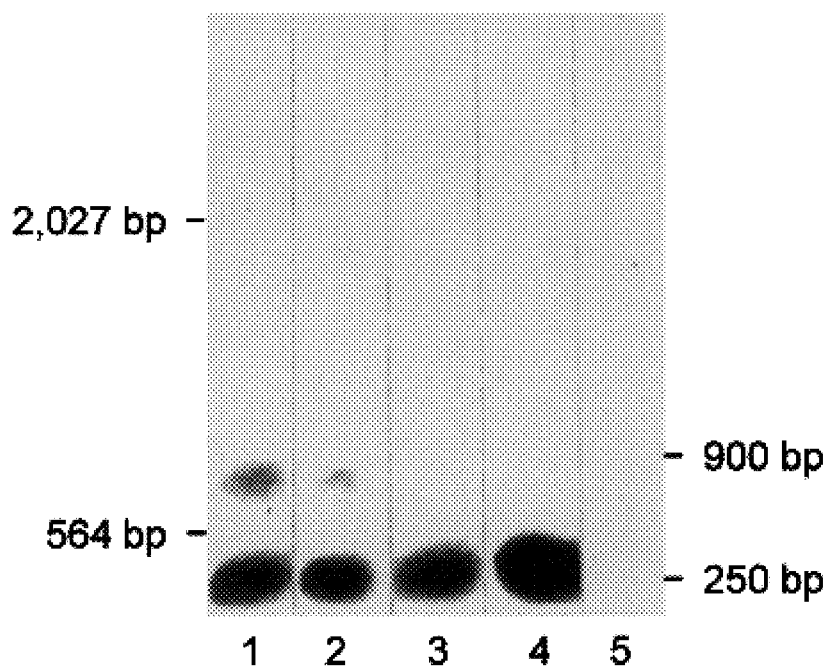
FIGS. 4A–4B. Genetic comparison of C protein alpha and epsilon antigens. Southern blot analysis of the alpha and epsilon antigens revealed homology in the repeat regions, but divergence in the amino. terminus. Blot A was probed with he alpha-repeat probe, and blot B was probed with he alpha-amino terminus probe. Samples 1 and 2 (A909 and H36B) are alpha-positive, samples 3 and 4 (515 and Davis) are epsilon-positive, and sample 5 (18RS21) is C protein-negative. Molecular weight markers are to the left and calculated molecular weights to the right of the samples.
Figure 4B:
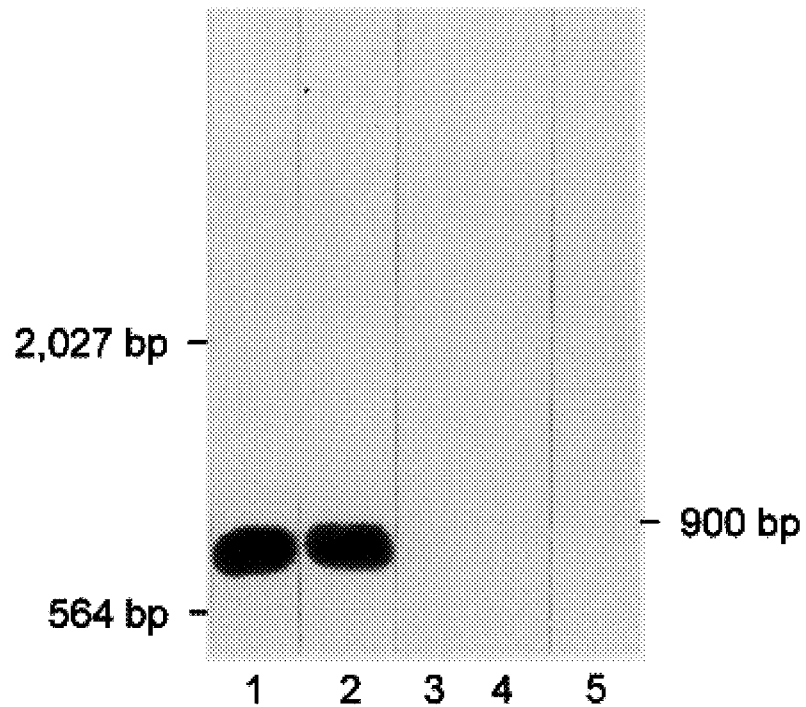

Genomic DNA from A909, the prototype alpha-positive strain, and 515, the prototype epsilon-positive strain, was double digested with DraI and StyI and probed on a Southern blot with the alpha-amino terminus probe to determine the homology of the alpha and epsilon amino termini. The results are shown in FIG. 4. The amino terminus probe failed, even under low stringency, to hybridize to genomic DNA from 515, the prototype epsilon-positive strain. When the same Southern blots were re-probed with the alpha repeat probe, both alpha- and epsilon-positive strains hybridized, thus indicating that the repeat region is largely the same. DNA from non-C protein-bearing strains was run as a negative control and failed to hybridize with amino terminus or repeat probe. This indicated that alpha and epsilon have significantly different nucleotide sequences in the amino termini.

A new surface-associated protein, the epsilon antigen, was discovered and characterized. Genetic and immunologic analysis of epsilon indicated that the alpha and epsilon antigens shared a high degree of homology in the signal sequence, the repetitive region, and the carboxyl terminus, but are significantly different at the amino terminus by both nucleotide and antibody probe. This difference explains the cross-reactivity of anti-alpha serum with epsilon and the distinct laddering pattern of epsilon on immunoblot. In identifying an area of marked difference between alpha and epsilon, a simple two-step screening technique to differentiate alpha and epsilon by either Southern blot or immunoblot was created. Both alpha and epsilon bind to the whole gene or repeat probe from alpha, but only alpha binds to the amino terminus-specific probe from alpha. Until the clone was isolated, there was no specific probe for epsilon.

The alpha and epsilon antigens probably arose from a common evolutionary predecessor through transferral of the amino terminus from another gene. By incorporating a new surface antigen, GBS increases its antigenic diversity, and thus, its ability to survive a variety of immune response conditions. Since they share a high degree of homology in the repeat region, a recombinational event was probably recent in the evolutionary history of the organism. It is possible, however, that the integrity of the repetitive domains must be maintained for the survival of the organism and is thus maintained by selection.

EXAMPLE 7

Cloning of Epsilon Amino Terminus

Having identified the amino terminus as the principal site of the difference between alpha and epsilon, the unique region of epsilon was cloned and sequenced so that it could be further characterized genetically and immunologically. A clone of epsilon will be useful for assessing the heterogeneity of and patterns of cross-reactivity with other surface-associated proteins, and will help elucidate the biological function of these surface-associated proteins of GBS.
Methods The clone of the epsilon amino terminal region was derived by PCR from genomic DNA of the epsilon-positive GBS strain 515. Primers were designed from the published sequence of the alpha antigen gene (Michel, J. L., et al., *Proc. Natl. Acad. Sci. USA* 89(21):10060–10065 (1992)) with sites upstream of the signal sequence and immediately downstream of the amino terminus. The primers were engineered with restriction sites for the enzymes EcoRI (upstream) and BamHI (downstream). The exact primer sequences are listed in FIG. 5 (SEQ. ID. NOS. 1 and 2. The PCR reactions were run according to Ausubel et al. (Ausubel, F. M., et al., Current Protocols in Molecular Biology, New York: John Wiley & Sons, 1993), with the exception that 2 µl of each primer was used per reaction at a 50 mM concentration with no additional magnesium. Reactions with no template DNA and with only one primer were run to control for contaminants. The PCR was performed with a Perkin-Elmer Cetus thermal cycler (model 480) and Vent polymerase (New England Biolabs) with 90 seconds at 94° C. for denaturing, 120 seconds at 52° C. for annealing, 180 seconds at 72° C. for extension, and 30 cycles.

The amino terminal region of epsilon was prepared by PCR, concentrated from six PCR reactions, and digested overnight with EcoRI and BamHI (Gibco-BRL). The cloning vector, pBluescript KS- (Stratagene), containing an ampicillin resistance marker, was also digested overnight with the same enzymes. Both vector and insert were run on an agarose gel to remove any uncut pieces or small fragments from the digestion and purified by Gene Clean (Bio101). A 20-µl ligation reaction with T4 DNA ligase (New England Biolabs) was incubated overnight at 16° C. with controls to check for self-ligation (no insert) and controls to check for uncut vector (no ligase). 1.5 µl from the ligation was transformed into 50 µl of competent cells prepared from E. coli strain MC1061 (Ausubel, F. M., et al., Current Protocols in Molecular Biology, New York: John Wiley & Sons, 1993). The transformation was performed by electroporation with a Gene Pulser (Bio-Rad, Hercules, Calif.) with parameters 2.5 mV, 25 µF, and 200 Ohms. LB plates with ampicillin (100 µg/ml) were used to screen for transformants.

DNA sequencing was performed at the Beth Israel Hospital's Molecular Medicine Unit sequencing service with the Applied Biosystems automated sequencer (model 373A). When preparing plasmid DNA for sequencing, one additional phenol:chloroform:isoamyl alcohol (25:24:1) extraction and ethanol precipitation was performed. DNA was resuspended to a final concentration of 500 µg/ml. Sequence data was confirmed by manual dideoxy sequencing using the Sequenase version 2.0 DNA sequencing kit (United States Biochemical, Cleveland, Ohio) and $^{35}$S alpha-labeled dATP (Amersham). DNA was run on a 6% polyacrylamide gel. The gel was dried and autoradiographed on Scientific Imaging Film (Kodak, Rochester, N.Y.) overnight at 70° C.

Analysis of sequence data was performed with the Genetics Computer Group (Version 8.0) sequence analysis software (University of Wisconsin, Madison, Wis.) through the Massachusetts General Hospital Department of Molecular Biology's computer system, FRODO. The homology of the final gene sequence was compared to a national database for peptide and nucleotide sequences at the National Center for Biotechnology Information (Bethesda, Md.) using the Basic Local Alignment Search Tool (BLAST) network service.

Figure 5:
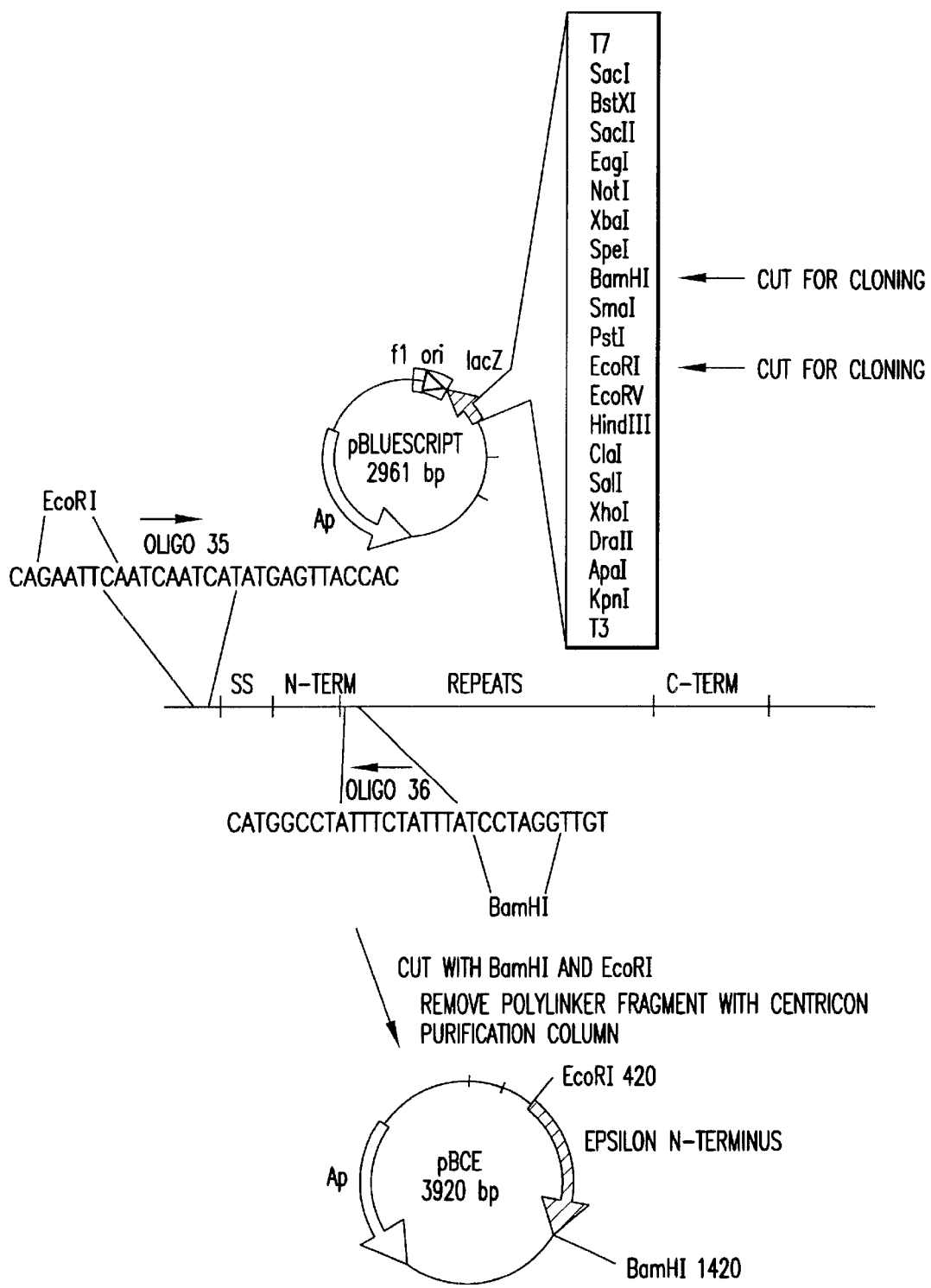
FIG. 5. Cloning strategy for the amino terminus of the C protein epsilon antigen. The amino terminus of the epsilon antigen was cloned using a PCR product as shown. The template for PCR was genomic DNA from the epsilon-positive strain, 515.
Figure 8:
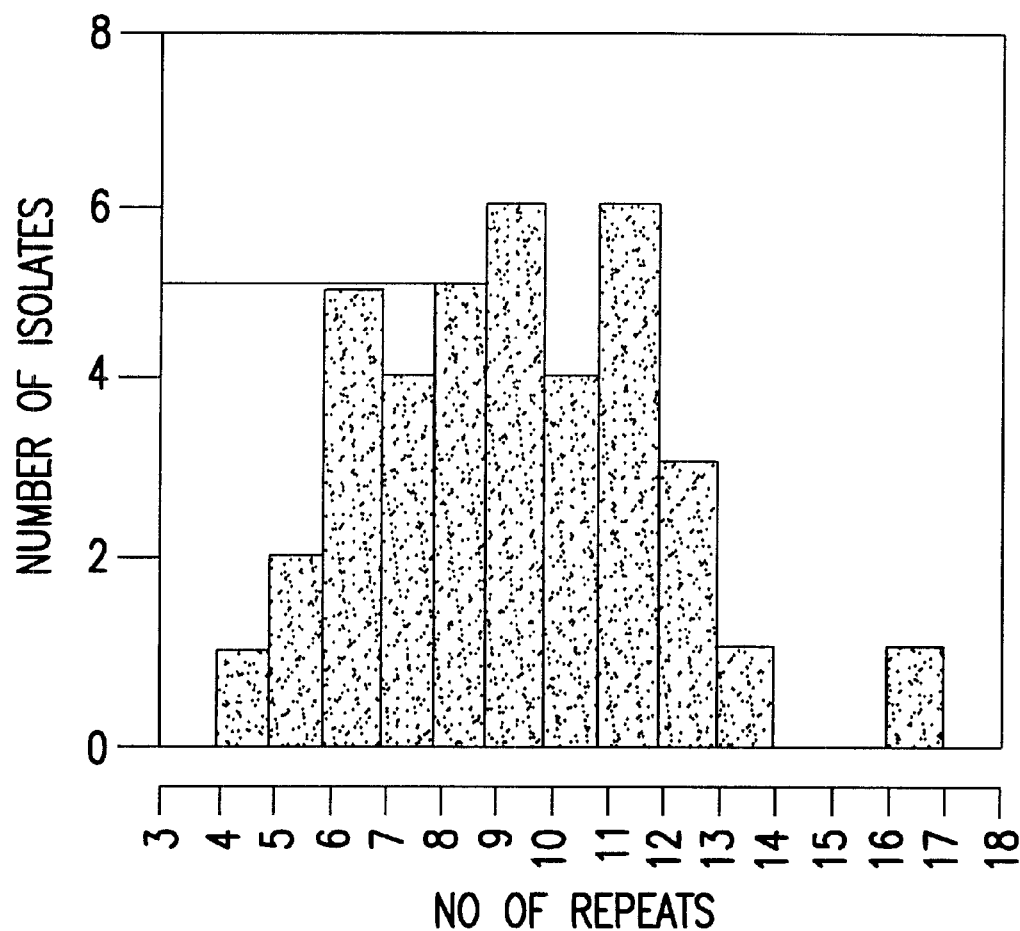
FIG. 8. Distribution of sizes of the repetitive surface antigens alpha and epsilon. 24 strains of GBS expressing the alpha or the epsilon antigen were plotted according to the size of peptide expressed. The chart shows a distribution around 120 kD which corresponds to the size of peptide from the prototype nine repeat peptide.

As shown in FIG. 5, the strategy for cloning the amino terminus of epsilon was based on the hypothesis that the upstream flanking region and the downstream region (the repeats) shared enough homology with those of the alpha antigen that PCR primers designed from the known alpha sequence would amplify the amino terminus of epsilon.

To quantitatively determine the homology of the epsilon and alpha amino termini and to further characterize the unique features of epsilon, the nucleotide sequence of the clone was determined, and it is presented in FIG. 6A (SEQ. ID. NO. 3. Initial sequencing was accomplished by automated sequencing. The variable reproducibility of the results and the abundance of ambiguous nucleotides necessitated confirmation by manual dideoxy sequencing.

As shown in FIG. 7, the nucleotide (SEQ. ID. NOS. 3 and 4) and peptide sequences of epsilon were similar to alpha in the upstream flanking region and the signal sequence. However, in the amino terminus, the divergence between the sequences was significant. For the nucleotide sequence of the entire clone there was 76% homology between epsilon and alpha The amino terminus alone, excluding the flanking DNA and the signal sequence, however, showed only a 65% homology between the sequence of the epsilon clone and the alpha antigen. The amino acid sequence of epsilon has 61% identity with alpha, which drops to only 54% identity if the identical flanking region and signal sequence are removed. This finding is consistent with findings from Southern blot and immunoblot analysis of the epsilon antigen. The amino terminus sequence of epsilon presented here is markedly different at the nucleotide and the amino acid level from that of alpha and supports the importance of epsilon as an independent antigen.

Nucleotide sequencing the unique region of the epsilon antigen also permitted a compositional and structural analysis of the peptide and comparison with the N-terminus of the alpha antigen. The isoelectric point of the epsilon N-terminus was 9.79, whereas the isoelectric point for the alpha N-terminus was 5.19. The markedly different charged state of the two peptides provides further evidence for how they may present different epitopes on the surface of the organism. Furthermore, two-dimensional drawings of protein structure based on Chou-Fasman predictions for peptide folding indicate several domains which are similar between the alpha and epsilon N-termini (see FIG. 10). Epsilon, however, has several distinct domains that are not present in alpha and represent a significant change in the epitopic structure of the antigen. The additional domains on epsilon may explain the failure of alpha N-terminal antiserum to cross-react with epsilon.

The sequence from the clone was used to generate a restriction map of the epsilon antigen amino terminus. Knowledge of the restriction sites will help further characterize the gene and permit the creation of an epsilon-specific nucleotide probe. A restriction map of the amino terminal region of epsilon indicates several changes from alpha. Sites for the restriction enzymes AciI, BsaAI, BssSI, SexAI, SfcI, and SnaBI are present in the epsilon clone, but are not present anywhere in the alpha gene.

To learn about the biological role of the epsilon antigen, the amino terminus sequence was compared to the database of nucleotide and peptide sequences at the National Center for Biotechnology Information using the BLAST network service. As expected, the clone showed significant homology to the C protein alpha antigen of GBS. In addition, homology was noted to other streptococcal protein precursors including those for IgA binding proteins, elongation factors, and muramidase. However, comparison of the nucleotide and amino acid sequences for the amino terminus of epsilon without the flanking region and signal sequence showed homology only to the alpha antigen. The sequence of epsilon presented here provides important insights into the relationship of alpha and epsilon and, more generally, of laddering surface-associated proteins. By identifying common and variable features of the laddering proteins their biological role and function in virulence and immunity may be more clearly understood.

A clone of the amino terminus of epsilon was isolated and sequenced to characterize the unique portion of the gene.

Figure 11:
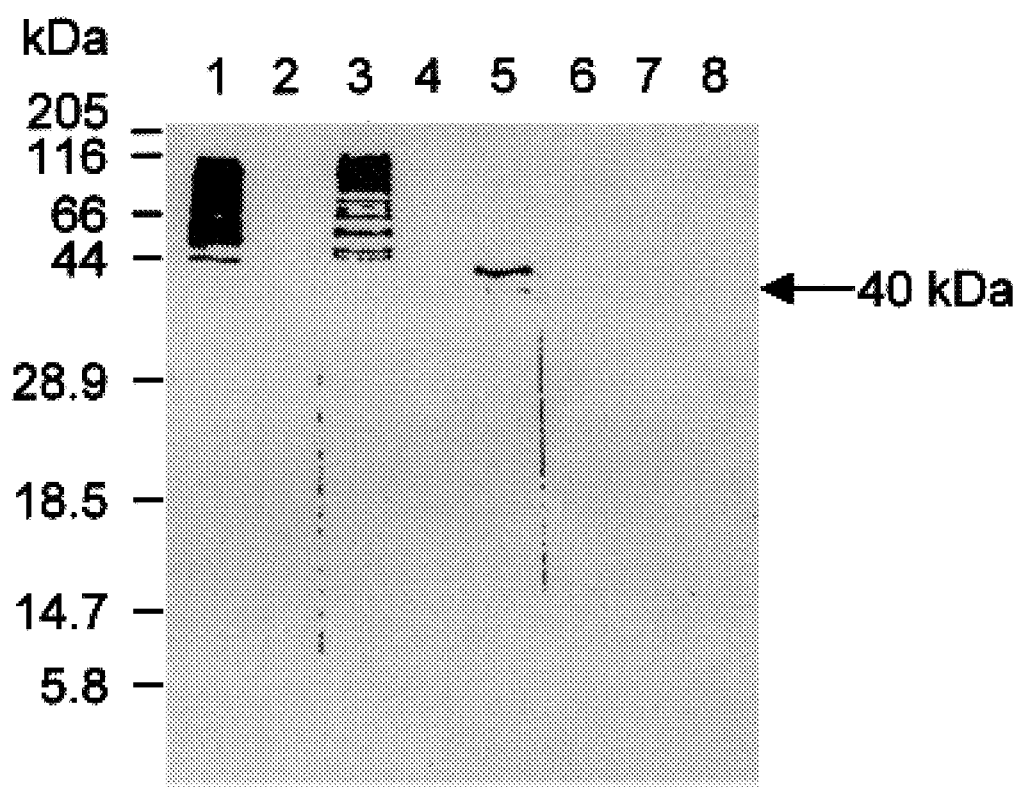
FIG. 11. Detection of epitopes located in the repeat region of the alpha C-protein by monoclonal antibody 4G8. Shown are western blot of extracts of GBS strains A909 (positive control, lane 1) and 090 (negative control, lane 2); E. coli strain DH5α containing pJMS23-1 (positive control, lane 3), pGEM-7Zf(−) (negative control, lane 4); pSKOF1-13 (alpha C-protein repeat region, lane 5); and E. coli strain BL21 (DE3) containing pET24a (negative control, lane 6), pDEK14 (alpha C-protein N-terminus, lane 7), and pDEK15 (alpha C-protein C-terminus, lane 8). Arrow indicates 40-kDa band that corresponds to the expressed gene product from pSKOF1-13.

The amino terminus clone of the epsilon gene has shown conclusively that epsilon and alpha antigen genes differ significantly at the nucleotide level. The start site and signal sequence of both genes are similar. However the majority of the amino terminus of epsilon shares little homology with alpha. Subcloning the epsilon amino terminus clone into an *E. coli* expression vector with a histidine tag will allow for the purification of epsilon amino terminus peptide. This peptide can be used to immunize rabbits and raise epsilon-specific antiserum that should identify epsilon on immunoblot. If this antiserum is cross-protective with strains expressing other surface-associated antigens, it may play. an important role in vaccine development. With the sequence presented here, it will be possible to learn more about the relationship between laddering surface proteins and about the nature of the evolutionary split that led to the production of the related, but mutually exclusive, alpha and epsilon antigens. Comparing common and distinct features of the alpha and epsilon genes may lead to a more clear understanding of their role in virulence and immunity. Only by sequencing the repeat region of epsilon can it be determined whether there are any differences with the repeat region in alpha. In addition, a full-length clone can be expressed and purified to raise epsilon-specific antibodies for protection studies or to covalently link with type-specific polysaccharide as a conjugate vaccine.

The biological role of surface-associated proteins in virulence and immunity is not well characterized. Discovery of strains with silent genes for surface antigens and strains with no surface antigen expression invites further inquiry into regulation and expression. Studying the role of immunogenic surface proteins on GBS is important to understanding the pathogenesis of the organism and may lead to the development of a polyvalent conjugate vaccine incorporating protein antigens.

A new surface protein antigen of GBS has been identified, sequenced, and characterized. This represents a significant advance, not only in the knowledge of surface protein structure, but also in the design of biological tools and techniques that may be used in the future to study surface proteins genetically and immunologically. Epsilon, has been defined and its relationship to other related proteins established. This has generated a new understanding about the role of surface-associated proteins in the immune response to GBS.

Discussion

In analyzing the phenotypic and genotypic diversity of the C-protein alpha antigen of GBS, it was found that the heterogenous ladder of peptide fragments comprising the alpha antigen is coded for by only one gene in the bacterium and that the size of the largest peptide fragment in the ladder was a consequence of the size of the alpha antigen gene and in particular, the size of the repeat region within that gene. Three novel sources of antigenic diversity in the C-protein alpha antigen were identified. Additionally, the epsilon antigen which is related to the alpha antigen was identified and cloned that is distinguishable by its different N-terminal.

The tandem repeats within the repeat region of the alpha antigen gene are the primary source of diversity in the C-protein alpha antigen. For the panel of strains analyzed, the size of the repeat region in bca varied by as much as 7 kb between strains, and protein size varied by as much as 200,000 Da. When the biological function of C-protein alpha antigen becomes more well defined, it will be possible to better appreciate these differences in terms of their effects upon biological function.

The two properties that have been ascribed to the alpha antigen are the ability to resist phagocytosis and the ability to elicit protective antibodies (Madoff, L. C., et al., *Infect Immun* 59(1):204–210 (1991);Madoff, L. C., et al., *Infect Immun* 59(1):204–210 (1991);Michel, J. L., et al., *Infect Immun* 59(6):2023–2028 (1991)). However, there are other biological functions of the alpha C-protein that have not yet been defined. One can imagine that a strain encoding an alpha antigen of almost 200,000 Da would be extremely sensitive to killing in the presence of specific antibody. Clearly there must be some function of the repeats that makes it beneficial for some strains to include a large repeat region within their alpha C-proteins. To look for possible answers to this question, one can first examine the role that repeating units play in the surface-associated proteins of other gram-positive cocci. Repeat regions in the M protein of group A Streptococcus for example are able to rearrange spontaneously, generating antigenic diversity by changing the peptide sequence and number of repeats (Hollinghead et al, *Mol. Gen. Genet* 207:196–203, (1987)). It has not been shown that changing numbers of repeats within the alpha antigen can change its protective epitopes, but if this were possible, it could be a reason for the maintenance of large numbers of repeats within the gene.

The unique amino terminus of the epsilon antigen was cloned and sequenced. The sequencing indicated a large area of divergence from the alpha antigen. The results have important implications for understanding the biological role of surface-associated proteins and for incorporating them into experimental vaccines.

EXAMPLE 8

Expression of the Recombinant Alpha C-protein N- and C-terminal Peptides

The alpha C-protein monoclonal antibody 4G8 binds a protective epitope of the alpha C protein (Madoff, L. C., et al, *Infect. Immun.* 59:204–210 (I991)). To map the location of this epitope, plasmid constructs consisting of the N-terminus, repeat region, and C-terminus were cloned and expressed in *E. coli*.

Methods

Bacterial strains, plasmids, and media. For this Example as well as Examples 9–14 the following bacterial strains, plasmids and media were used. Bacterial strains used in this study included GBS strains A909 and 090 (Lancefield, R. C., et al., *J. Exp. Med.* 142:165–179 (1975)) and *E. coli* strains BL21(DE3) (Grodberg, J. & Dunn, J. J., *J. Bacteriol.* 170:1245–1253 (1988)), DH5a (Gibco/BRL, Bethesda, Md.), and NK8032 (kindly provided by Dr. Nancy Kleckner). Alpha C-protein subclones pJMS23-1 and pJMS23-9 have been described (Michel, J. L., et al., *Infect. Immun.* 59:2023–2028 (1991); Michel, J. L., et al., *Proc. Natl. Acad. Sci. USA*. 89:10060–10064 (1992)), and plasmids pSKOF1-13, pDEK14, and pDEK15 are described below. Plasmid vectors included pET24a (Novagen, Madison, Wis.) and pGEM-7Zf(−) (Promega, Madison, Wis.). GBS strains were grown in Todd-Hewitt broth (Difco, Detroit, Mich.) and on tryptose soy agar (TSA) with 5% sheep's blood plates (Becton Dickinson, Woburn, Mass.). *E. coli* strains were grown in L-broth (Difco). Antibiotic concentrations were: ampicillin (100 $\mu$g/ml) and kanamycin (50 $\mu$g/ml).

DNA procedures/Subclones of the bca gene. Restriction endonucleases, ligases, and calf-intestine alkaline-phosphatase were obtained from New England Biolabs (Beverly, Mass.) and Boehringer Mannheim (Indianapolis, Ind.). Staggered-end ligations were carried out at 14° C. (Tabor, S. in *Current Protocols in Molecular Biology*, Vol. 1, F. M., Ausubel, et al., (eds.), John Wiley & Sons, Inc., New York, (1994), pp. 3.14.3–3.14.4). Plasmids used in this study are shown in FIG. 11. pSKOF1-13, containing a 1.24-kb insert consisting of tandem repeats, was developed by digesting pJMS23-9, first with HindIII and NsiI and then with exonuclease III (Michel, J. L., et al., *Proc. Natl. Acad. Sci. USA*. 89:10060–10064 (1992)). pSKOF1-13 encodes 11 amino acids of the C-terminal partial repeat and the first amino acid from the C-terminus expressed from the lacZ promoter of the pGEM-7Zf(−) vector. The gene product expressed from pSKOF1-13 contains the alpha C-protein repeat region and a single amino acid of the C-terminus.

The DNA encoding the alpha C-protein N- and C-termini were PCR cloned into a pET24a overexpression vector containing a T7 polymerase promoter that facilitates isopropyl-§-D-thiogalactosidase (IPTG)-inducible, high-level expression of the recombinant gene fragment and a C-terminal six-residue histidine tag that supports purification of the gene products by $Ni^{2+}$ affinity chromatography. Oligonucleotide preparations for PCR were synthesized at an institutional core facility with the Expedite Nucleic Acid Synthesis System, Model 8909 (Millipore Corp., Bedford, Mass.). The DNA sequence encoding the alpha C-protein N-terminus was amplified from the bca gene subclone pJMS23 −1 by PCR with the following oligonucleotide primers (SEQ. ID. NOS. 11 and 12):

5'-GTATATGGATCCATAGTTGCTGCATCTACA-3' and

5'-GGGCTGAAGCTTCAATACTAACAATTTCTC-3'.

The oligonucleotide primers (SEQ. ID. NOS. 13 and 14), used to amplify the DNA encoding the alpha C-protein C-terminus are:

5'-GTATATGGATCCAAAGCTCAGCAAGTCAAC-3' and

5'-GGGCTGAAGCTTATCCTCTTTTTTCTTAGA AAC-3'.

Conditions of the amplification were as follows: denaturation, 3 min at 94° C.; annealing, 2 min at 39° C.; and polymerization, 3 min at 72° C. Amplification was carried out with a Vent polymerase kit, with 1.5 mM $MgCl_2$ (New England Biolabs). The BamHI and HindIII restriction endonuclease sites (underlined) were encoded in the primers to facilitate cloning into the pET24a vector.

A 542-bp fragment was amplified with the N-terminal-specific primers by PCR from pJMS23-1 and ligated into the BamHI- and HindIII-digested pET24a vector. Plasmid pDEK14 (FIG. 9) contained such a 542-bp insert and was verified to encode the alpha C-protein N-terminus by partial nucleotide sequence analysis. With C-terminal-specific primers, a 144-bp fragment was amplified from pJMS23-1 and ligated into the pET24a vector. Recombinant clones were screened by colony-blot hybridization and probed with the amplified C-terminal PCR product; insert size was determined by digestion with BamHI and HindIII. Plasmid pDEK15 (FIG. 9) contained a 135-bp fragment encoding the alpha C-protein C-terminus as confirmed by nucleotide sequence. Colony-blot hybridization for *E. coli*. Colony-blot hybridization was carried out as described previously (Weis, J. H. in *Current Protocols in Molecular Biology*, Vol. 1, F. M., Ausubel, et al., (eds.), John Wiley & Sons, Inc., New York, (1994), pp. 6.2.1–6.2.3). The amplified PCR fragments were labeled by random priming reaction with $^{32}P$-dCTP (Amersham, Arlington Heights, Ill.) with use of a Random Priming kit (Boehringer Mannheim). The labeled probes were separated from unincorporated nucleotides on NucTrap columns (Stratagene, La Jolla, Calif.).

Figure 9:
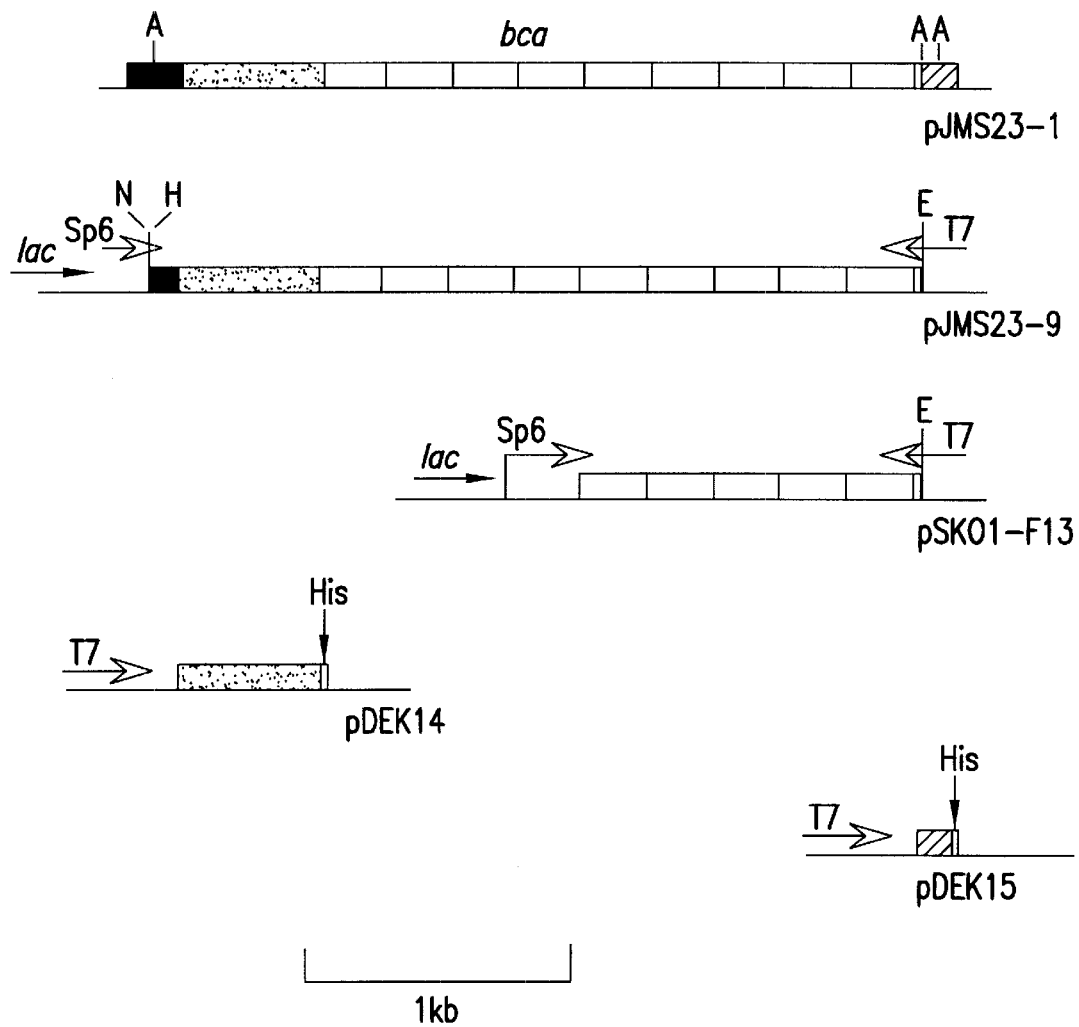
Figure 10:
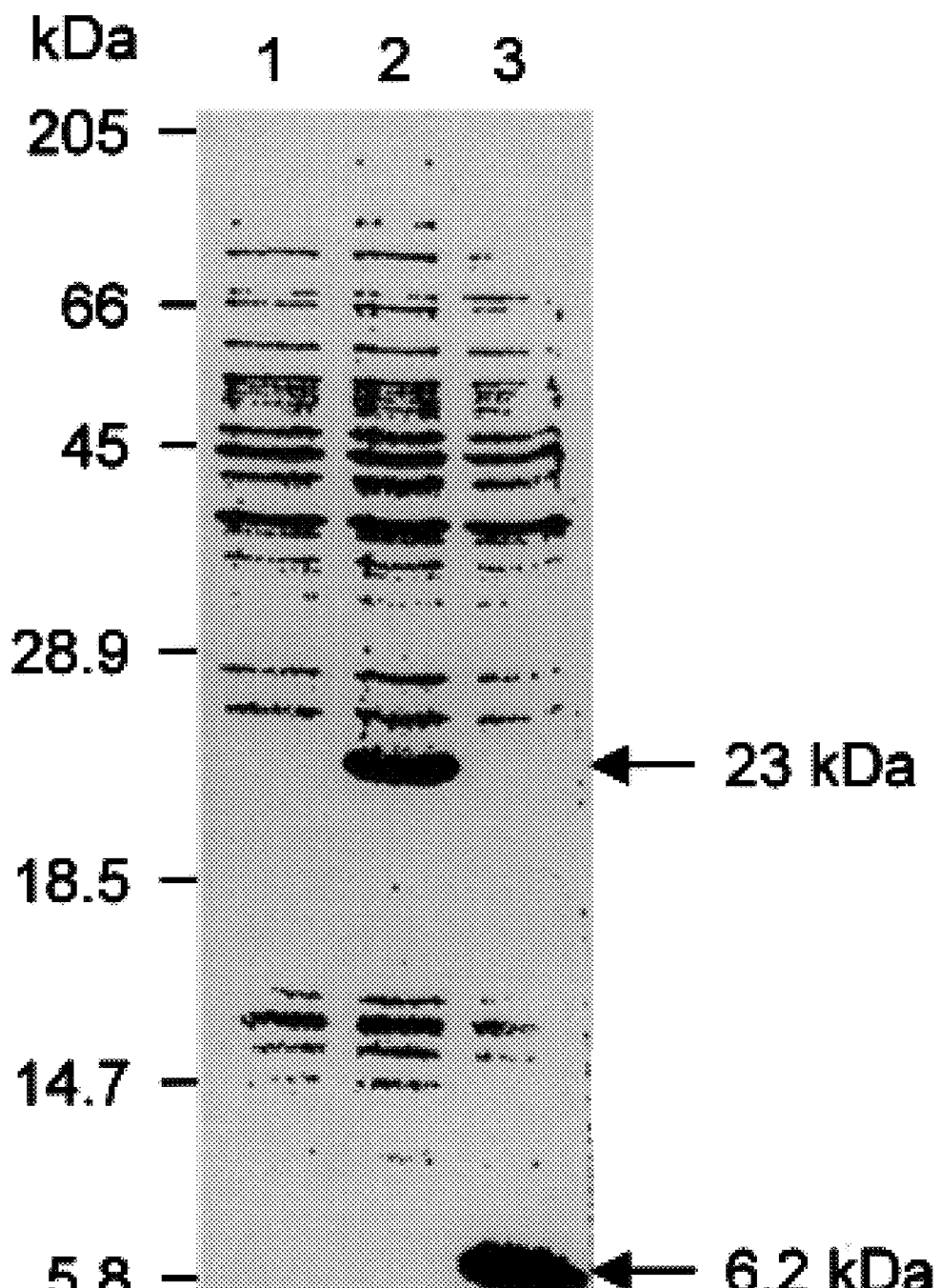
FIG. 10. Expression of the alpha C-protein N- and C-termini. As seen in Coomassie-stained 15% polyacrylamide gel of extracts of *E. coli* strain BL21(DE3) containing pET24a (lane 1), pDEK14 (lane 2), and pDEK15 (lane 3) after induction with IPTG. Arrows indicate a 23-kDa peptide that corresponds to the N-terminal fragment and a 10-kDa peptide that corresponds to the C-terminal fragment.

FIG. 9 shows the subclones of the, bca gene that were used to map the protective epitope. PAGE was used to characterize the expressed gene products from the N- and C-terminal clones. Extracts of strain BL21(DE3) containing pET24a (negative control), pDEK14 (N-terminal clone), and pDEK15 (C-terminal clone) were prepared after IPTG induction and electrophoresed on 15% polyacrylamide gels. FIG. 10 shows a band of ~23 kDa (the expected size of the N-terminal fragment) in the lane corresponding to the extract of *E. coli* containing pDEK14 (lane 2). Lane 3 shows a 6.2-kDa band in the *E. coli* extract containing pDEK15, which is similar to the expected size of the recombinant alpha C-protein C-terminal peptide.

EXAMPLE 9

Localization of the Protective Epitope(s) Defined by 4G8

Western blot analysis was used to determine whether the epitope bound by 4G8 is localized to the N-terminus, repeat region, or C-terminus of the alpha C protein.
Methods
SDS/polyacrylamide gel electrophoresis (PAGE), western immunoblotting, and antibodies. Proteins were analyzed on SDS/PAGE (8% and 15%), with both Coomassie blue straining and western immunoblots by standard methods (Gallagher, S. A. & Smith, J. A. in *Current Protocols in Molecular Biology*, Vol. 2. F. M. Ausubel, et al., (eds.), John Wiley & Sons, Inc., New York, (1994), pp. 10.2.1–10.2.21; Sasse, J. in *Current Protocols in Molecular Biology*, Vol. 2, F. M., Ausubel, et al., (eds.), John Wiley & Sons, Inc., New York, (1994), p. 10.6.1–10.6.8) Primary antibodies and secondary alkaline-phosphatase conjugates (Organon Teknika, West Chester, Pa.) were used at a dilution of 1/1000. Blots were developed with alkaline-phosphatase substrate buffer (Sigma, St. Louis, Mo.). Antibodies used in this study include polyclonal alpha C-protein antibodies (Gravekamp, C., et al., *Infect. Immun.* 64:3576–3583 (1996)), alpha C-protein N-terminal antibodies (Kling et al., *Inf. Immun.* (In press, April 1997)), and the alpha C-protein monoclonal antibody 4G8 (Madoff, L. C., et al., *Infect. Immun.* 59:204–210 (1991)).

FIG. 11 shows a series of bands ranging in size from 27 to 40 kDa in the *E. coli* extract containing pSKOF1-13 (tandem repeat region) but not in the extracts of *E. coli* carrying pDEK14 (N-terminus) or pDEK15 (C-terminus). The top band (40 kDa) corresponds approximately to the expected size of the recombinant gene product (45 kDa). These data indicate that 4G8 specifically detects an epitope in the tandem repeat region of the alpha antigen. Bands ranging in size from 34- to 95-kDa are found in GBS strain A909 (as a positive control for alpha C-protein expression) but not in 090 (negative control). This result is similar to the previously observed size range of the alpha C-protein bands from A909 (36 to 116 kDa) (Madoff, L. C., et al., *Infect. Immun.* 59:204–210 (1991)). In addition, bands ranging from 32 to 105 kDa are detected in the extract of *E. coli* containing pJMS23-1. These bands correspond to the approximate sizes of the recombinant alpha C protein (40 to 120 kDa) (Michel, J. L., et al., *Infect. Immun.* 59:2023–2028 (1991)). No bands are detected in the *E. coli* extracts carrying pGEM-7Zf(−) or pET24a (negative controls). Thus, 4G8 detects the alpha C protein from both the native antigen (A909) and the recombinant antigen (pJMS23-1) (Madoff, L. C., et al., *Infect. Immun.* 59:204–210 (1991); Michel, J. L., et al., *Infect. Immun.* 59:2023–2028 (1991)). These data indicate that 4G8 does not bind either terminus and is specific for the alpha C-protein tandem repeat region.

EXAMPLE 10

ELISA Inhibition

ELISA inhibition was used to study the relationship between the relative affinity of monoclonal antibody 4G8 and the numbers of repeats expressed by alpha C protein.

Methods

Development of alpha C-protein N-terminal specific antibodies. To obtain alpha C-protein N-terminal-specific antibodies, purified alpha C-protein N-terminal peptides were lyophilized and sent to Lampire Biologicals (Malvern, Pa.) for rabbit immunization: 100 μg of the alpha C-protein N-terminal peptide was resuspended in 2.5 ml of PBS, emulsified in 2.5 ml of complete Freund's adjuvant, and injected subcutaneously at 6 sites on day 1. Booster immunizations given at 21 and 42 days consisted of solubilized antigen, emulsified with incomplete Freund's adjuvant. Blood was drawn on days 1 (preimmunization bleed), 21, and 42 for antibody testing. At day 56, a 50-ml blood sample was drawn (postimmunization bleed).

Titers of the mouse monoclonal antibody 4G8 and rabbit antiserum elicited to the alpha C-protein N-terminal peptide were measured by ELISA inhibition (Gravekamp, C., et al., Infect. Immun. 64:3576–3583 (1996)).

Figure 12:
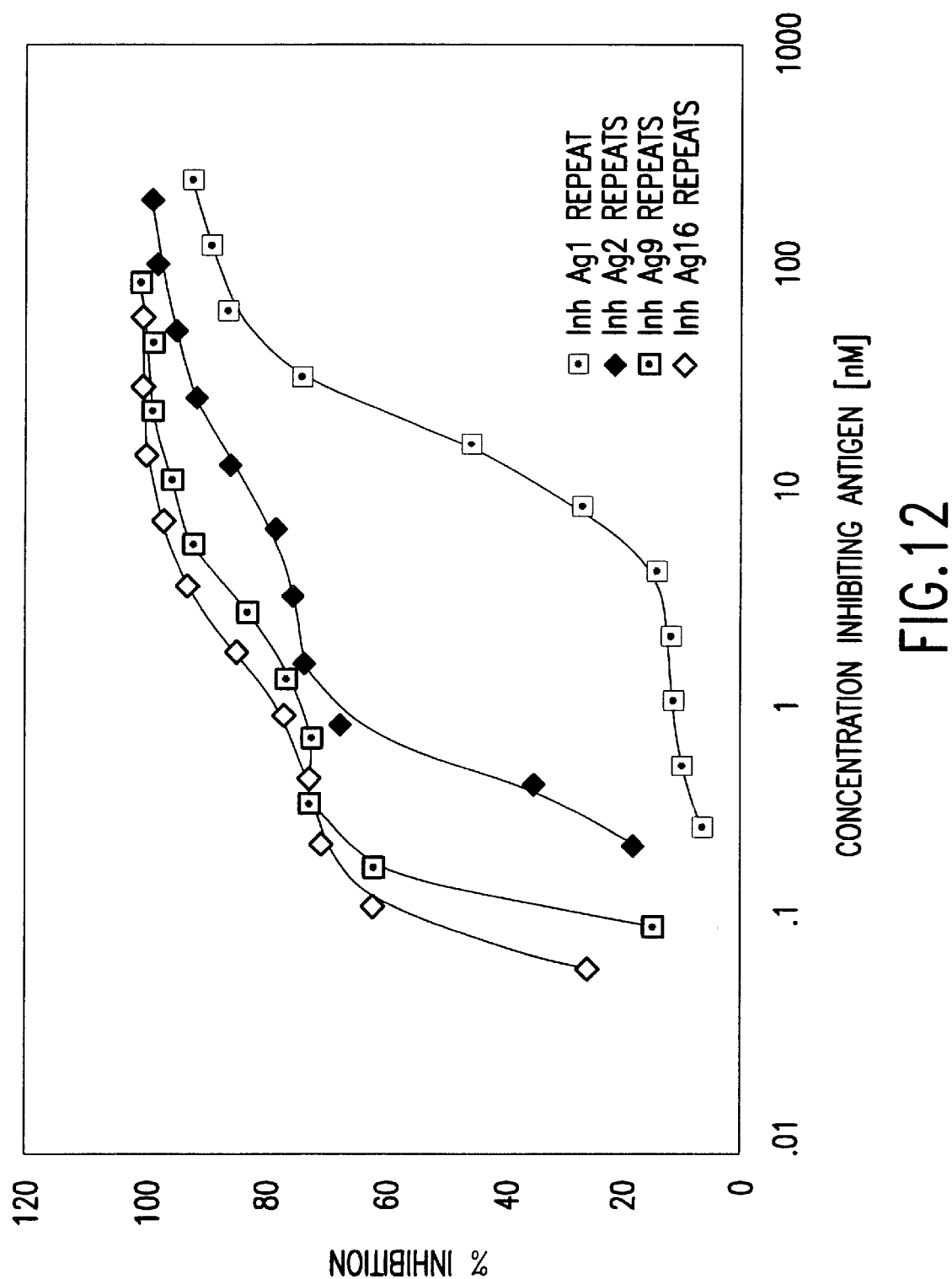
FIG. 12. ELISA inhibition. Relative binding affinities of monoclonal antibody 4G8 to purified alpha C proteins with 1, 2, 9, and 16 repeats are shown. Plates were coated with 9-repeat alpha C protein (0.125 μg/ml). 4G8 was used as the primary antibody (dilution 1:8,000), and alkaline phosphatase-conjugated antibody to rabbit IgG Fc (1:2,000) was used as the secondary antibody. Two-fold dilutions were made of 1-, 2-, 9-, and 16-repeat alpha C protein, and used as inhibiting antigen (starting dilution 5 μg/ml).

FIG. 12 indicates that a 40-, 133-, and 222-fold higher concentration of 1-repeat antigen was required than of 2-, 9-, and 16-repeat antigens, respectively, to obtain 50% inhibition of antigen-antibody binding. These data show a high affinity of 4G8 for 2-, 9-, and 16-repeat alpha C protein, but a much lower affinity for the 1-repeat alpha C protein. These data are similar to results of other studies of the effects of repeat number on antibody binding (Gravekamp, C., et al., Infect. Immun. 64:3576–3583 (1996)).

EXAMPLE 11

Purification of the Alpha C-protein N-terminal Peptide

The N-terminal peptide expressed from E. coli was purified by $Ni^{2+}$ affinity chromatography.

Methods $Ni^{2+}$-affinity chromatography. The recombinant alpha C-protein N-terminal peptide was purified with a $Ni^{2+}$ affinity column according to the Novagen pET system manual. Eluted fractions containing the largest amounts of protein were identified by Bradford assay (Smith, J. A., in Current Protocols in Molecular Biology, Vol. 2, F. M. Ausubel, et al., (eds.) John Wiley & Sons, Inc., New York, (1994), pp. 10.1.1–10.1.3) and desalted with an Amicon microconcentrator, P-10,000 molecular weight cutoff.

Figure 13A:
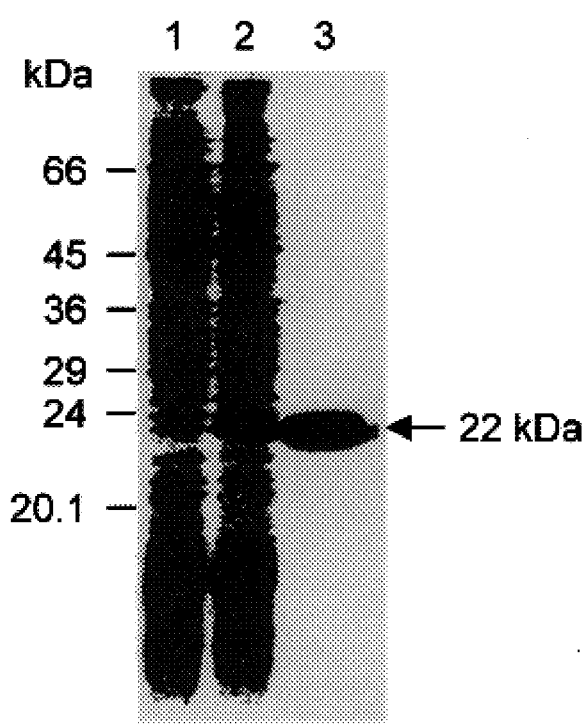
FIGS. 13A–13B.

FIG. 13A shows a Coomassie-stained polyacrylamide gel of the cell extracts of E. coli (BL21/DE3) containing pDEK14- before and after induction with IPTG, as well as a sample of the eluate from the $Ni^{2+}$ column (lane 3). A single 22-kDa band is seen in the eluate from the $Ni^{2+}$ column which demonstrates that the recombinant alpha C-protein N-terminal peptide was successfully induced, expressed, and purified by $Ni^{2+}$ affinity chromatography.

EXAMPLE 12

Raising Antibodies to the Recombinant Alpha C-protein N-terminal Peptide

Antibodies were raised in rabbits to the recombinant $Ni^{2+}$ purified N-terminal peptide. Western blot analysis of the postimmunization serum specifically detected a band of ~22 kDa, in the extract of E. coli carrying pDEK14 after induction with IPTG, that corresponds to the expected size of the N-terminal peptide (data not shown). An ELISA was used to quantitate the titer of the N-terminal antiserum. Titers of antiserum were found to be high, in excess of a 1/102,400 fold dilution.

Figure 13B:
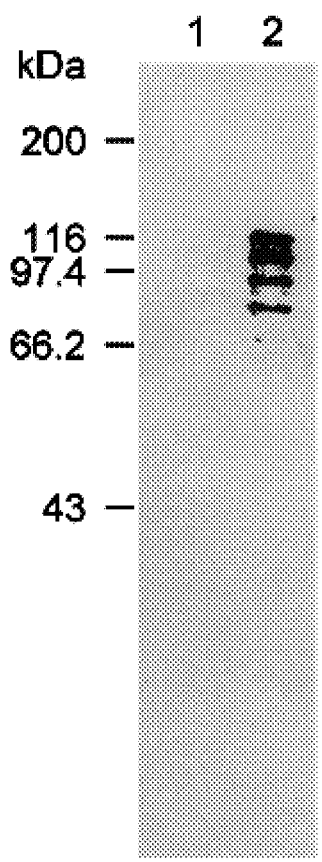

Western blot analysis was used to determine whether antibodies specific for the alpha C-protein N-terminus can bind the native protein. FIG. 13B shows a ladder pattern of bands with a size range from 36 to 116 kDa detected in extracts prepared from GBS strain A909 but not from strain 090 (negative control) probed with the postimmunization serum. This ladder pattern corresponds to the expected size range of the alpha C-protein bands (Madoff, L. C., et al., Infect. Immun. 59:2638–2644 (1991)). Thus, alpha C-protein N-terminal antiserum can detect native alpha C protein.

EXAMPLE 13

Opsonophagocytosis Assay Using Alpha C-protein N-terminal-specific Antibodies

An in vitro opsonophagocytosis assay was used to determine whether alpha C-protein N-terminal antibodies are opsonic for GBS (Gallagher, S. A. & Smith, J. A. in Current Protocols in Molecular Biology, Vol. 2. F. M. Ausubel, et al., (eds.), John Wiley & Sons, Inc., New York, (1994), pp. 10.2.1–10.2.21).

Methods

The opsonophagocytosis assay to determine the functionality of the alpha C-protein N-terminal-specific antibodies was carried out as described (Baltimore, R. S., et al., J. Immunol. 118:673–678 (1977)). This assay requires human serum (used as a complement source), GBS ($\sim 1.5 \times 10^6$ CFU), polymorphonucleocytes (PMNs) ($\sim 3.0 \times 10^6$ cells), and antibodies (final dilution 1/100) combined in a 500-_1 volume. -The amount of opsonophagocytic killing (log-kill) was determined by subtracting the log of the number of colonies surviving the 1-hr assay from the log of the number of CFU at the zero time point.

Figure 14:
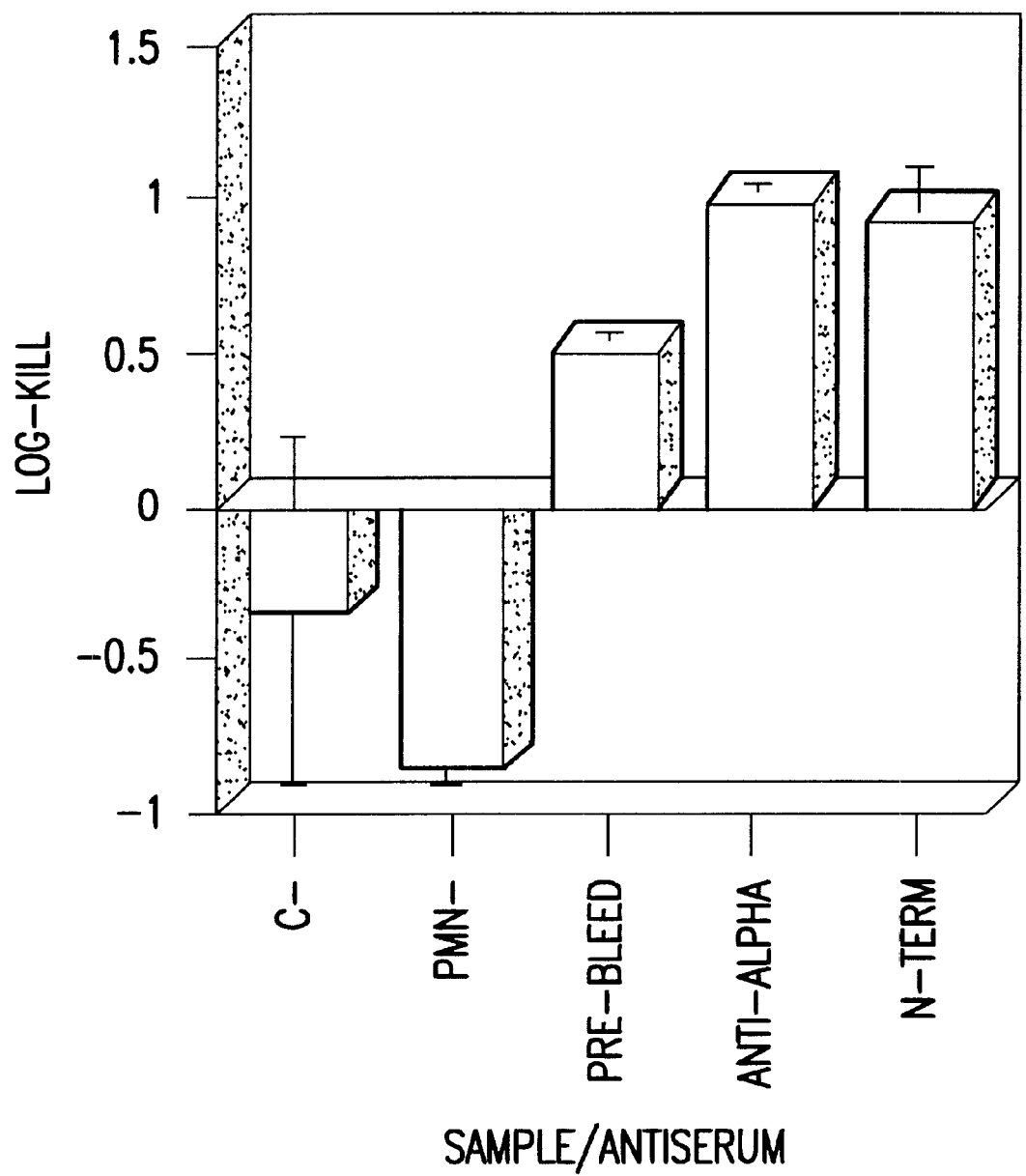
FIG. 14. Opsonophagocytosis Assay. Results of an opsono-phagocytosis assay used to determine whether alpha C-protein N-terminal antibodies were opsonic. Negative controls included the presence of heat-killed complement (c−), the absence of PMN (PMN-), and preimmunization sera (pre-bleed). Polyclonal antibodies to the alpha C-protein (anti-alpha). Polyclonal antibodies (anti-alpha) served as the positive control. Opsonization is expressed as log-kill: the log number of GBS at start of the assay minus the log number of GBS after 1 hr of incubation.

FIG. 14 shows that the postimmunzation antiserum kills approximately 0.6-log more GBS than the preimmunization serum; this degree of killing is comparable to that by antiserum raised to the whole recombinant molecule (alpha C-protein polyclonal serum). As expected; no killing is observed when PMNs are not added or when heat-killed complement is used. These data demonstrate that alpha C-protein N-terminal-specific antibodies are opsonic for GBS.

EXAMPLE 14

Mouse Protection by Alpha C-protein N-terminal-Specific Antibodies

A mouse protection study was conducted to determine whether alpha C-protein N-terminal-specific antibodies can protect neonatal mice against infection with alpha C-protein-bearing strains of GBS. Pregnant dams were passively immunized with postimmunization rabbit antiserum raised to the N-terminal, preimmunization rabbit serum, (negative control), and rabbit antiserum to the Ia-TT protein-capsular-polysaccharide conjugate (positive control) (Wessels, M. R., et al., Infect. Immun. 61:4760–4766 (1993)).

Neonatal mouse model. The following is a modification of the neonatal mouse model described by Rodewald et al. (Rodewald, A. K., et al., J. Infect. Dis. 166:635–639 (1992)). CD-1 outbred mice arrived 17- to 18-days pregnant (Charles River Laboratories). The second day after arrival mice were divided into three groups with 4 pregnant mice per group. The mice were immunized intraperitoneally with 0.5 ml of the postimmunization antiserum raised to the N-terminal polypeptide, preimmunization serum, or antiserum raised to a protein-polysaccharide conjugate consisting of the Ia capsular polysaccharide covalently coupled to tetanus toxoid (Ia-TT) (Wästfelt, M., et al., *J. Biol. Chem.* 271:18892–18897 (1996)). Newborn mouse pups were challenged with 3×10⁴ CFU of GBS strain A909 by intraperitoneal injection. After 48 hours, numbers of dead and surviving mice were counted.

Table 2 shows that 69% of the mice immunized with N-terminal antibodies survived challenge with GBS strain A909, whereas only 15% of those immunized with the preimmunization serum survived. This protection was significant (P<0.0001, Fisher's exact test). These results show that the alpha C-protein N-terminal antibodies are significantly more protective than control serum. Therefore, the alpha C-protein N-terminus contains a protective epitope.

TABLE 2

Passive protection of neonatal mice with N-terminal-specific antibodies to GBS.

| Antiserum | Number of pups (alive/total) | % Survival |
|---|---|---|
| Ia-TT[a] | 45/46 | 98 |
| preimmunization[b] | 6/39 | 15 |
| N-terminal | 29/42[c] | 69 |

[a]Positive control (GBS Ia polysaccharide conjugated to tetanus toxoid)
[b]Negative control
[c]P < 0.0001 compared with the preimmunization serum by Fisher's exact test.

DISCUSSION OF EXAMPLES 11–14

The alpha and presumably the epsilon C protein of GBS are surface-associated proteins that are thought to play a role in the virulence of and immunity to GBS. The different structural domains of the alpha C protein, the N-terminus, repeat region, and C-terminus, may have different biological and immunologic properties. It is assumed that this is also true for the epsilon antigen.

Thus, either in a conjugated or non-conjugated form, the different structural domains (e.g. the C or N-terminal regions) of the alpha, beta or epsilon antigens either individually or in various combinations with each other may be used to make vaccines against GBS. In order to develop a conjugate vaccine to protect against alpha C-protein-bearing strains, the opsonic and protective epitopes of the antigen were initially mapped. Epitopes of the alpha C protein that are both opsonic and protective have now been localized to the repeat region and the N-terminus of the alpha C-protein.

Clearly, there is a divergence between the N-termini of the alpha and epsilon C-proteins. Studies of other surface-associated proteins of group B Streptococcus that have repetitive sequences (e.g., Rib, epsilon, and type V strains) suggest that there is also divergence from the alpha antigen in the N-terminal (Beseth, B. D., A genetic analysis of phenotypic diversity of the C protein alpha antigen of group B Streptococcus, Bachelor of Arts thesis in Biology, Harvard College, (1992); DuBois, N. B. Genetic and phenotypic properties of the surface proteins of group B Streptococcus and the identification of a new protein, Bachelor of Arts thesis in Biology, Harvard College, (1995); Lachenauer, C. S. & L. C. Madoff, *Infect. Immun.* 64:42554260 (1996); Wästfelt, M., et al., *J. Biol. Chem.* 271:18892–18897 (1996)).

To determine whether the alpha C-protein N-terminus contained protective epitopes, specific antibodies to the N-terminus were raised that conferred passive protection against alpha C-protein-bearing strains in a neonatal mouse model. It is interesting that specific antibodies to the alpha C-protein N-terminus conferred 70% passive-protection, whereas the polyclonal antibodies to the 9-repeat alpha C protein conferred 41% passive protection (Gravekamp, C., et al., *Infect. Immun.* 64:3576–3583 (1996)). However, polyclonal antibodies elicited to recombinant 1- or 2- repeat alpha C proteins give greater than 75% protection (Gravekamp, C., et al., *Infect. Immun.* 64:3576–3583 (1996)). Hypothetically, antibodies directed at the full-length alpha or epsilon C protein might select for deletions within the repeat region.

A mouse model of GBS infection was used to determine whether alpha C-protein tandem repeat deletion mutants were selected in vivo (Madoff, L. C., et al., *Proc. Natl. Acad. Sci. USA.* 93:4131–4136 (1996)). Mice immunized with antibodies to the alpha C protein were challenged with GBS strains expressing the alpha C protein. The size of the alpha C protein in strains of GBS isolated from the spleens of the mice was determined by western blot analysis. Fifty percent of the recovered GBS strains expressed truncated forms of the alpha C protein, a result suggesting the selection of deletion mutants within the repeat region of the bca gene in the presence of alpha C-protein antibodies. Because these mutants were isolated at a relatively high frequency, they may have been protected against opsonophagocytosis by the alpha C-protein antibodies.

In an in vitro opsonophagocytosis assay, strains of GBS with deletions in the bca gene were killed less frequently than parental strains by antibodies to the full-length alpha C-protein (Madoff, L. C., et al., *Proc. Natl. Acad. Sci. USA.* 93:4131–4136 (1996)). This apparent lesser susceptibility to opsonization may be explained by fewer tandem repeat epitopes than are present in strains with a full-length alpha C-protein. In addition to being fewer in number, the alpha C-protein protective epitopes may be conformational, and deletion mutants may express fewer alpha C-protein epitopes. By ELISA inhibition the affinity for recombinant alpha C proteins containing a single repeat is reduced compared with that of recombinant proteins containing larger numbers of repeats (Gravekamp, C., et al., *Infect. Immun.* 64:3576–3583 (1996)). These antibodies recognize epitopes expressed by proteins containing more repeats (9 or 16) but lose their overall binding affinity for epitopes expressed by proteins containing fewer repeats (1 or 2).

These observations support the possibility that the epitopes of the alpha C-protein tandem repeat region are conformational. Alternatively, the reduced affinity for the single repeat recombinant protein can also be explained if the recombinant alpha C protein is proteolytically processed. Thus, the 1-repeat recombinant protein may lose repeat-region epitopes due to proteolytic processing within the single repeat and have a reduced ability to inhibit antibody binding to these epitopes. In contrast to epitopes within the repeat region, the N-terminal epitopes are conserved in both parental and deletion mutant strains of GBS strain A909, and these mutants are susceptible to opsonophagocytosis with N-terminal antiserum (Madoff, L. C., et al., *Proc. Natl. Acad. Sci. USA.* 93:4131–4136 (1996)). Therefore, the recombinant alpha and epsilon C-protein N-terminus are prime candidates for use in a protein-polysaccharide conjugate vaccine.

The protective monoclonal antibody 4G8 was localized to the repeat region of the alpha C protein (Madoff, L. C., et al., *Infect. Immun.* 59:204–210 (1991)). Attempts to further localize the epitope bound by 4G8 within the repeat region have not been successful. Our unpublished studies using synthetic peptides corresponding to overlapping 10-amino acid segments within the alpha C-protein repeats did not reveal a binding site for 4G8. The inability to define a peptide binding site for 4G8 on the alpha C-protein could be explained if the site detected by 4G8 were a conformational epitope or if the binding site contains noncontiguous segments from within the repeat region.

Protective epitopes have been mapped within the closely related M protein of group A Streptococcus (GAS) (Beachey, E. H., et al., *J. Exp. Med.* 166:647–656 (1987)). In studies assessing whether protective epitopes were localized to the N-terminal half, the N-terminus of the M-protein was liberated from the cell wall of GAS by pepsin cleavage. Antibodies were raised to the isolated pepsin-cleaved N-terminal fragments (pepM) (Beachey, E. H., et al., *J. Exp. Med.* 150:862–877 (1979)). Such antibodies have been demonstrated to be opsonic and protective in studies of several M proteins (Kehoe, M. A., Vaccine 9:797–806 (1991)). Protective epitopes of the M5, M6, and M24 proteins were mapped to the extreme N-terminal regions of the mature proteins (Beachey, E. H., et al., *J. Exp. Med.* 166:647–656 (1987)), and a synthetic peptide vaccine consisting of these epitopes was developed. This vaccine elicited opsonic antiserum that protected mice against challenge with M5, M6, and M24 strains of GAS.

The identification of two protective epitopes of GBS, the N-terminus and the tandem repeat region, will facilitate the development of a conjugate vaccine against GBS. One vaccine strategy is to use the recombinant alpha containing the N-terminus plus two tandem repeats (Gravekamp, C., et al., *Infect. Immun.* 64:3576–3583 (1996)). This recombinant protein confers passive protection in a neonatal mouse protection assay. However, to increase the efficacy of a vaccine based on the two-repeat protein, this recombinant antigen can be coupled to several different N-terminal and repeat regions from other surface-associated proteins of GBS such as the Rib protein, which is commonly found on many serotype III strains. By combining multiple, distinct, and conserved protective epitopes to form a multivalent vaccine, it should be possible to raise antibodies against the majority of clinically significant GBS isolates. Similar strategies for producing vaccines will be used with the N-terminal portion of the epsilon antigen.

EXAMPLE 15

Mouse protection by Epsilon C-protein N-terminal-Specific Antibodies

A mouse protection study is conducted to investigate using epsilon C-protein N-terminal-specific antibodies (either in a conjugated or a non-conjugated form) to protect neonatal mice against infection with alpha and/or epsilon C-protein-bearing strains of GBS. Pregnant dams are passively immunized with postimmunization rabbit antiserum raised to the N-terminal region of the epsilon antigen, preimmunization rabbit serum, (negative control), and rabbit antiserum to the Ia-TT protein-capsular-polysaccharide conjugate (positive control) (Wessels, M. R., et al., *Infect. Immun.* 61:47604766 (1993)). Antiserum is also raised to a conjugate vaccine comprising (a) a group B Streptococcus capsular polysaccharide conjugated to (b) the N-terminal region of the epsilon antigen or a fragment thereof, where said N-terminal region or fragment is capable of eliciting protective antibodies against the group B Streptococcus, and where said conjugate vaccine is substantially free of streptococcal proteins other than the C-protein epsilon antigen.

A preparation that is "substantially free" of streptococcal proteins other than the N-terminal region of the epsilon antigen should be understood as referring to a preparation wherein the only streptococcal protein is that of the terminal region of the epsilon antigen or fragments thereof. Though proteins may be present in the preparation which are homologous to other streptococcal proteins, the sample is still said to be substantially free of other streptococcal proteins as long as the homologous protein contained in the sample are not expressed from genes obtained from Streptococcus. Finally, "substantially free" of streptococcal proteins other than the N-terminal region of the epsilon antigen is not mean to exclude preparations which might contain trace amounts of such proteins.

The neonatal mouse model of Rodewald (Rodewald et al., *Infect. Immun.* 61:4760–4766 (1993) is then used to determine the protective effect of the antiserum. An animal model for determining the dose response of humans to conjugate vaccines comprising a bacterial polysaccharide and a strongly immunogenic carrier protein is that described in U.S. Pat. No. 5,604,108.

EXAMPLE 16

GBS Type III Polysaccharide-Epsilon Antigen N-terminal Region Conjugate Vaccine

A conjugate vaccine is prepared similar to Madoff et al. (*J. Clin. Invest.* 94:286–292 (1994). Oxidized type III polysaccharide (5.5 mg) is combined with 5 mg. of the N-terminal region of the epsilon antigen in a phosphate buffered saline at pH 9.0. Cyanoborohydride is added to the mixture incubated at room temperature insure complete coupling. The pH of the reaction is maintained at 9.0–9.5. Progress of the conjugation is monitored by gel filtration chromatography (Paoletti et al., *Trends in Glycosci. Glycotechnol.* 4:269–278, (1992)). the conjugation is considered to be complete when the magnitude of the protein peak occurring at the void volume of a Superose 6 column (Pharmacia Fine Chemical, Piscataway, N.J. remains constant. After completion, the conjugate vaccine is separated from uncoupled components.

EXAMPLE 17

Passive Immunization

The invention is also related to a method of passive immunization, used particularly for infants or compromised adults. The capsular polysaccharide-N-terminal region epsilon antigen conjugate or a non-conjugated N-terminal region epsilon antigen is injected into a human to raise antibodies thereto to a high titer. The antiserum from the blood of the human is separated and fractionated to produce a gamma globulin fraction containing the antibodies, that can be used for passive immunization. This method of establishing donors for passive immunization is useful because, although occasional non-immunized individual have very high levels of type-specific GBS antibody in their sera, it would be necessary to screen very large populations to select those individuals whose plasma could be pooled to make sufficiently high titered globulin fractions to be useful for passive immunizations.

For passive immunization, pools of human sera from selected individuals vaccinated with the conjugated vaccine can be concentrated and fractionated by conventional procedures. This provides a globulin fraction containing most of the type-specific antibody and has sufficiently high activity so that the hyperimmune globulin is effective in small doses of 0.3–1.0 ml, preferably a about 0.5 ml. The globulin fraction is administered either intravenously or intramuscularly in a suitable physiologically acceptable carrier. Such a carrier includes, but is not limited to, normal saline. The concentration of the globulin in the carrier may be from 5 to 20% by weight. The hyperimmune globulin can be administered either to pregnant women prior to deliver, to neonates, or to immunologically compromised individuals, to provide passive immunization or therapy.

EXAMPLE 18

Diagnostic Tool

The DNA obtained by cloning the plasmid pJMS36 may be used as a diagnostic tool for determining infections with Group B Streptococcus expressing the epsilon antigen. Such knowledge should provide those of skill in the art with more rational approaches for the treatment of GBS infection. Such a tool is a useful as an adjunct for diagnosis of GBS infection or as a molecular marker of epidemiological significance.

After obtaining an appropriate sample for culturing from an individual in need of diagnosis, the bacterial DNA is extracted and analyzed by Southern blot analysis to determine whether the GBS bacteria carries an epsilon antigen. The means for culturing the sample, extracting and analyzing the DNA from the infected individual are well-known to those of skill in the art.

All references cited are incorporated herein by reference. While the invention has been described in detail and with reference to specific embodiments thereof, it will be apparent to one skilled in the art that various changes and modifications could be made therein without departing from the spirt and scope thereof.

What is claimed is:

1. A conjugate vaccine comprising (a) a group B Streptococcus capsular polysaccharide conjugated to (b) the N-terminal region of the group B Streptococcus epsilon antigen the sequence of which is shown in FIG. 6B (SEQ ID NO:4), wherein said conjugate vaccine is substantially free of Streptococcal proteins other than said C protein epsilon antigen, wherein said conjugate vaccine elicits antibodies against group B Streptococcus, thereby conferring host immunity to an infection by Group B Streptococcus.

2. A conjugate vaccine comprising (a) a group B Streptococcus capsular polysaccharide conjugated to (b) the N-terminal region of the group B Streptococcus epsilon antigen the sequence of which is shown in FIG. 6B (SEQ ID NO:4), said capsular polysaccharide also being conjugated to a group B Streptococcus C-protein selected from the group consisting of a group B Streptococcus alpha antigen, a group B Streptococcus beta antigen, an immunogenic fragment of said alpha antigen and an immunogenic fragment of said beta antigen wherein said conjugate vaccine elicits protective antibodies against group B Streptococcus thereby conferring protective host immunity to an infection by group B Streptococcus.

3. A method for preventing or treating an infection caused by a group B Streptococcus comprising administering to an individual, an effective amount of the conjugate vaccine of any one of claims 1 or 2.

4. A method for preventing or treating an infection caused by a group B Streptococcus comprising administering to a female an effective amount of the conjugate vaccine of any one of claims 1 or 2, said vaccine capable of conferring immunity to said infection to an unborn offspring of said pregnant female.

5. The conjugate vaccine of any one of claims 1 or 2 wherein said capsular polysaccharide is type-specific.

6. The conjugate vaccine of any one of claims 1 or 2 wherein said capsular polysaccharide is group-specific.

7. The vaccine of any one of claims 1 or 2, further comprising a pharmacologically acceptable solution.

8. The conjugate vaccine of any one of claims 1 or 2, wherein said epsilon antigen from more than one strain of Group B Streptococcus is used in said vaccine.

9. The conjugate vaccine of claim 1 or 2 wherein said N-terminal region of the epsilon antigen comprises the amino acid sequence of SEQ ID NO:4.

* * * * *